US012616467B2

(12) United States Patent
Batty et al.

(10) Patent No.: US 12,616,467 B2
(45) Date of Patent: May 5, 2026

(54) SYSTEMS AND SUBSYSTEMS FOR ARTICULATING A SURGICAL INSTRUMENT

(71) Applicant: CILAG GMBH INTERNATIONAL, Zug (CH)

(72) Inventors: Christopher Batty, Cincinnati, OH (US); Raffaele Definis, Cincinnati, OH (US); Robert Jason Simms, Cincinnati, OH (US); Jonathan Von Stein, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/775,057

(22) Filed: Jul. 17, 2024

(65) Prior Publication Data

US 2025/0025157 A1 Jan. 23, 2025

Related U.S. Application Data

(60) Provisional application No. 63/634,171, filed on Apr. 15, 2024, provisional application No. 63/634,201,
(Continued)

(51) Int. Cl.
*A61B 17/072* (2006.01)
*A61B 17/068* (2006.01)
(Continued)

(52) U.S. Cl.
CPC ...... *A61B 17/072* (2013.01); *A61B 17/07207* (2013.01); *A61B 34/30* (2016.02);
(Continued)

(58) Field of Classification Search
CPC . A61B 17/068; A61B 17/0686; A61B 17/072; A61B 17/07207; A61B 2017/07214–07285; A61B 34/30
(Continued)

(56) References Cited

U.S. PATENT DOCUMENTS 8,292,150 B2 10/2012 Bryant
8,460,275 B2 * 6/2013 Taylor ................ A61B 17/0469
606/1
(Continued)

FOREIGN PATENT DOCUMENTS

EP 2768418 B1 7/2017
EP 2811932 B1 6/2019
(Continued)

OTHER PUBLICATIONS

International Search Report and Written Opinion for Related PCT Appl. No. PCT/IB2024/056981, Dated Oct. 22, 2024.

*Primary Examiner* — Linda J. Hodge
(74) *Attorney, Agent, or Firm* — Troutman Pepper Locke LLP

(57) ABSTRACT

Systems and subsystems for articulating an end effector of a stapler are disclosed. More specifically, the present disclosure relates to systems, devices, and subsystems for attachments for robotic surgeries. The surgical instrument is a robotic attachment. The surgical instrument includes an articulation subsystem that moves independently of other subsystems that are operable independently of each other.

14 Claims, 44 Drawing Sheets

Related U.S. Application Data filed on Apr. 15, 2024, provisional application No. 63/515,001, filed on Jul. 21, 2023, provisional application No. 63/514,972, filed on Jul. 21, 2023.

(51) Int. Cl.
| | |
|---|---|
| *A61B 17/29* | (2006.01) |
| *A61B 34/30* | (2016.01) |
| *A61B 17/00* | (2006.01) |

(52) U.S. Cl.
CPC ... *A61B 2017/00367* (2013.01); *A61B 17/068* (2013.01); *A61B 17/0686* (2013.01); *A61B 2017/07257* (2013.01); *A61B 2017/07271* (2013.01); *A61B 2017/07285* (2013.01); *A61B 2017/2903* (2013.01)

(58) Field of Classification Search
USPC .......................................... 227/175.1–182.1
See application file for complete search history.

(56) References Cited

U.S. PATENT DOCUMENTS

| | | | |
|---|---|---|---|
| 8,800,838 | B2 | 8/2014 | Shelton, IV et al. |
| 9,232,979 | B2 | 1/2016 | Parihar et al. |
| 10,085,748 | B2 * | 10/2018 | Morgan ............... A61B 17/072 |
| 10,143,524 | B2 | 12/2018 | Koch |
| 10,251,716 | B2 | 4/2019 | Overmyer |
| 10,307,215 | B2 | 6/2019 | Swayze |
| 10,327,854 | B2 | 6/2019 | Overmyer |
| 10,376,276 | B2 | 8/2019 | Overmyer |
| 10,433,920 | B2 | 10/2019 | Overmyer |
| 10,542,982 | B2 | 1/2020 | Beckman |
| 10,675,025 | B2 | 6/2020 | Swayze |
| 10,702,349 | B2 | 7/2020 | Overmyer |
| 10,918,385 | B2 | 2/2021 | Overmyer |
| 10,987,177 | B2 | 4/2021 | Overmyer et al. |
| 11,033,344 | B2 | 6/2021 | Overmyer |
| 11,058,477 | B2 | 7/2021 | Messerly et al. |
| 11,191,539 | B2 | 12/2021 | Overmyer |
| 11,191,543 | B2 | 12/2021 | Overmyer |
| 11,191,560 | B2 | 12/2021 | Overmyer |
| 11,219,495 | B2 | 1/2022 | Overmyer et al. |
| 11,419,605 | B2 | 8/2022 | Denzinger |
| 11,419,606 | B2 | 8/2022 | Overmyer |
| 11,439,474 | B2 | 9/2022 | Kallenberger |
| 11,446,098 | B2 | 9/2022 | Swayze |
| 11,471,228 | B2 | 10/2022 | Overmyer |
| 11,547,494 | B2 | 1/2023 | Swayze |
| 11,559,366 | B2 | 1/2023 | Overmyer |
| 11,622,825 | B2 | 4/2023 | Overmyer |
| 11,813,032 | B2 | 11/2023 | Overmyer |
| 11,813,746 | B2 | 11/2023 | Overmyer |
| 11,864,954 | B2 | 1/2024 | Overmyer |
| 12,023,116 | B2 | 7/2024 | Overmyer |
| 12,070,287 | B2 | 8/2024 | Overmyer |
| 2003/0130677 | A1 | 7/2003 | Whitman et al. |
| 2007/0023476 | A1 | 2/2007 | Whitman et al. |
| 2009/0114699 | A1 | 5/2009 | Viola |
| 2014/0263541 | A1 | 9/2014 | Leimbach et al. |
| 2014/0303645 | A1 | 10/2014 | Morgan et al. |
| 2016/0067001 | A1 * | 3/2016 | Parihar ................... A61B 34/25 606/52 |
| 2016/0174976 | A1 * | 6/2016 | Morgan ............... A61B 17/072 227/175.1 |
| 2016/0174978 | A1 | 6/2016 | Overmyer et al. |
| 2016/0213438 | A1 | 7/2016 | Jogasaki et al. |
| 2019/0021752 | A1 * | 1/2019 | Boudreaux .... A61B 17/320068 |
| 2019/0105117 | A1 | 4/2019 | Brisson et al. |
| 2019/0183491 | A1 | 6/2019 | Shelton, IV et al. |
| 2019/0183504 | A1 * | 6/2019 | Shelton, IV ..... A61B 17/07207 |
| 2019/0183592 | A1 | 6/2019 | Shelton, IV et al. |
| 2019/0183597 | A1 | 6/2019 | Shelton, IV et al. |
| 2020/0093489 | A1 | 3/2020 | Parihar et al. |
| 2020/0330120 | A1 | 10/2020 | Koch, Jr. et al. |
| 2020/0375596 | A1 | 12/2020 | Corsetto |
| 2021/0059664 | A1 | 3/2021 | Hensel et al. |
| 2021/0059773 | A1 | 3/2021 | Overmyer et al. |
| 2021/0059777 | A1 * | 3/2021 | Overmyer .............. A61B 34/71 |
| 2021/0346050 | A1 | 11/2021 | Boudreaux et al. |
| 2022/0105638 | A1 * | 4/2022 | Zhang ..................... B25J 13/06 |
| 2022/0105639 | A1 | 4/2022 | Zhang et al. |
| 2022/0125538 | A1 | 4/2022 | Overmyer et al. |
| 2022/0192707 | A1 | 6/2022 | Barakat et al. |
| 2022/0346897 | A1 | 11/2022 | Black et al. |
| 2022/0409310 | A1 | 12/2022 | Overmyer et al. |
| 2023/0001579 | A1 | 1/2023 | Overmyer |
| 2023/0181275 | A1 | 6/2023 | Overmyer |
| 2023/0338051 | A1 | 10/2023 | Robert, Jr. |
| 2023/0355338 | A1 | 11/2023 | Overmyer |
| 2024/0081191 | A1 | 3/2024 | Beckman |
| 2024/0271574 | A1 | 8/2024 | Hill et al. |

FOREIGN PATENT DOCUMENTS

| | | | |
|---|---|---|---|
| EP | 2866697 | B1 | 12/2021 |
| KR | 20150100137 | A | 9/2015 |
| WO | 2020212875 | A1 | 10/2020 |
| WO | 2021038360 | A2 | 3/2021 |
| WO | 2022144818 | A1 | 7/2022 |
| WO | 2023225866 | A1 | 11/2023 |

* cited by examiner

442/448

430/436

434/440

446/452

444/450

434/440

414/418

416/420

446/452

458/460

430/436

432/438

402/404

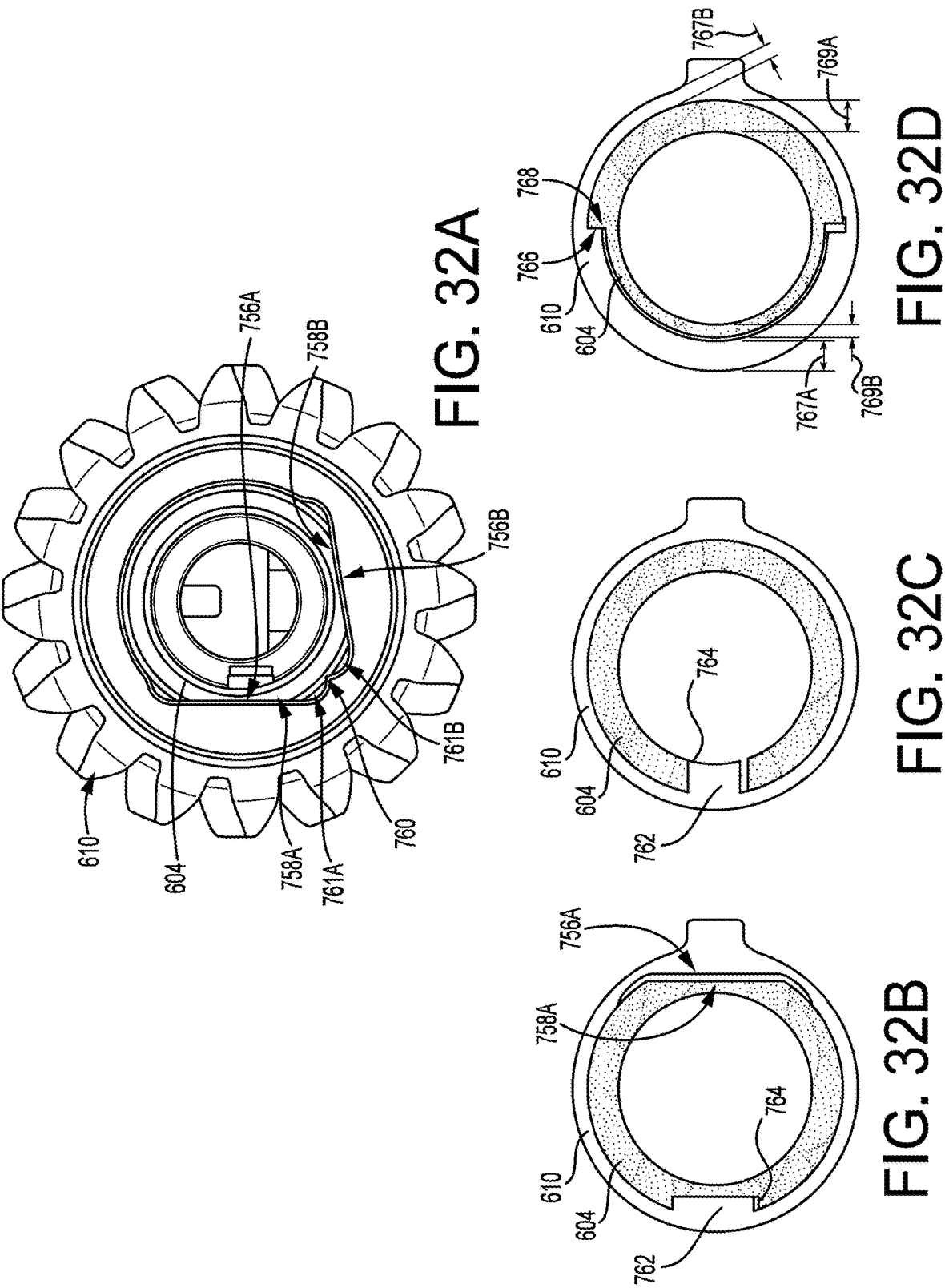

SYSTEMS AND SUBSYSTEMS FOR ARTICULATING A SURGICAL INSTRUMENT

CROSS REFERENCE TO RELATED APPLICATIONS

The present application claims the benefit of, and priority to, U.S. Provisional Application Ser. No. 63/514,972 filed on Jul. 21, 2023, U.S. Provisional Application Ser. No. 63/515, 001 filed on Jul. 21, 2023, U.S. Provisional Application Ser. No. 63/634,201 filed on Apr. 15, 2024, and U.S. Provisional Application Ser. No. 63/634,171 filed on Apr. 15, 2024, the disclosures of which are expressly incorporated herein by reference.

FIELD OF INVENTION

The present disclosure generally relates to systems, devices, and subsystems for cutting and stapling tissue. More specifically, the present disclosure relates to systems, devices, and subsystems for attachments for robotic surgeries.

BACKGROUND

Stapling is a crucial aspect of many surgical procedures, such as gastrointestinal, thoracic, and gynecological surgeries. Robotic surgical systems have gained significant recognition in recent years due to their potential to enhance surgical precision and dexterity. However, the development of a dedicated surgical stapling instrument that integrates seamlessly into the surgical workflow of a multi-purpose robot remains an unmet need for many surgeons.

SUMMARY

It is an object of the present designs to provide devices and methods to meet the above-stated needs. The designs can be for systems, devices, and subsystems for stapling attachments for robotic surgeries. The attachments can have several subsystems that can be independently actuated to provide a specific action, such as closing of an end effector of the stapler, articulation of the end effector, rolling of the end effector, and firing of the staples within the end effector.

The instant disclosure describes an articulation subsystem, which can be one of a number of subsystems for a surgical instrument. The articulation subsystem includes a rotatable shaft having a longitudinal axis. The articulation subsystem includes a distal channel retainer coupled to an end effector, the distal channel retainer being pivotable about an articulation joint. The articulation subsystem includes a first articulation bushing slidable from a first position to a second position along the longitudinal axis of the rotatable shaft. The articulation subsystem includes an articulation rod extending distally from the first articulation bushing and coupled at a distal end to the distal channel retainer. The articulation subsystem includes a first rack movable with respect to the longitudinal axis of the rotatable shaft. Movement of the first rack with respect to the longitudinal axis imparts an axial force onto the first articulation bushing moving the first articulation bushing from the first position to the second position. Movement of the first articulation bushing from the first position to the second position actuates the articulation rod causing the distal channel retainer to pivot about the articulation joint.

The instant disclosure describes an articulation subsystem, which can be one of a number of subsystems for a surgical instrument. The articulation subsystem includes a rotatable shaft having a longitudinal axis. The articulation subsystem includes an articulation rod extending along the longitudinal axis of the rotatable shaft and being rotationally coupled to the rotatable shaft. The articulation subsystem includes a first articulation bushing slidable from a first position to a second position along the longitudinal axis of the rotatable shaft, the first articulation bushing being rotationally coupled to the rotatable shaft. The articulation subsystem includes a first rack movable with respect to the longitudinal axis of the rotatable shaft, the first rack being rotationally independent of the rotatable shaft and the first articulation bushing. The articulation subsystem includes a first rack gear engaged with the first rack. Rotation of the first rack gear moves the first rack with respect to the longitudinal axis. Movement of the first rack with respect to the longitudinal axis imparts an axial force onto the first articulation bushing moving the first articulation bushing from the first position to the second position.

Other aspects of the present disclosure will become apparent upon reviewing the following detailed description in conjunction with the accompanying figures. Additional features or manufacturing and use steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

FIG. 5A depicts a surgical instrument with an "outboard" articulation subsystem, according to aspects of the present disclosure. FIG. 5B depicts a surgical instrument with an "inboard" articulation subsystem, according to aspects of the present disclosure.

FIG. 8 shows the closure subsystem in an open configuration, and FIG. 9 shows the closure subsystem in a closed configuration, according to aspects of the present disclosure.

FIG. 14 shows the articulation subsystem at 0° degrees of articulation, and FIG. 15 shows the articulation subsystem fully articulated in one direction.

FIG. 22 shows the end effector articulated right, FIG. 23 shows the end effector unarticulated (i.e., straight), and FIG. 24 shows the end effector articulated left.

FIG. 26 is a perspective view of the components of the roll subsystem, and FIG. 27 is a cross-sectional view of the components of the roll subsystem.

FIG. 28 shows the roll subsystem a first end position of roll, FIG. 29 shows the roll subsystem an intermediate position of roll, and FIG. 30 shows the roll subsystem a second end position of roll.

FIG. 31A is a perspective view of the components of the roll subsystem, and FIG. 31B is a top, cross-sectional view of the components of the roll subsystem.

FIGS. 32A-32D provide examples of anti-backlash features for a worm follower engaged with a rotatable shaft, according to aspects of the present disclosure. FIG. 32A shows an example of a shaft with two flat sections (or "flats"), FIG. 32B shows an example of a shaft with a keyway and a worm follower with a corresponding key feature, FIG. 32C shows an example of a shaft with a keyway and a worm follower with a corresponding key feature, and FIG. 32D shows an example of a shaft and a worm follower with corresponding steps or ledges.

FIG. 33A is a side cross sectional view thereof, and FIG. 33B is cross sectional view from the direction indicated in FIG. 33A.

DETAILED DESCRIPTION

Specific examples of the present invention are now described in detail with reference to the Figures, where identical reference numbers indicate elements which are functionally similar or identical. The examples address many of the deficiencies associated with prior robotic attachment systems, for instance prior systems that did not provide integrated capabilities to close, articulate, roll, and fire, all with the actuation of their designated robotic outputs. The present surgical instrument includes a housing that contains the gearing and other components necessary to effect the close, articulate, roll, and fire features. In particular, the present disclosure provides a detailed discussion of the closure subsystem, articulation subsystem, roll subsystem, and transection subsystem that are usable to close, articulate, roll, and fire an end effector of the device. Use of the term "fire" throughout this disclosure means to advance the distal portions of the transection subsystem distally. "Firing" the components shall be understood to mean acts to cut, staple, or both.

Overview

Figure 1:
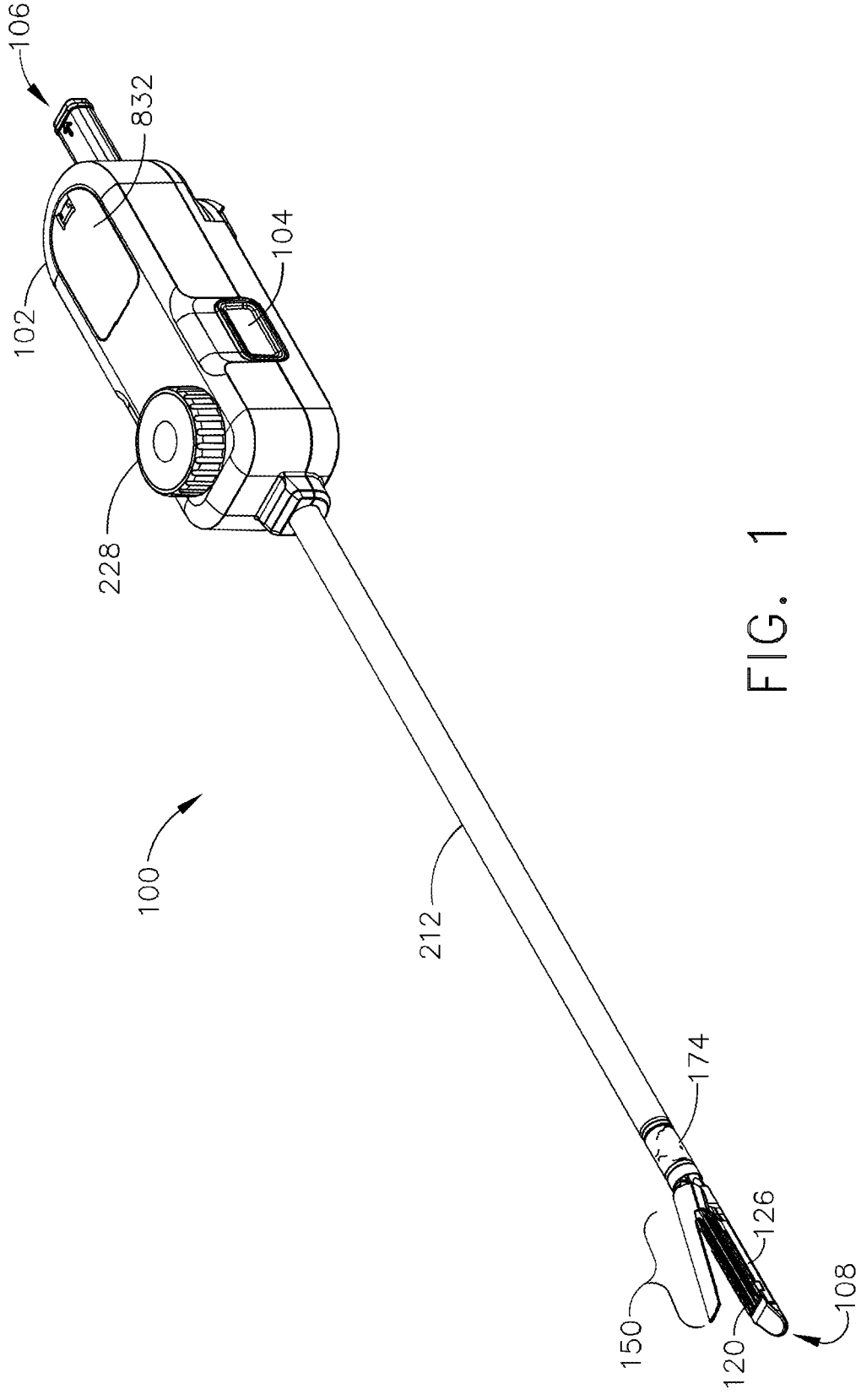
FIG. 1 shows a surgical instrument, according to aspects of the present disclosure.

Turning to the figures, FIG. 1 is a perspective view illustrating a surgical instrument 100, according to aspects of the present disclosure. A housing 102 of the surgical instrument 100 can be attachable to a robotic arm that includes a plurality of outputs, or rotatable disks, that can actuate pucks, or other disks, on the surgical instrument 100. The proximal end 106 of the surgical instrument 100 is therefore attachable to the multi-use robot, and the distal end 108 of the surgical instrument 100 effects the transection and stapling of patient tissue. The surgical instrument can include a release button 104 that allow the device to be detached from the robotic arm. As shown, the surgical instrument 100 can include more than one release buttons 104.

Figure 2:
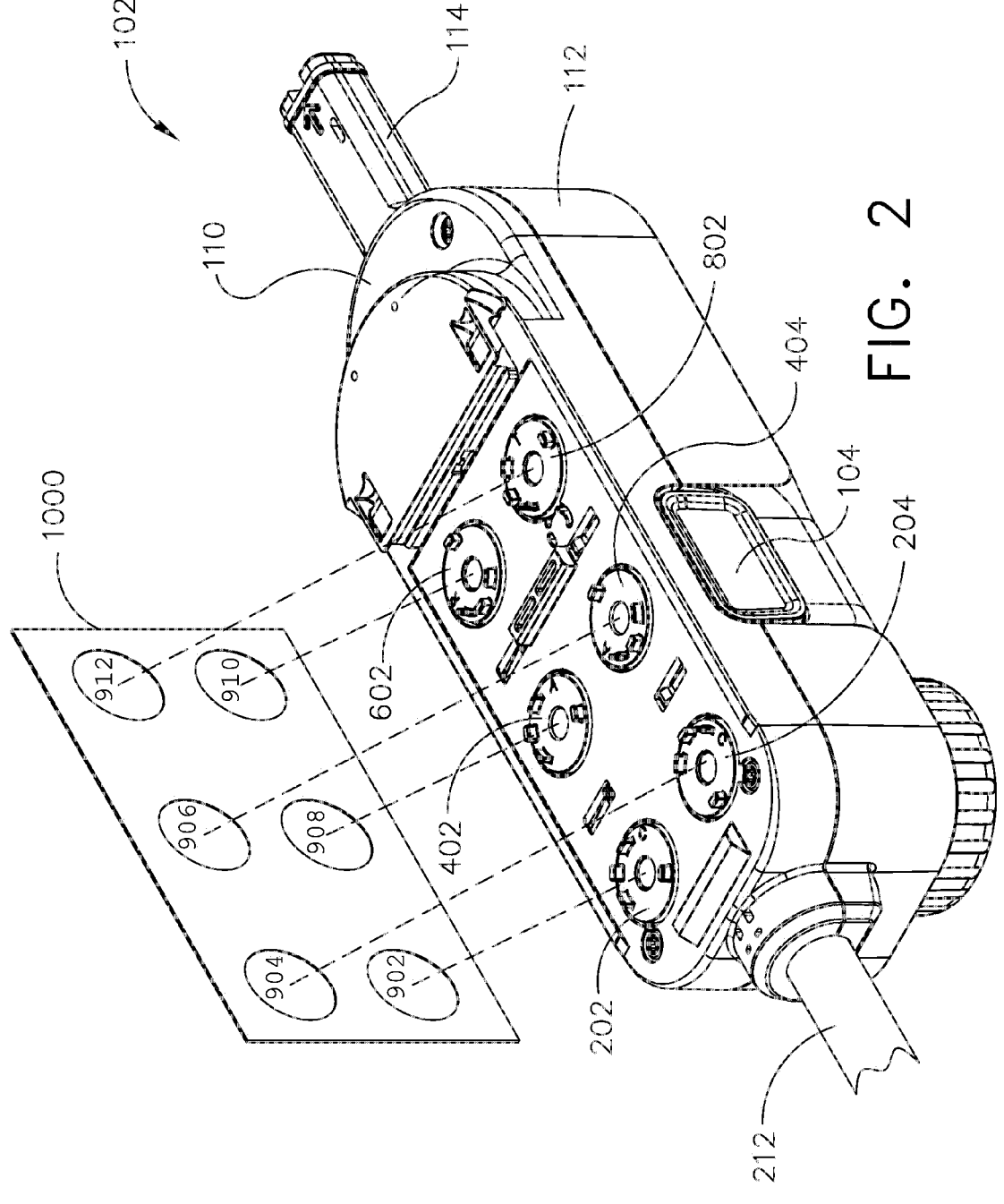
FIG. 2 shows a housing at a proximal end of a surgical instrument, according to aspects of the present disclosure.
Figure 3:
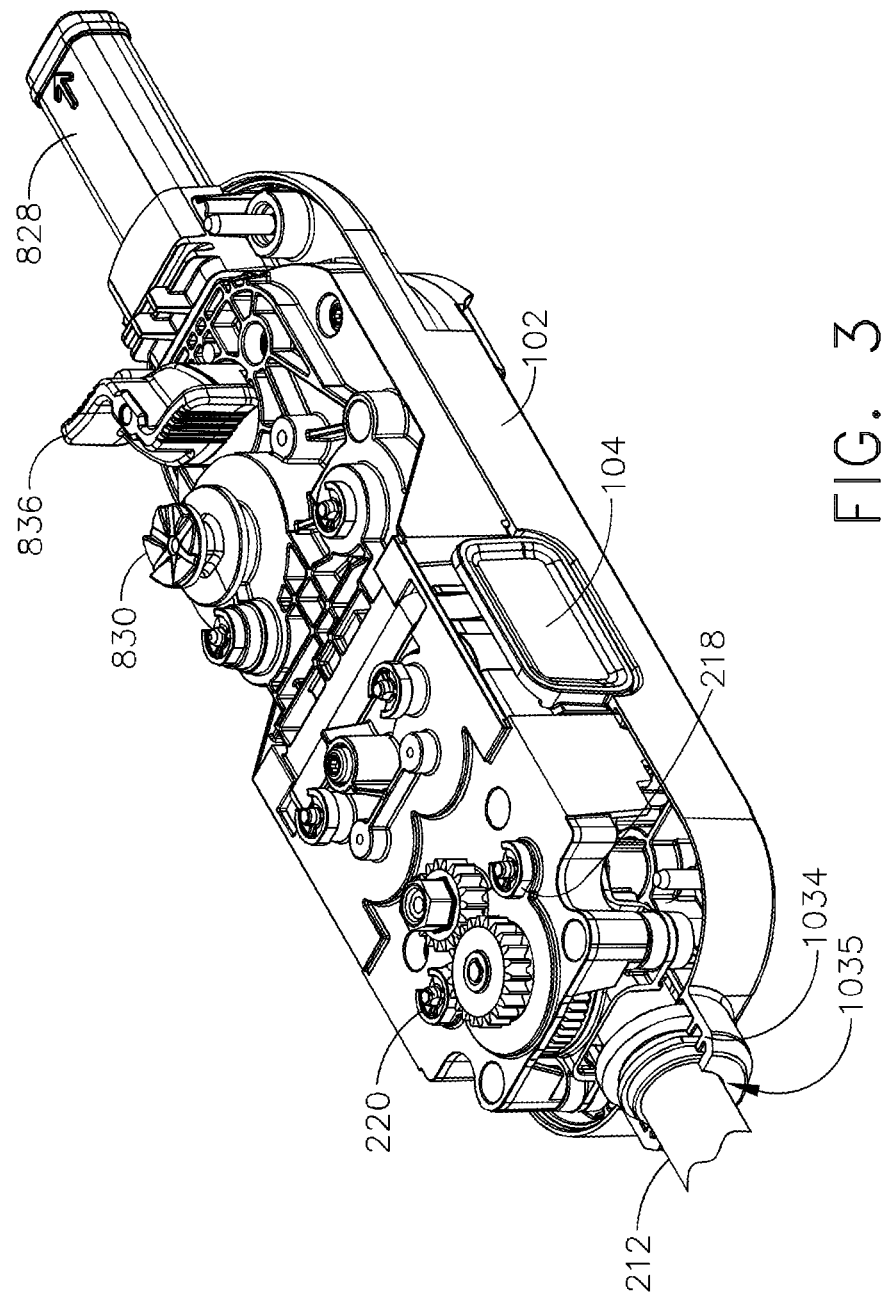
FIGS. 3 and 4 show internal components of a housing at a proximal end of a surgical instrument, according to aspects of the present disclosure.
Figure 4:
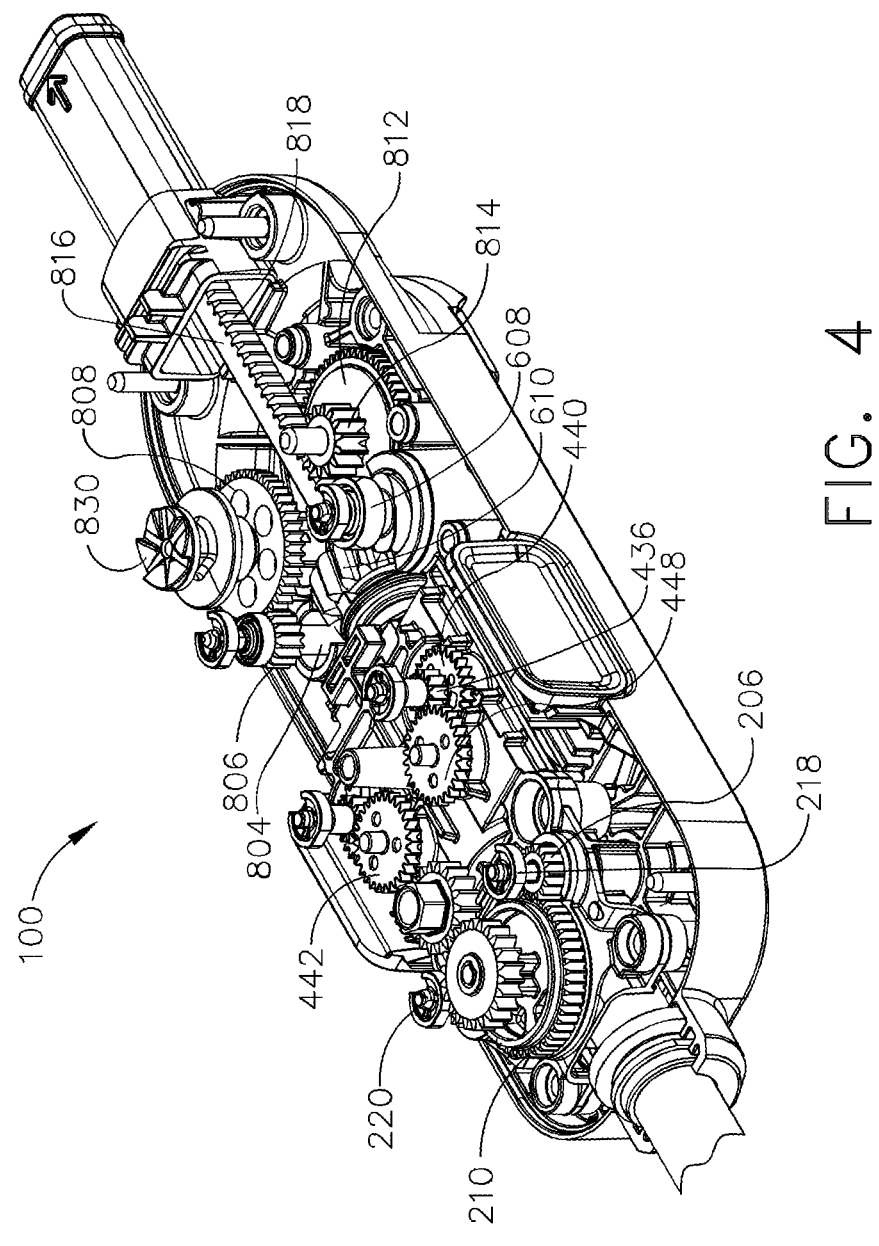

FIG. 2 is a perspective view of the housing 102 as shown from the opposite side from what is shown in FIG. 1. The housing 102 can include a first portion 110 and a second portion 112. The housing 102 includes a series of pucks (e.g., first closure input puck 202, second closure input puck 204, first articulation input puck 402, second articulation input puck 404, roll input puck 602, and transection input puck 802). The pucks can have features that enable them to engage with the rotating features of the robotic arm, such that rotation of the pucks can actuate the gears and other components of the closure subsystem 200, articulation subsystem 400, roll subsystem 600, and transection subsystem 800 described herein. FIGS. 3 and 4 show internal components of the housing 102 at the proximal end 106 of the surgical instrument 100. More detail about features of the housing 102 is provided below, particularly with respect to FIGS. 56A-63B.

Figure 5A:
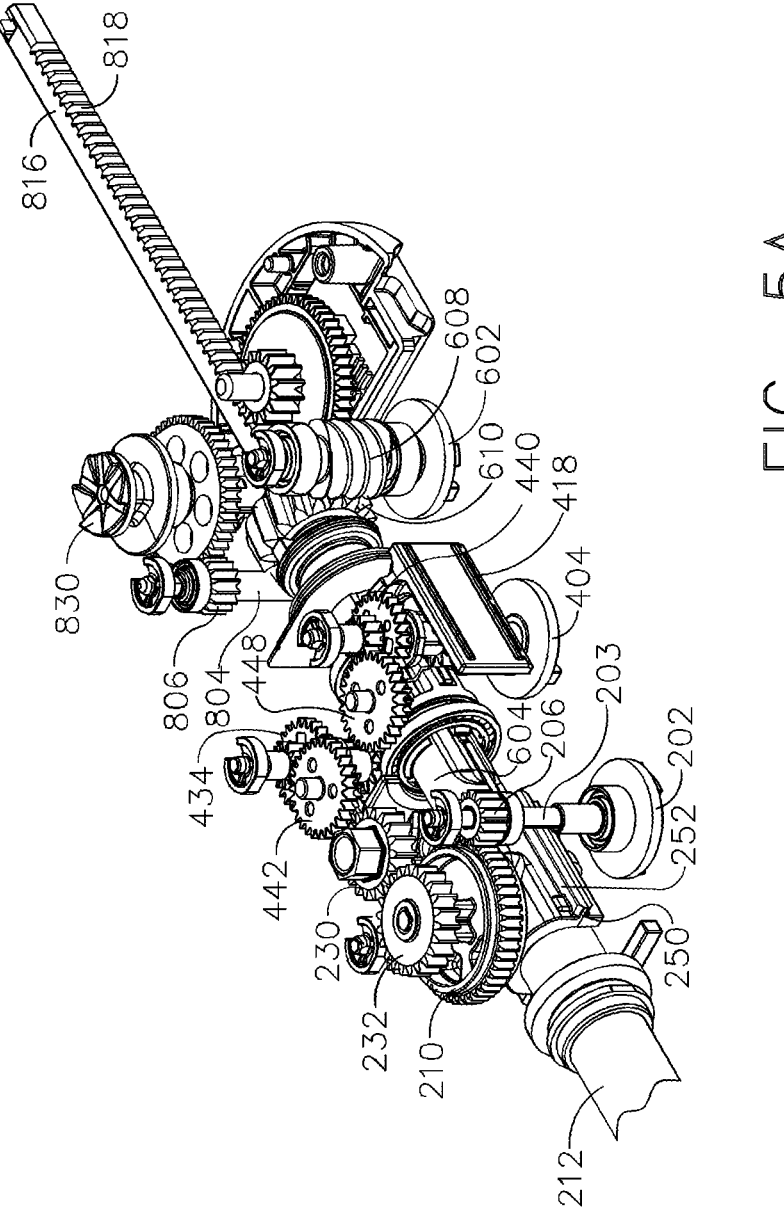
FIGS. 5A and 5B show internal components of a surgical instrument shown without an outer housing, according to aspects of the present disclosure.
Figure 5B:
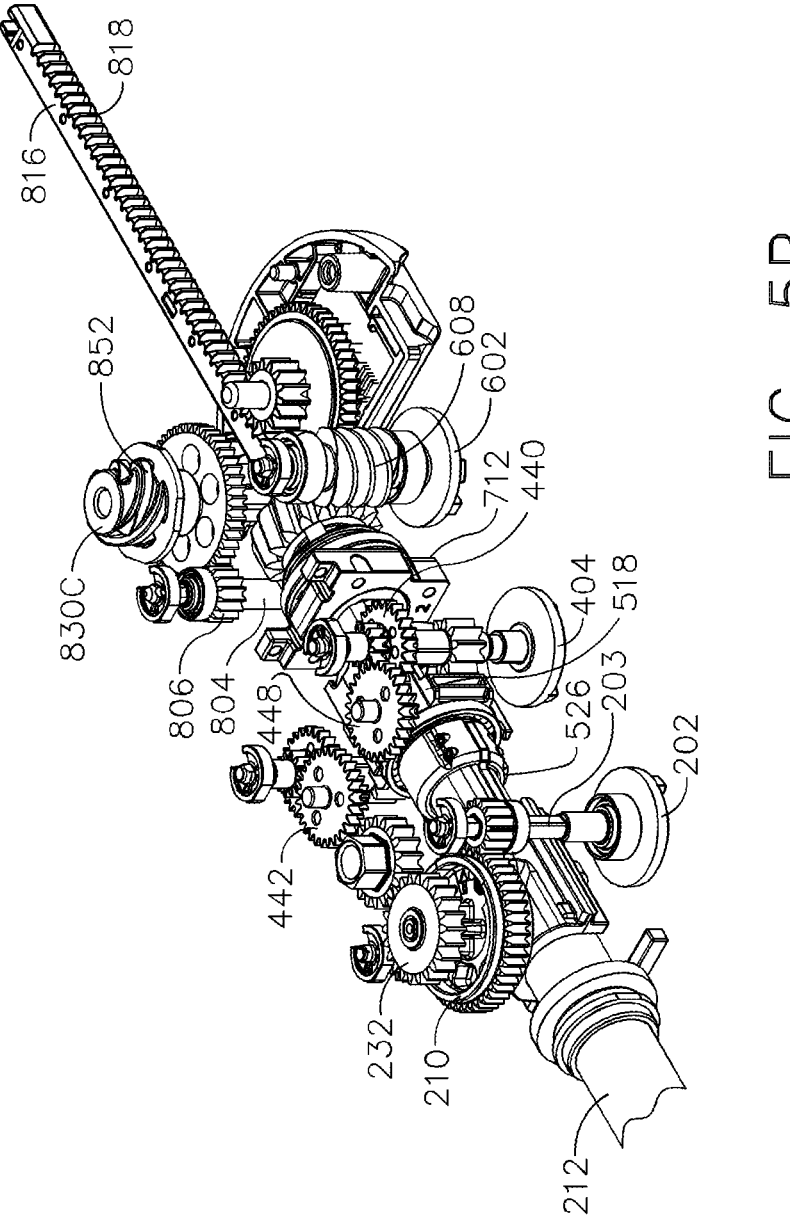
Figure 6A:
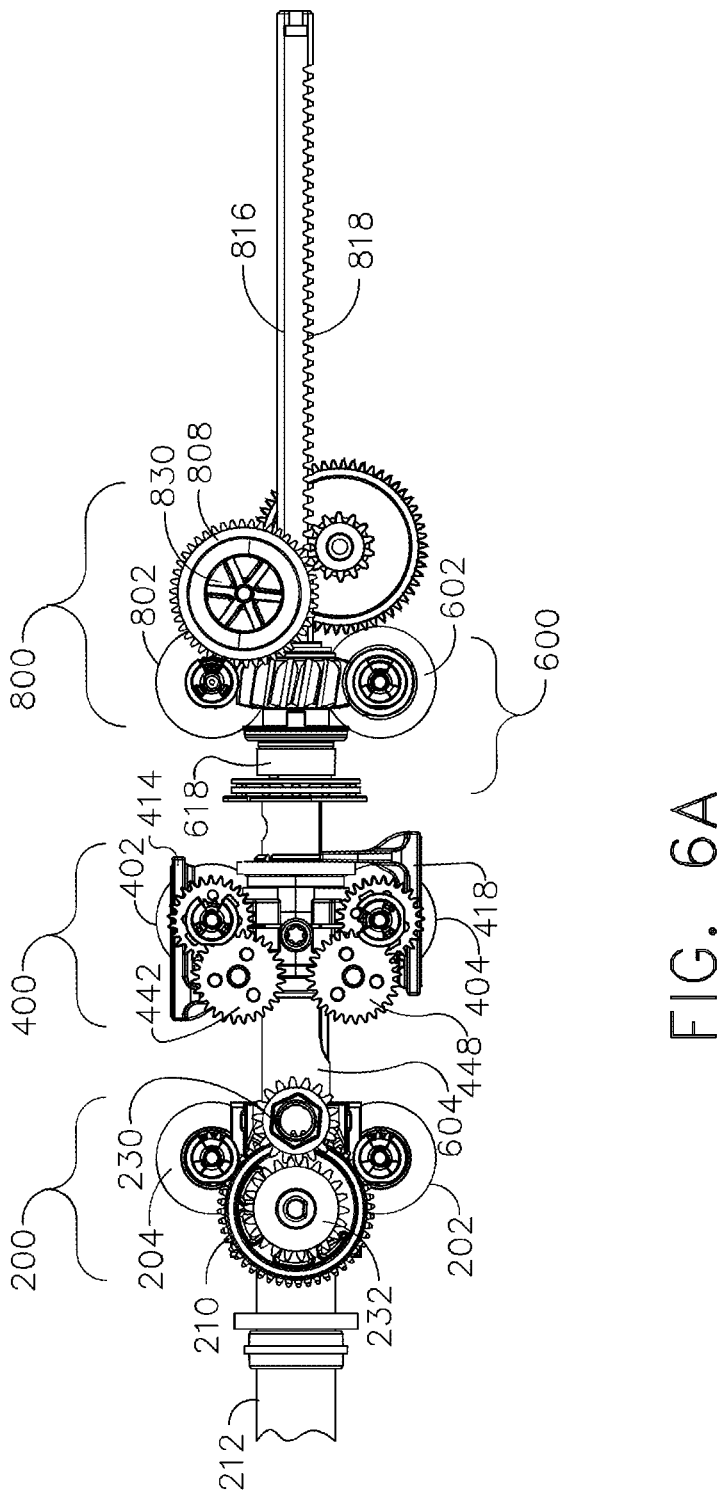
FIG. 6A is a top plan view of the features shown in FIG. 5A.
Figure 6B:
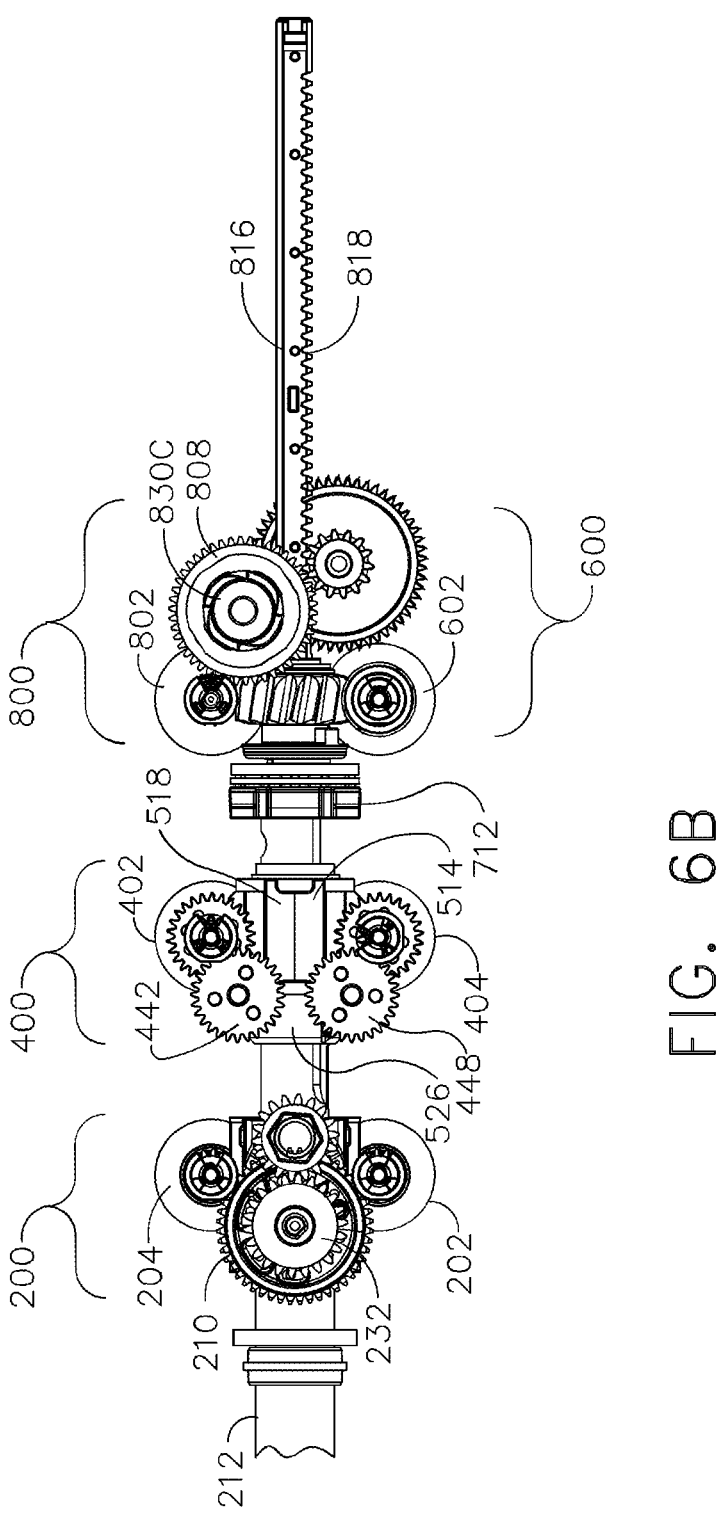
FIG. 6B is a top plan view of the features of FIG. 5B.

FIG. 5A shows internal components of the surgical instrument 100 shown without an outer housing 102, according to aspects of the present disclosure. FIG. 6A is a top plan view of the features shown in FIG. 5A. FIG. 5B depicts a surgical instrument 100 with an "inboard" articulation subsystem, which is described in greater detail below (FIG. 6B is a top plan view of the features of FIG. 5B). The views highlight the different subsystems of the internal components, showing how the closure subsystem 200 and the articulation subsystem 400 each utilize two different pucks (e.g., first closure input puck 202, second closure input puck 204, first articulation input puck 402, and second articulation input puck 404) for their respective actions, whereas the roll subsystem 600 and transection subsystem 800 each utilize only one puck (e.g., roll input puck 602 and transection input puck 802) for their respective actions. As will be described below, alternative embodiments implement the different subsystems with a different number of inputs (i.e., how many pucks are turned to effect their action). There are certain benefits to the closure subsystem 200 and the articulation subsystem 400 utilizing two different pucks, including but not limited to providing additional force for closure and providing antagonistic compression of the bushings for the articulation subsystem 400. FIG. 5A depicts a surgical instrument with an "outboard" articulation subsystem 400. FIG. 5B depicts a surgical instrument with an "inboard"

articulation subsystem 400. The differences between an inboard and outboard system are described in greater detail below.

Figure 35:
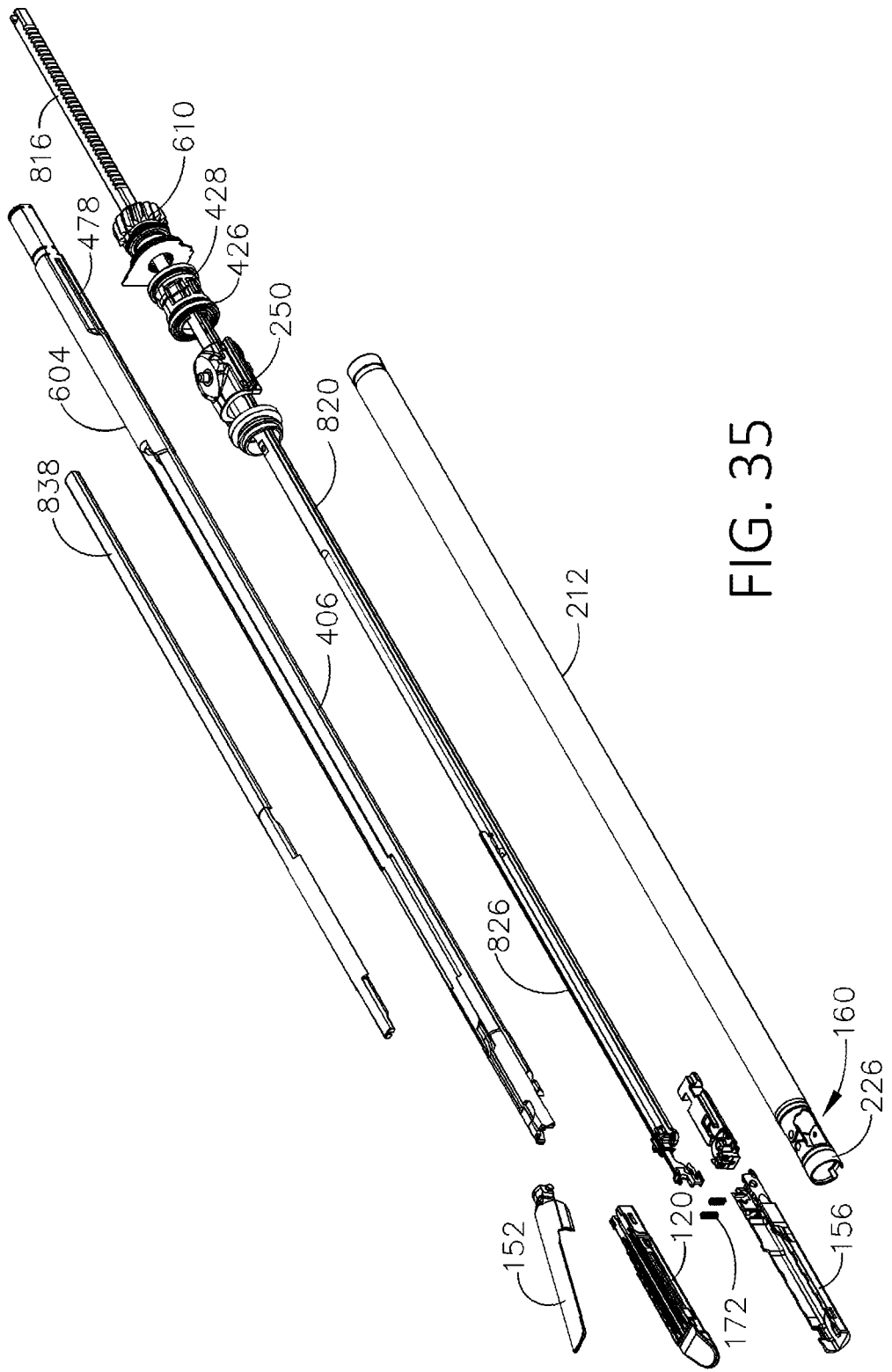
FIG. 35 shows shaft closure and firing components of a surgical instrument, according to aspects of the present disclosure.
Figure 36:
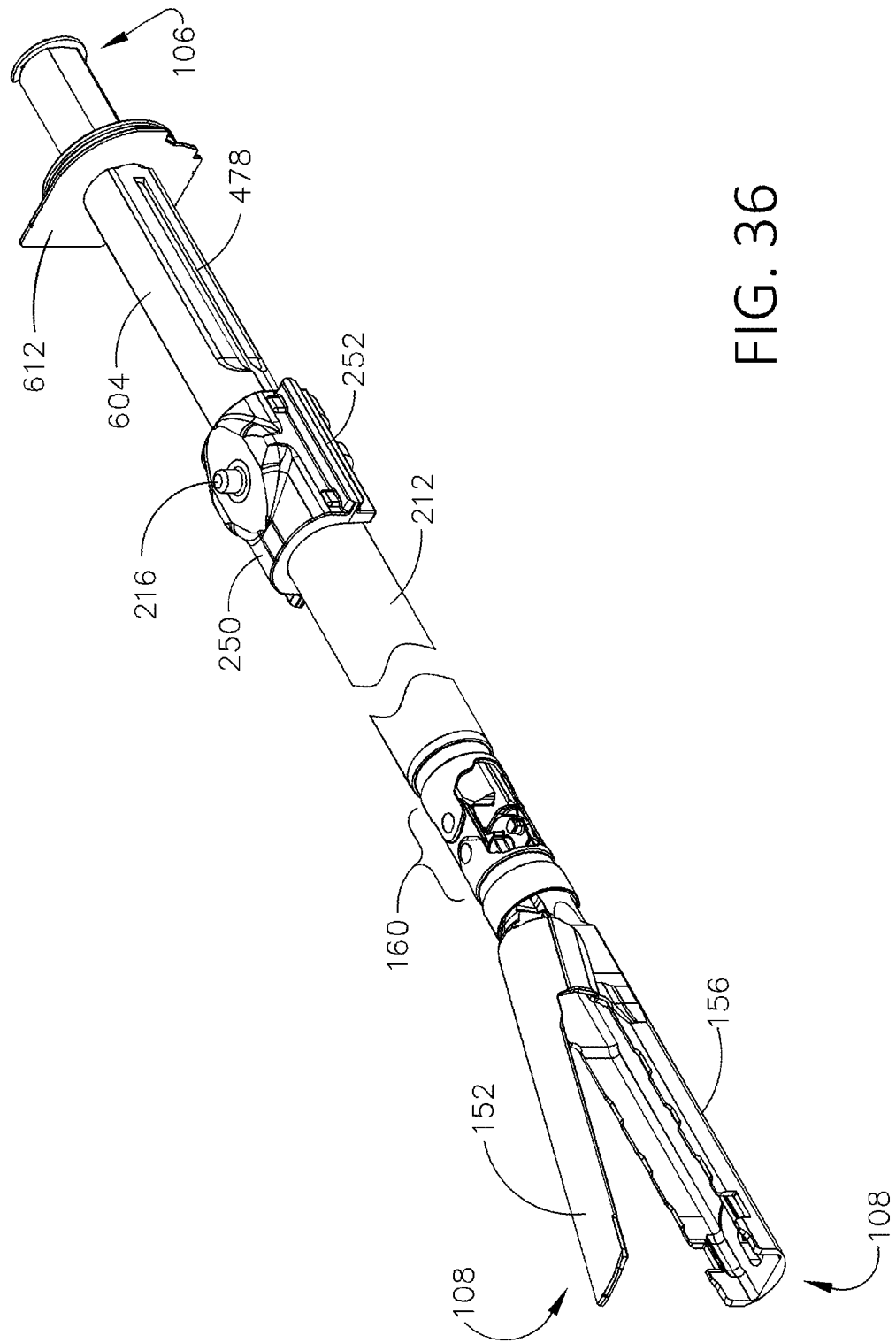
FIG. 36 shows shaft closure components with an anvil in an open position.
Figure 41:
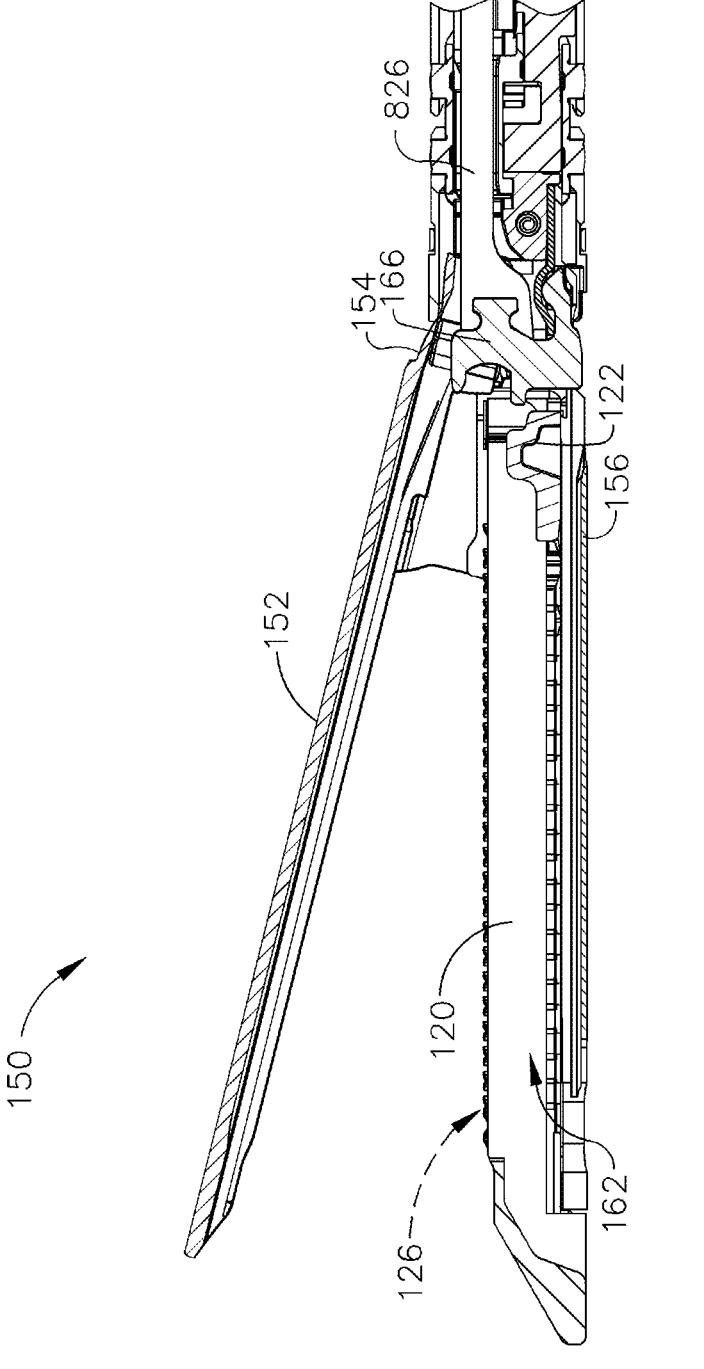
FIG. 41 is a cross-sectional view of an end effector portion of a surgical instrument, according to aspects of the present disclosure. The end effector is in an open configuration.
Figure 42:
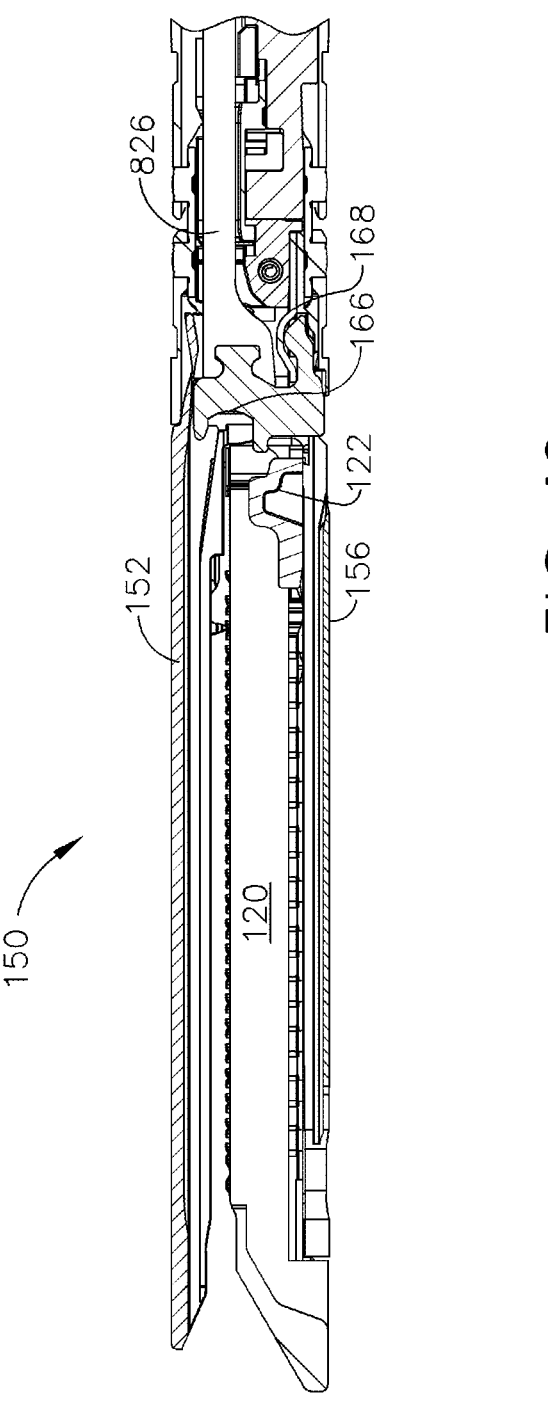
FIG. 42 is a cross-sectional view of an end effector portion of a surgical instrument, according to aspects of the present disclosure. The end effector is in a closed configuration.

As shown in FIGS. 1 and 36, for example, the surgical instrument 100 includes an end effector 150 disposed at the distal end 108 of the surgical instrument 100. As shown, the end effector 150 includes an anvil 152 and a channel 156. As will be described in greater detail herein, the anvil 152 can be caused to move with respect to the channel 156 to open and close the end effector 150. Furthermore, as will be described in greater detail herein, the surgical instrument 100 can include a closure ring 226 and a closure tube 212 that can be actuated to cause the anvil 152 to close with respect to the channel 156. The lower channel 156 can accept a staple cartridge 120 within a cartridge slot 162 therein (see FIG. 41). The anvil 152 can be opened by retracting the closure ring 226 from the anvil 152. The end effector 150 of the disclosed technology can be configured for cutting and stapling of tissue of a patient. FIG. 42 further illustrates an end effector 150 in a closed configuration while FIG. 41 illustrates an end effector 150 in an open configuration. The anvil 152 of the end effector 150 can be opened and closed by operation of a closure ring 226 that is coupled to the anvil 152 and can be slid proximally and distally by the closure tube 212. As the closure ring 226 is slid distally the closure ring 226 causes the anvil 152 to close. The closure subsystem 200 can close the anvil 152 by moving the closure ring 226 distally and over the anvil ramp 154, thereby hinging the anvil 152 closed. As the closure ring 226 is slid proximally, the closure ring 226 slides away from the anvil 152, allowing it to open. The anvil 152 can be biased in an open configuration (see FIG. 41). The closure ring 226 can be caused to move between the opened and closed position by actuation of the closure tube 212. As the closure tube 212 is slid proximally and distally, the closure tube 212, which is engaged with the closure ring 226, causes the closure ring 226 to also slide proximally and distally, thereby opening and closing the anvil 152. The anvil 152 can be biased in an open configuration (see FIG. 41) with a series of springs 172 (see FIG. 35).

The closure tube 212 can be actuated by movement of a closure yoke 250 between an open position in which the anvil 152 is opened and a closed position in which the anvil 152 is closed. The closure yoke 250 can slide axially in a proximal direction to open the anvil 152 and slide axially in a distal direction to cause the anvil 152 to close. In other words, when the closure yoke 250 is in the open position it will be more proximal, and when the closure yoke 250 is in the closed position it will be more distal. As will be described in greater detail herein, the closure yoke 250 can be transitioned between the open and closed positions by actuation of several gears.

Closure Subsystem

Figure 7A:
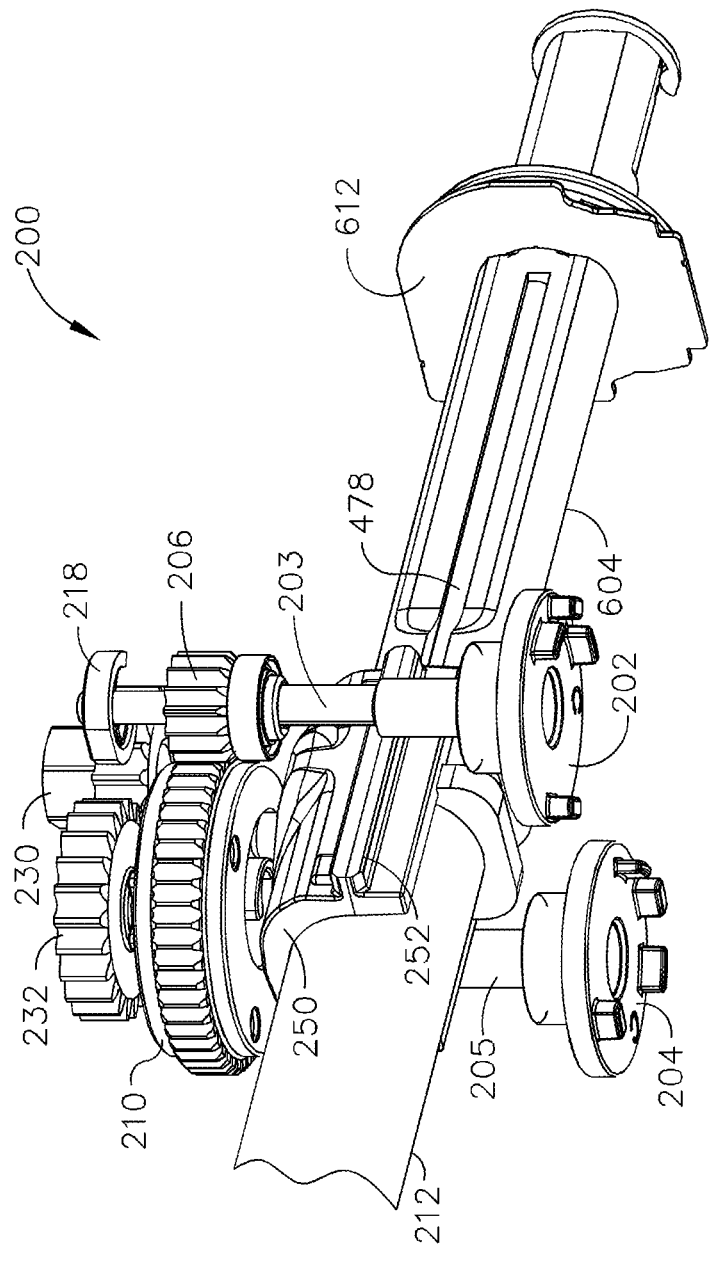
FIG. 7A shows a side perspective view of a closure subsystem, according to aspects of the present disclosure.
Figures 8, 9:
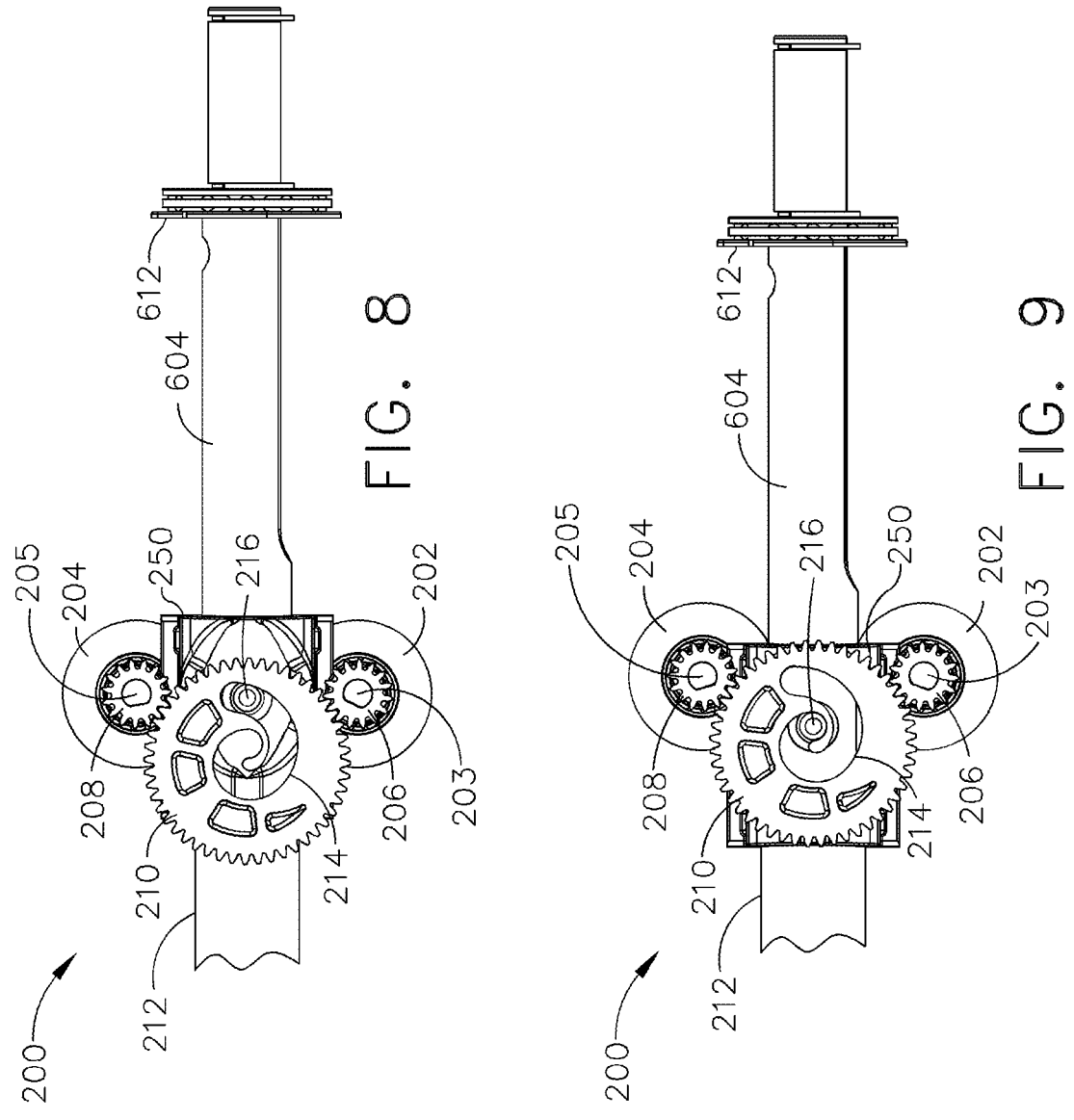
FIGS. 8 and 9 show a top plan view of a closure subsystem, according to aspects of the present disclosure.

Referring now to the closure subsystem 200, FIG. 7A provides a perspective view of the subsystem and FIGS. 8 and 9 provide side views of the subsystem. The closure subsystem 200 includes a first closure input puck 202 and a second closure input puck 204. The first closure input puck 202 is configured to engage with a first rotating feature of the robotic arm (e.g., first closure robotic output 902 in FIG. 2) and the second closure input puck 204 is configured to engage with a second rotating feature of the robotic arm (e.g., second closure robotic output 904 in FIG. 2). In this way, the robotic arm can be configured to transmit a greater amount of torque to the closure subsystem 200 to cause the anvil 152 to open or close than would be possible with only a single input puck. Robotic arm 1000 is also shown in the schematic of FIG. 2.

The first closure input puck 202 can be coupled to a first closure input rod 203 that extends into the outer housing 102. The first closure input rod 203 can be further coupled to a first closure spur gear 206. Thus, when the first closure input puck 202 rotates, it will also cause the first closure input rod 203 and the first closure spur gear 206 to rotate. Similarly, the second closure input puck 204 can be coupled to a second closure input rod 205 that extends into the outer housing 102. The second closure input rod 205 can be further coupled to a second closure spur gear 208. Thus, when the second closure input puck 204 rotates, it will also cause its corresponding second closure input rod 205 and the second closure spur gear 208 to rotate. The first closure input rod 203 can be held in place by a first retention clip 218 and the second closure input rod 205 can be held in place by a second retention clip 220.

Figure 39:
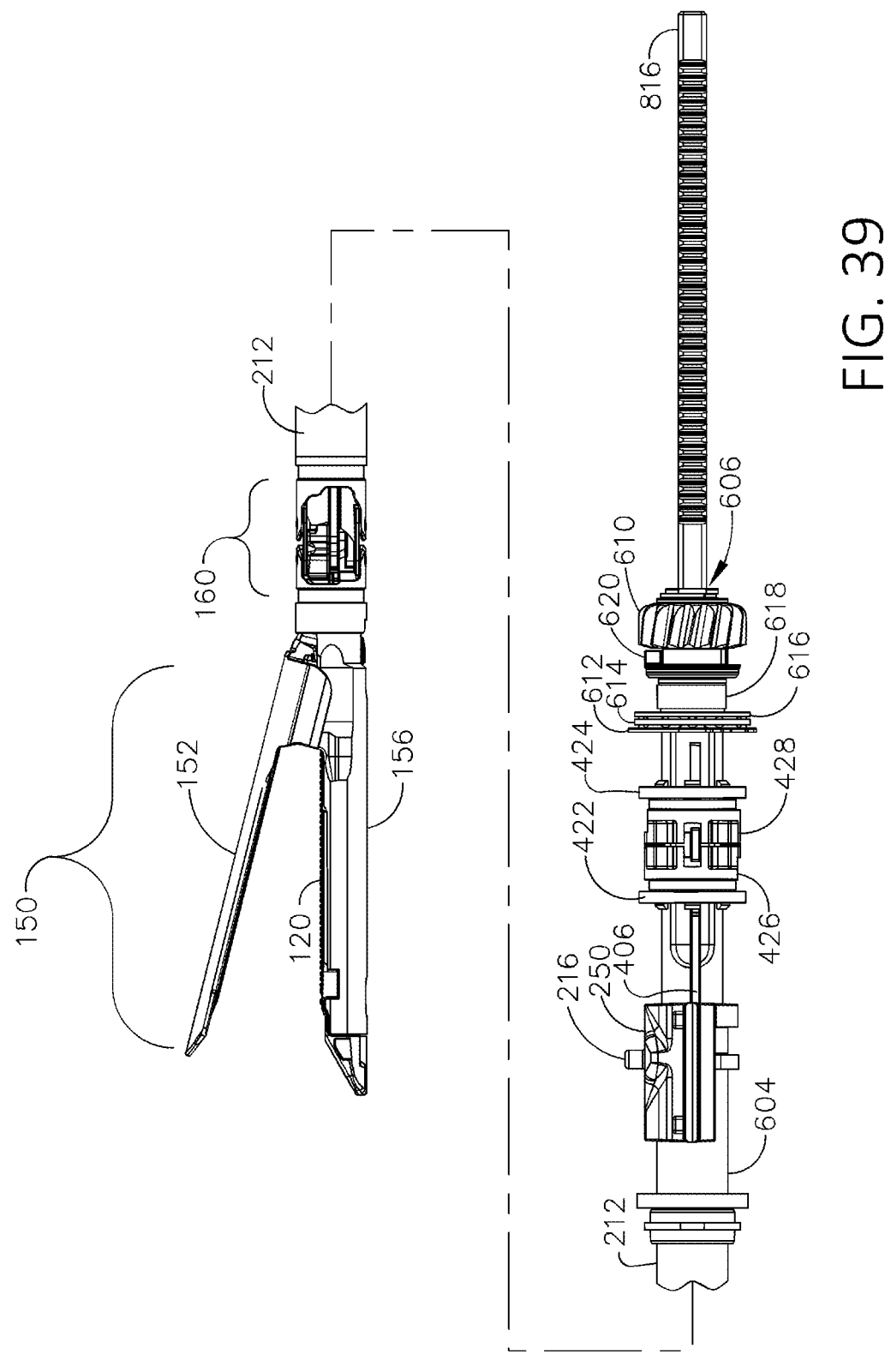
FIG. 39 shows shaft closure components of a surgical instrument with an anvil in an open position, according to aspects of the present disclosure.
Figure 40:
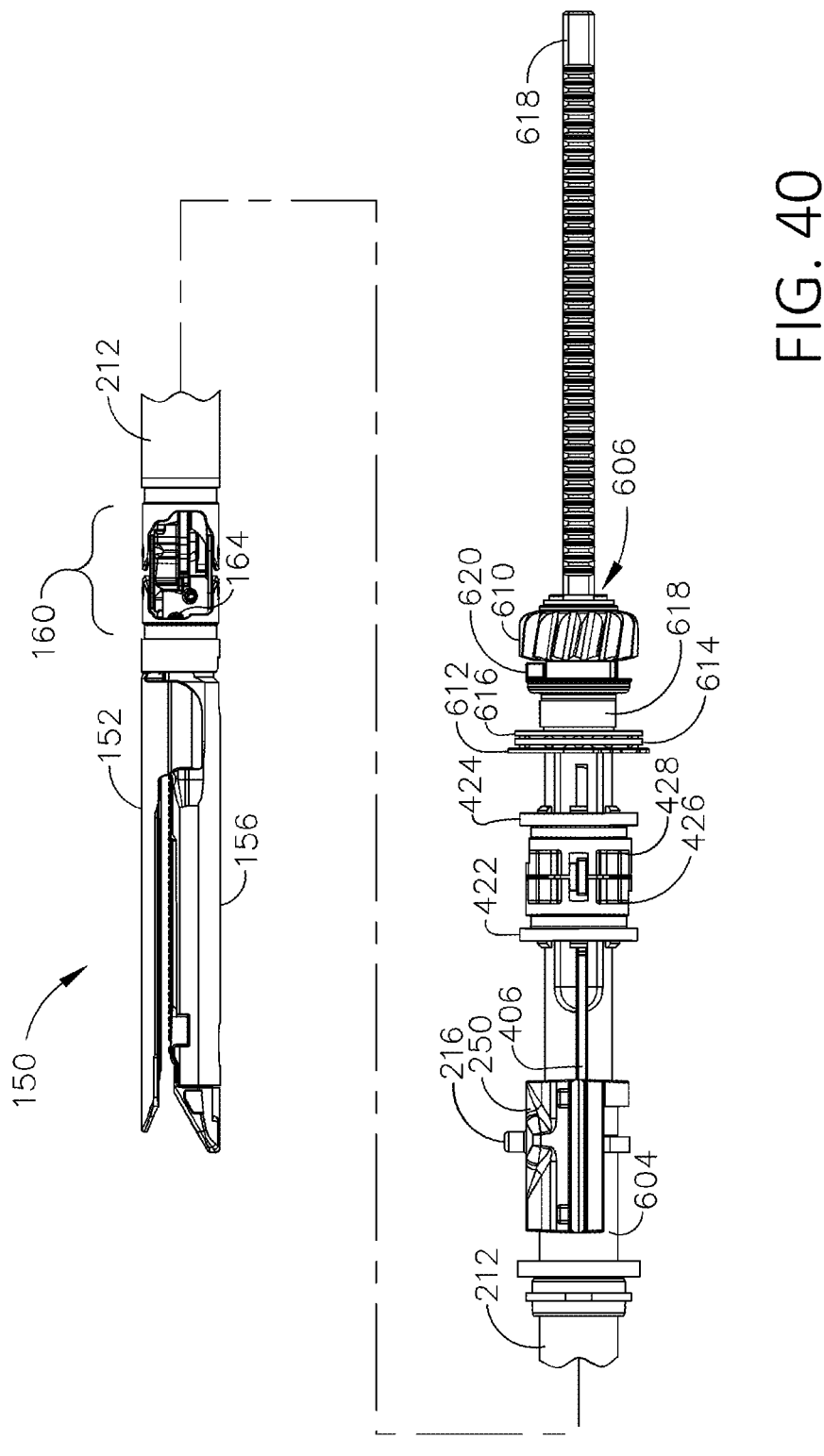
FIG. 40 shows shaft closure components of a surgical instrument with an anvil in a closed position, according to aspects of the present disclosure.

The first closure spur gear 206 and the second closure spur gear 208 can each be rotationally engaged with a closure cam gear 210. As shown in FIGS. 8 and 9, the closure cam gear 210 includes a cam track 214 that receives a yoke pin 216 that can be coupled to the closure yoke 250. As the closure cam gear 210 rotates, the cam track 214 can cause the yoke pin 216 to slide proximally and distally, thereby causing the closure yoke 250 to slide proximally and distally. In other words, as the closure cam gear 210 is rotated in a first direction, the cam track 214 will guide the yoke pin 216 along the cam track 214 in either the proximal or distal direction. Because the yoke pin 216 is coupled to the closure yoke 250, movement of the yoke pin 216 proximally or distally causes the closure yoke 250 to move proximally or distally. As explained previously, movement of the closure yoke 250 causes the anvil 152 to open or close via the closure tube 212. FIG. 39 shows the anvil 152 in an open configuration and the closure yoke 250 is positioned more proximally, and FIG. 40 shows the anvil 152 in a closed configuration where the closure yoke 250 has slid more distally. The closure yoke 250 can have a wing 252 (see FIGS. 7A and 36) extending therefrom that can track through a corresponding track in the housing 102 to allow the closure yoke 250 to translate proximally and distally but not rotate.

The cam track 214 can be a non-linear track that is configured to have changing movement profile as the closure cam gear 210 rotates. The cam track 214 is highlighted in detail in FIG. 10A, which shows a top view of the cam track 214 with an example non-linear profile. In some implementations, the cam track 214 can be a logarithmic spiral. The cam track 214 is not necessarily fully logarithmic, and in some instances can be represented by higher order polynomials, as some implementations can include a portion that is non-linear, a portion that has a constant radius, and a portion that connects the non-linear and constant radius portions. These different portions can be created by splines. One novel aspect of this non-linear cam track 214 design is that it can be shaped such that once the yoke pin 216 reaches a portion of the cam track 214 with a constant radius, the closure cam gear 210 rotates but the yoke pin 216 does not move axially. This feature can provide benefits by accounting for, and providing tolerance for, robotic inaccuracies.

Figure 10A:
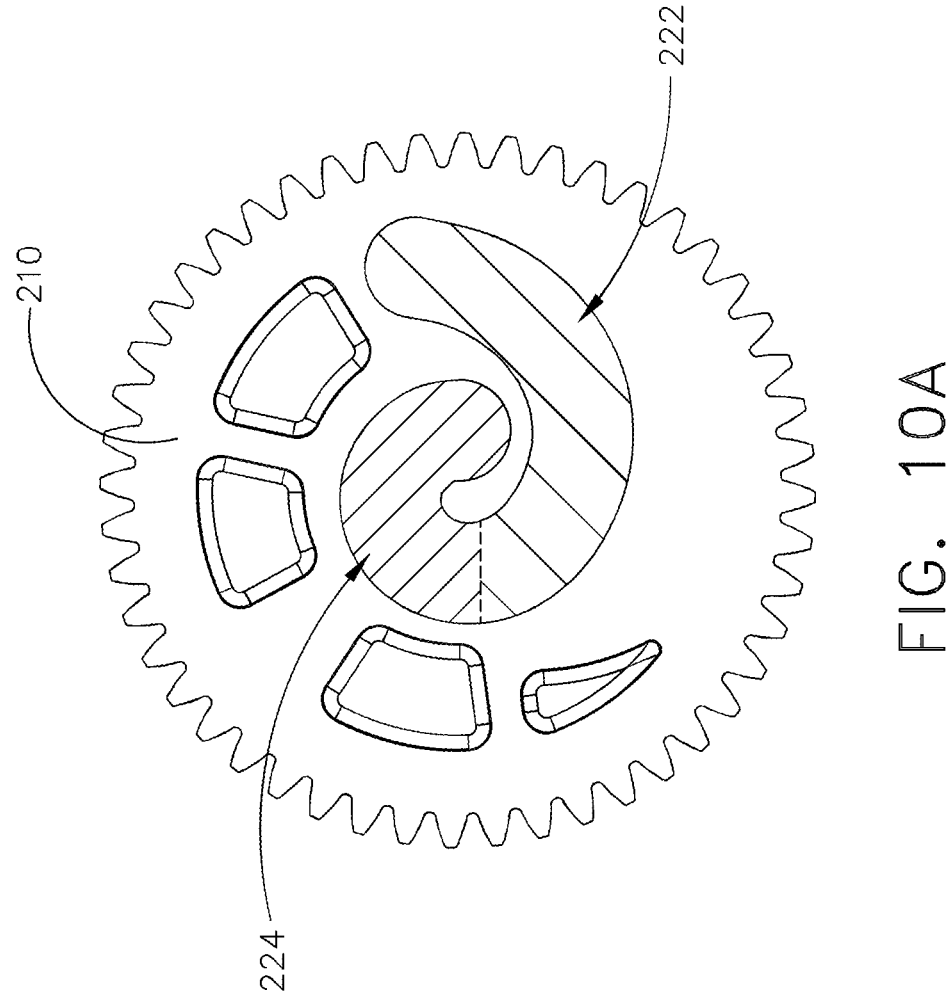
FIG. 10A is a top view of a closure cam gear, according to aspects of the present disclosure.

Continuing to refer to the closure cam gear 210 shown in FIG. 10A, the cam track 214 can include a first zone 222 and a second zone 224. The first zone 222 of the cam track 214 can be configured to cause the move the yoke pin 216 such that the anvil 152 compresses tissue without a great amount of force. The second zone 224 of the cam track 214, on the other hand, can be configured to cause the anvil 152 to compress tissue with a force sufficient to keep the tissue in place within the end effector 150 for cutting and/or stapling of the tissue. Furthermore, the slope of the cam track 214 at the first zone 222 and the second zone 224 can be varied to affect the speed and force with which the anvil 152 opens and closes. This change in speed and force therefore can be altered all while the speed of the input pucks 202, 204 remains the same. It will be understood that the cam track 214 is contiguous, non-linear, and smooth, so FIG. 10A depicting the different "zones" is not to indicate that there is a break or discontinuity in certain sections of the cam track 214. FIG. 8 shows a fully open configuration, where the yoke pin 216 is at a position within the cam track 214 such that the anvil 152 is fully open, thereby maximizing the amount of tissue that can be placed in the jaws (e.g., anvil and channel) of the end effector 150. FIG. 9 shows a fully closed configuration, where the yoke pin 216 is within a constant radius portion of the cam track 214 (in this view the yoke pin 216 is also at the very end of the cam track 214). A fully closed configuration can indicate that the surgical instrument 100 is ready to proceed with firing (e.g., transection and/or stapling). Partially open configurations can exist between the examples shown in FIGS. 8 and 9 wherein the system can grasp tissue.

Figure 10B:
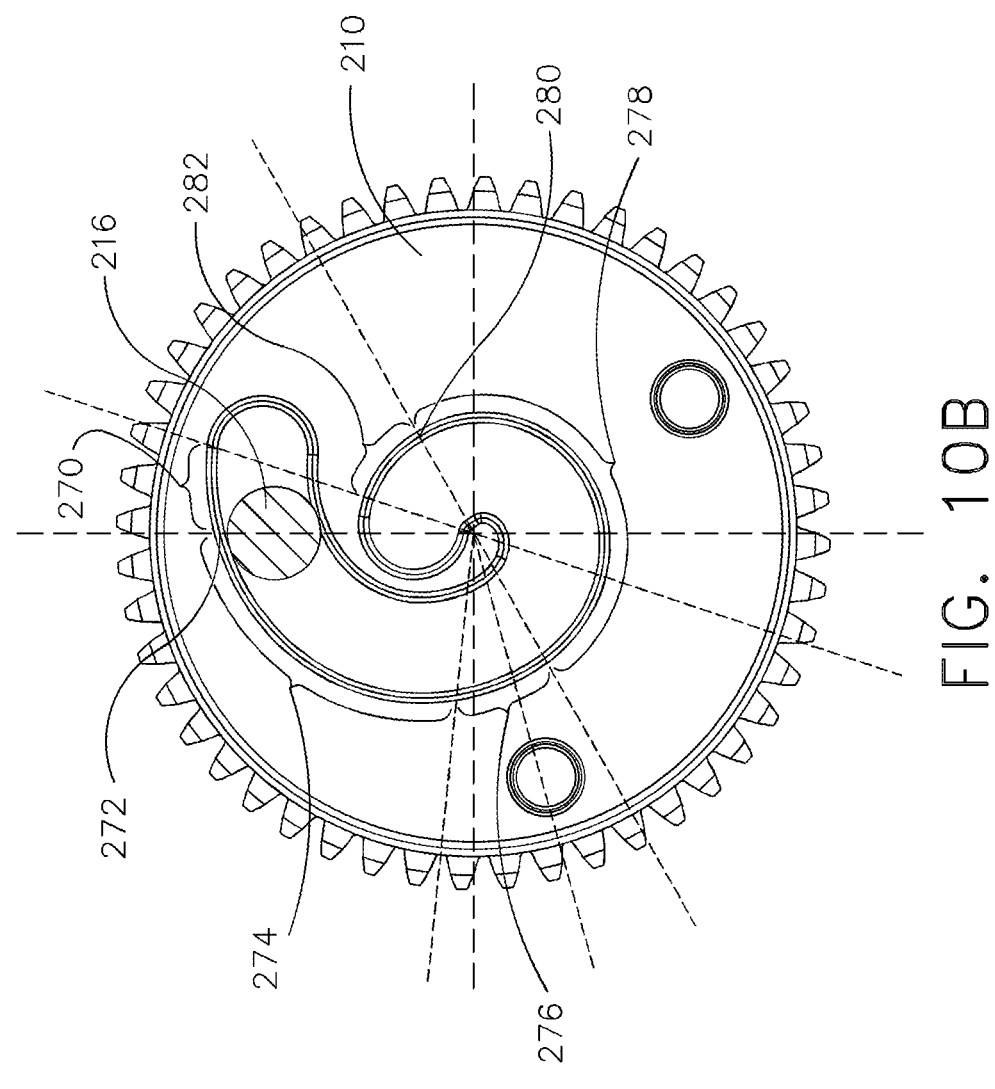
FIG. 10B is a bottom view of a closure cam gear, according to aspects of the present disclosure.

Referring now to FIG. 10B, which is a bottom view of the closure cam gear 210, the view shows different regions of the cam track 214 that can provide different movement profiles for the yoke pin 216. Referencing this view in FIG. 10B, as the closure cam gear 210 rotates clockwise, the yoke pin 216 translates downward in the view (downward being distally in relation to the shaft 604, see FIG. 7A). The regions of the cam track 214 can provide different movement profiles depending on where in the cam track 214 the yoke pin 216 is located. For example, the closure cam gear 210 in FIG. 10B has indications of degrees for reference, up being labeled 0°, left being labeled 90°, down being labeled 180°, and right being labeled 270°. The cam track 214 can include an open dead zone 270 that exists between around −20° and around 0°. The open dead zone 270 is a region beyond an open position 272 that provides a level of tolerance should the closure cam gear 210 be rotated beyond the open position 272. The open position 272, or home position, can be a hard stop position where the closure ring 226 is positioned proximally, allowing the anvil 152 to be fully open (see FIG. 39). The cam track 214 of FIG. 10B includes a high-speed compression region 274 positioned in the next portion of the cam track 214 beyond the open position 272. This high-speed compression region 274 can extend from around 0° to around 90°. The high-speed compression region 274 has a curvature that enables the yoke pin 216 to transition distally quickly while providing a low amount force (for example closing force on the anvil 152, see FIG. 39). At around 90° on the closure cam gear 210 of FIG. 10B is a force transition region 276. Extending beyond the force transition region 276 is a high force region 278. The high force region 278 can extend from around 90° to around 300° on the closure cam gear 210 of FIG. 10B. This region provides a low speed, high force movement profile for the distal movement of the yoke pin 216. The high force region 278, for example, can be a portion of the movement profile that begins to put a large amount of compression on the tissue that is being cut and/or stapled. At around 300° on the closure cam gear 210 of FIG. 10B is a closing target 280. Any point beyond the closing target 280 can be considered as "fully closed", as in the force and distal movement yoke pin 216 are considered met. Extending beyond the closing target 280, and from about 300° to the end of the cam track 214, is a constant force region 282. Like the constant radius portion described above, the constant force region 282 can be a section of the cam track 214 where the closure cam gear 210 rotates but the yoke pin 216 does not move axially. This can help to provide tolerance for any positional error by the robot (e.g., positional errors by the first closure robotic output 902 and/or second closure robotic output 904 in FIG. 2).

Figures 7B, 7C:
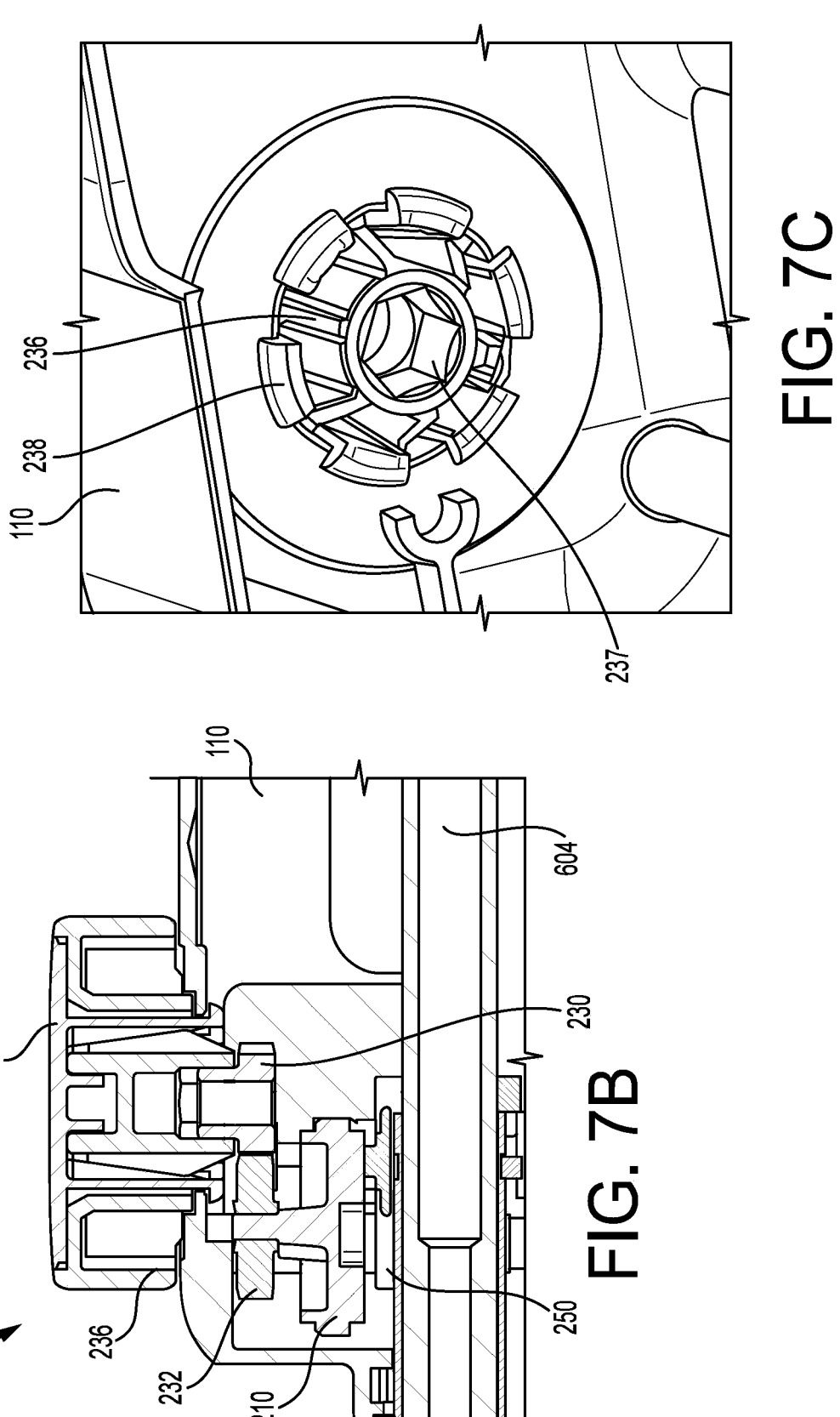
FIG. 7B is a cross-sectional view taken along the longitudinal axis of the surgical instrument and showing details of a manual closure handle, according to aspects of the present disclosure.
FIG. 7C is an underside perspective view of the manual closure handle, according to aspects of the present disclosure.
Figure 7E:
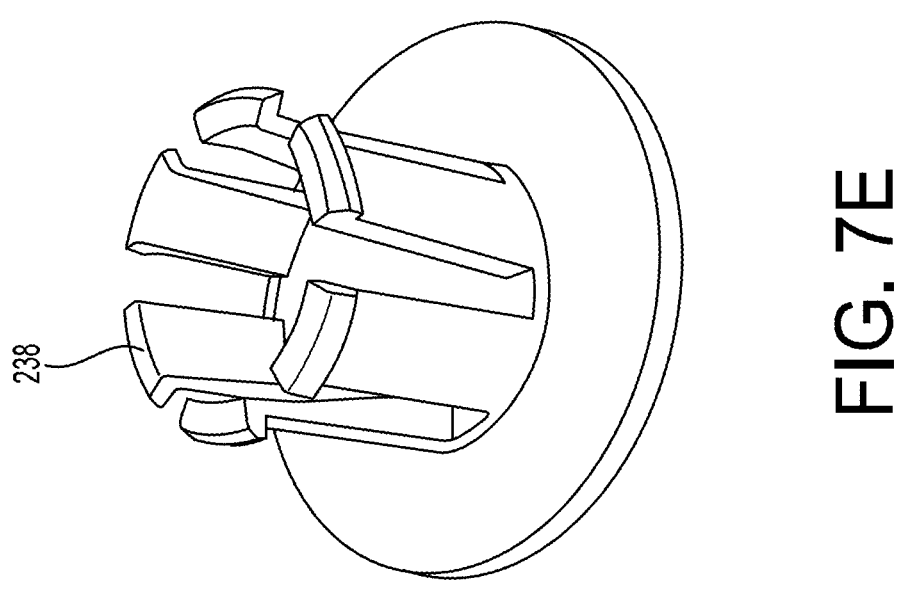
FIG. 7E is a detail view of a manual closure handle clip, according to aspects of the present disclosure.
Figure 7D:
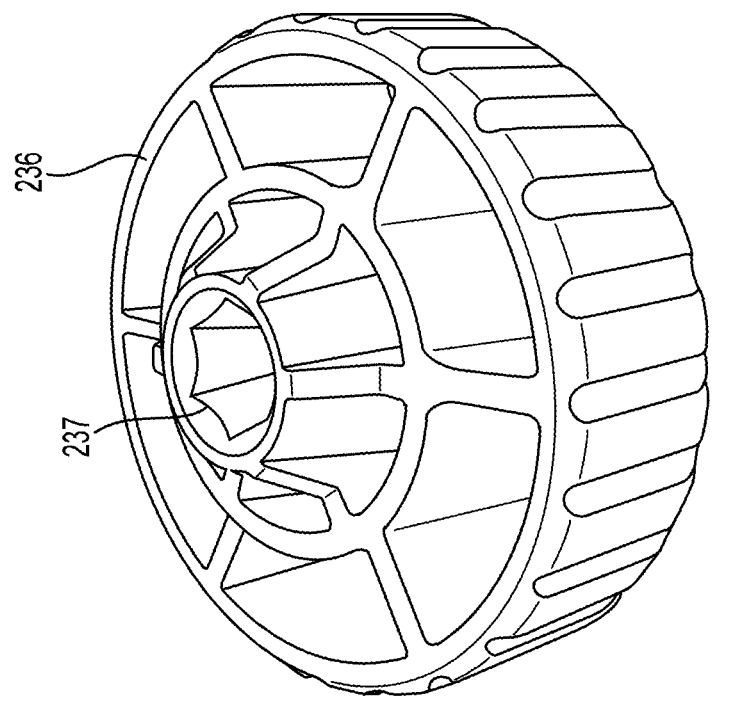
FIG. 7D is a detail view of a manual closure handle grip, according to aspects of the present disclosure.

The closure subsystem 200 can further include a manual closure spur gear 230 that is coupled to a manual closure handle 234 (as shown in FIGS. 7B and 7E-71) that extends through the outer housing 102. The manual closure handle 234 can be used, for example, by a surgical staff if the surgical robot is unable to open or close the anvil 152. The manual closure spur gear 230 can be rotationally coupled to a manual closure cam gear 232 that can be keyed to the closure cam gear 210. In this way, rotation of the manual closure handle 234 will cause the manual closure spur gear 230 and the manual closure cam gear 232 to rotate, thereby causing the closure cam gear 210 to rotate and open or close the anvil 152. As will be appreciated, the manual closure handle 234 provides a surgical staff with the ability to open and close the anvil 152 when the surgical instrument 100 is disconnected from a surgical robot or to override the opening or closing of the anvil 152 when connected to the surgical robot.

As shown in FIGS. 7E-71, the manual closure handle 234, in some examples, includes a manual closure handle grip 236 and a manual closure handle clip 238. The manual closure handle grip 236 can extend beyond an outer portion of the housing 102 such that the physician or surgical staff can grip the manual closure grip 236 and rotate it to cause the anvil 152 to open or close. The manual closure handle clip 238 can be configured to extend through the manual closure handle grip 236 and into the housing 102 to attached to the manual closure handle 234 to the housing 102. The manual closure handle clip 238 can include one or more protruding features that can snap into place when pushed into the housing 102 to attached to the manual closure handle 234 to the housing 102. In other examples, the manual closure handle grip 236 and the manual closure handle clip 238 can be integrated into a single component.

Figure 7F:
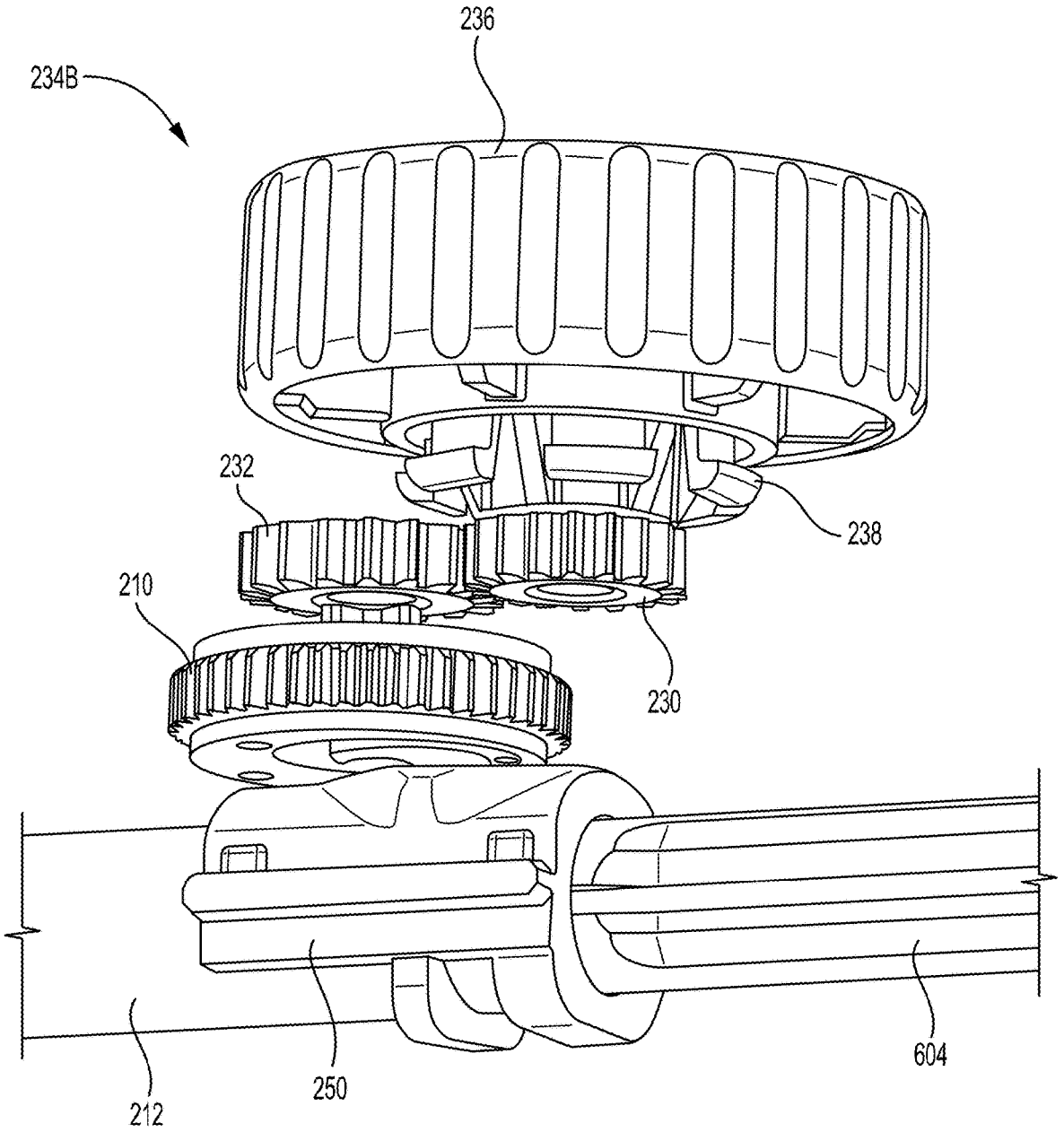
FIG. 7F is a detail view of the closure subsystem with manual closure handle, according to aspects of the present disclosure.

The manual closure handle grip 236 can attach to the manual closure spur gear 230 by, for example but not limitation, receiving a protrusion of the manual closure spur gear 230 into a recess formed into the manual closure handle grip 236 (as shown in FIGS. 7E and 7F). The manual closure handle grip 236 can include engagement surfaces 237 that can align with corresponding engagement surfaces of the manual closure spur gear 230 to transfer forces from the manual closure handle grip 236 to the manual closure spur gear 230 when rotated. For example, the protrusions of the manual closure spur gear 230 and the recess of the manual closure handle grip 236 can be a hex head or other similar features.

Although not shown, in some examples, the manual closure handle grip 236 could include geometry that limits the travel, or provides some resistance to the travel, of the manual closure handle grip 236 at predetermined locations such that the manual closure handle grip 236 is stopped or at least slowed at positions corresponding to desired positions of the opening and closing of the anvil 152. Alternatively, or in addition, the manual closure handle grip 236 or the manual closure handle clip 238 can include markings, colors, protrusions, recesses, etc. that indicate the position of the anvil 152. In some examples. The manual closure handle grip 236 or the manual closure handle clip 238 can include transparent features that reveal indicators at certain positions of rotation to indicate the status. Furthermore, the manual closure handle 230 and/or the closure subassembly 200 can include torque limiting features to prevent over torquing of the closure subassembly 200.

Articulation Subsystem

Figure 11:
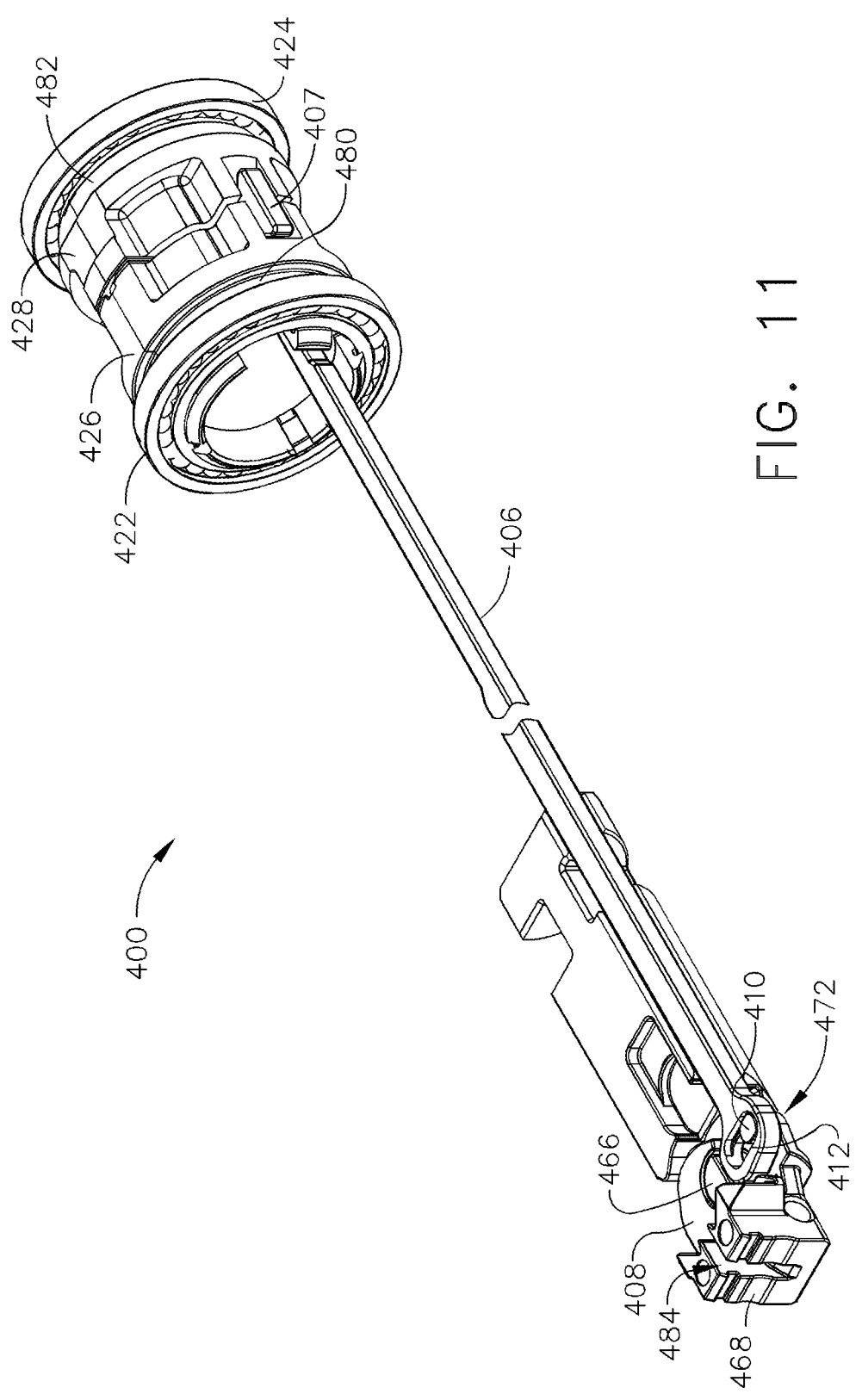
FIG. 11 shows components of an articulation subsystem, according to aspects of the present disclosure.
Figure 25:
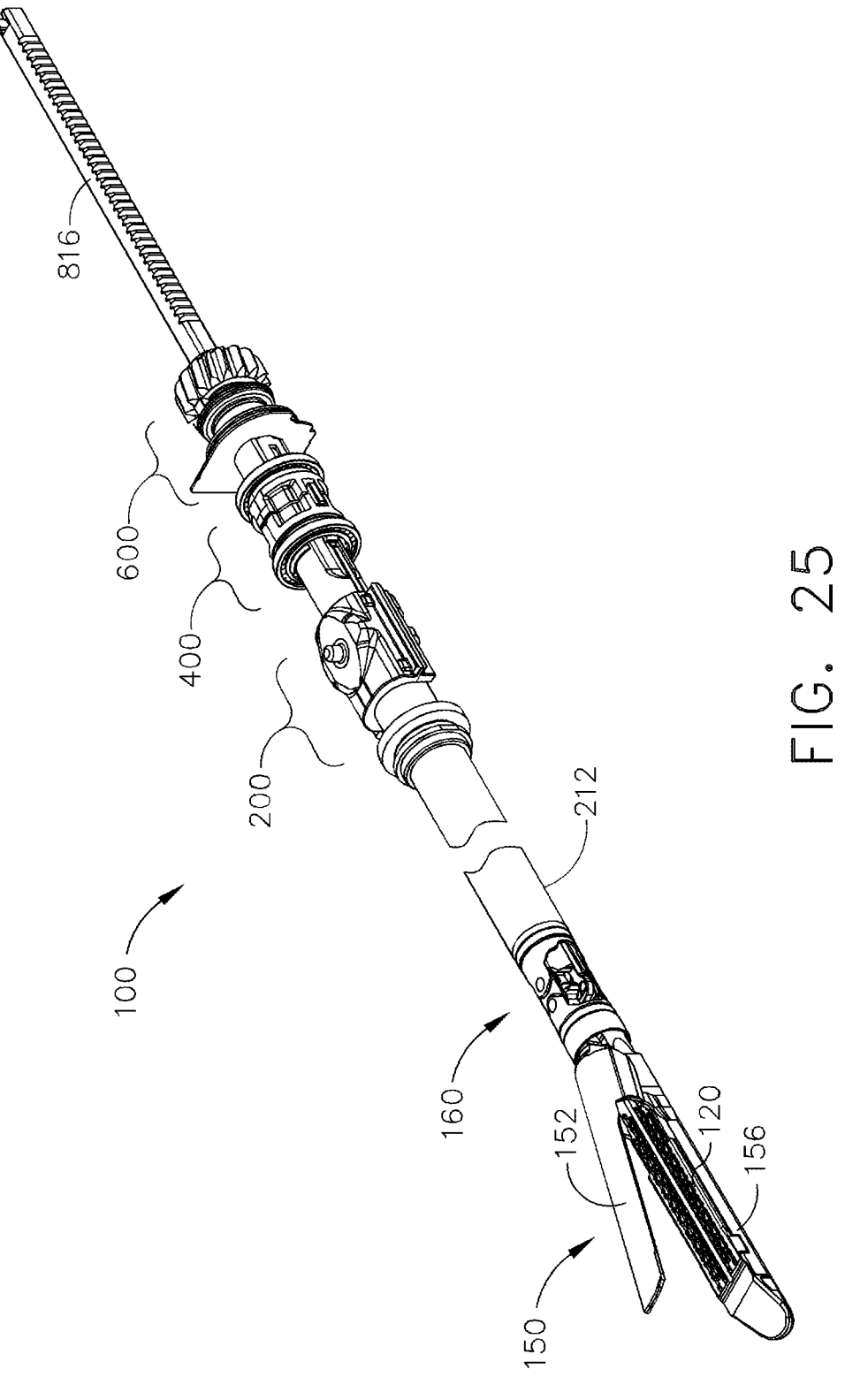
FIG. 25 shows components of a surgical instrument with an anvil of an end effector being open, according to aspects of the present disclosure.

The surgical instrument 100 includes an articulation subsystem 400. Detailed views of the proximal portions of an example articulation subsystem 400 are provided in FIGS. 11-19. Views of the articulation of the distal end of the surgical instrument 100 are shown in FIGS. 20-24. FIGS. 25 and 36 provide perspective views of the articulating portion of the distal end of the surgical instrument 100. Referring specifically to FIG. 11, the articulation subsystem 400 includes an articulation rod 406 extending distally to a distal channel retainer 408. The proximal end 470 of the articulation rod 406 can include an attachment 407 that constrains the articulation rod proximally (e.g., to a first articulation bushing 426 and a second articulation bushing 428). The attachment can be a hook, as shown in FIG. 11, or it can be a loop with pin 507 as shown in FIG. 16. The distal end 472 of the articulation rod 406 can be connected to a distal channel retainer 408 that can pivot back and forth (e.g., left and right) to move, or articulate, an end effector 150 of the surgical instrument 100. An attachment end 468 of the distal channel retainer 408 can, for example, be attached to a channel 156 of the end effector 150 to articulate the end effector 150. The attachment end 468 can also include a band slot 484 for a series of bands 826 to pass through, which are described in greater detail herein with respect to the transection subsystem 800.

Figure 38:
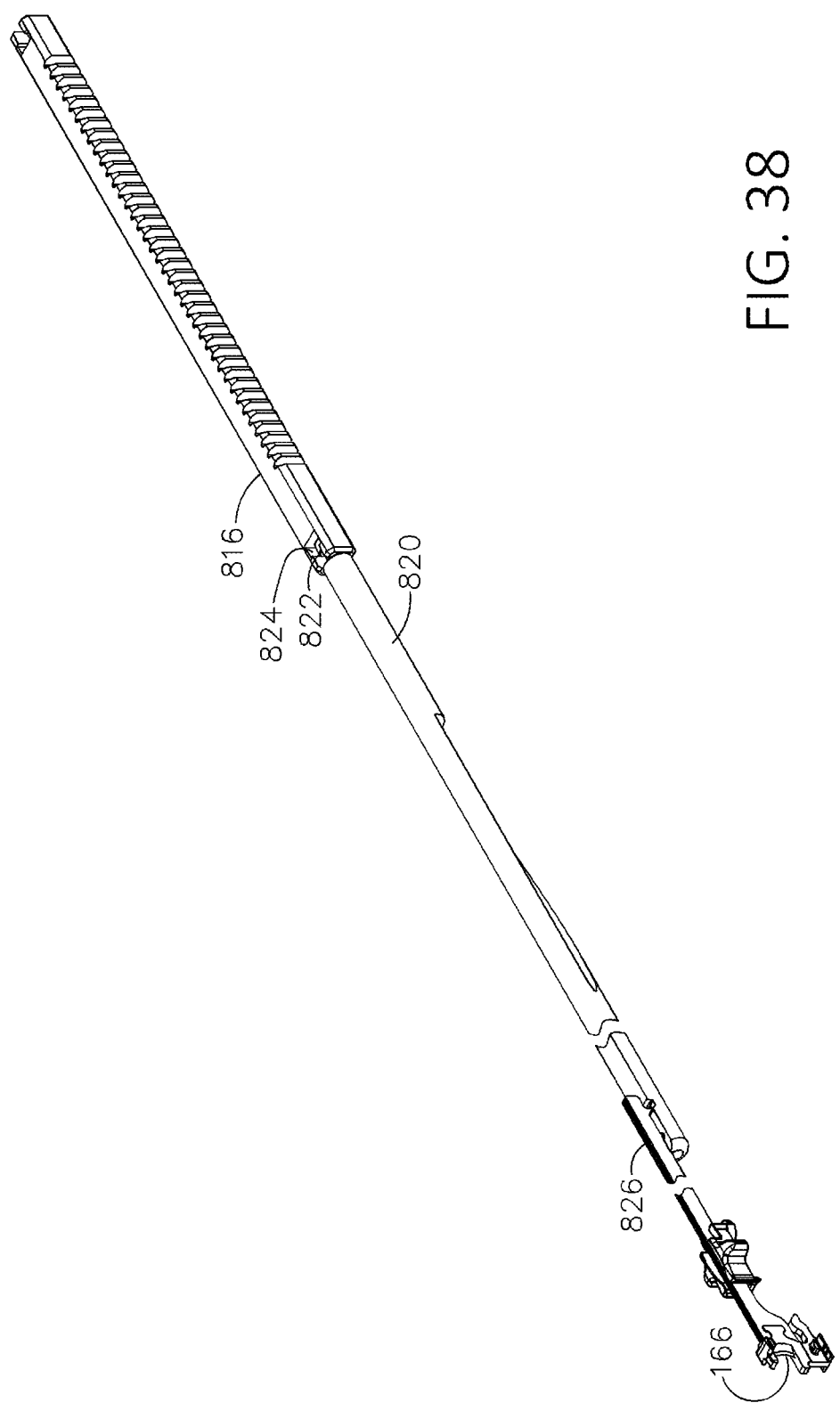
FIG. 38 shows shaft transection (e.g., firing) components of a surgical instrument, according to aspects of the present disclosure.

Referring again to the distal channel retainer 408 shown in FIG. 11, the articulation rod 406 can articulate the distal channel retainer 408 back and forth about an articulation joint 466 by pushing and pulling one side of the distal channel retainer 408. To do so, the distal channel retainer 408 can include a retainer pin 410, and the articulation rod 406 can have a rod aperture 412 distally that engages the retainer pin 410. As the articulation rod 406 translates distally, the articulation rod 406 pushes the retainer pin 410 distally and thus articulates the distal channel retainer 408 about the articulation joint 466 in one direction, and as the articulation rod 406 translates proximally, the articulation rod 406 pulls the retainer pin 410 proximally and thus articulates the distal channel retainer 408 about the articulation joint 466 in the opposite direction. The rod aperture 412 can be oblong, as shown in FIG. 11, to account for the translation of the retainer pin 410 laterally as the distal channel retainer 408 rotates, since the articulation rod 406 moves only axially and is constrained to the shaft 604 within a rod groove 478. FIGS. 38 and 40 show a view of the rod groove 478 along the length of the shaft 604.

Figure 12:
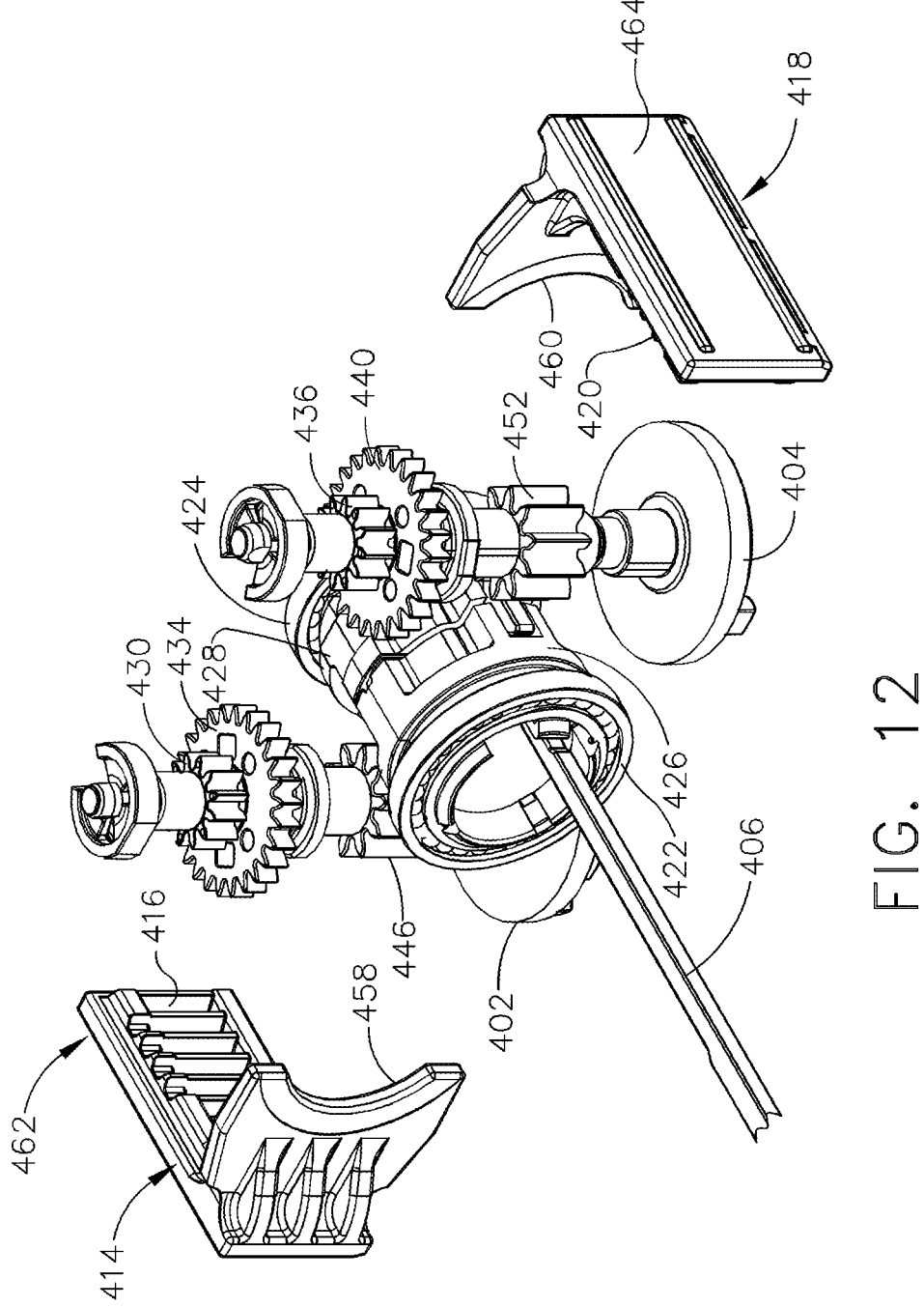
FIG. 12 is a partially exploded view of an articulation subsystem having an "outboard" configuration, according to aspects of the present disclosure.

Referring now to FIG. 12, which is a partially exploded view of the proximal portions of the articulation subsystem 400, the articulation subsystem 400 includes features that accommodate the roll functions of the surgical instrument 100. As will be described in greater detail below with respect to the roll subsystem 600, the surgical instrument 100 includes a shaft 604 that can roll, i.e., rotate back and forth, to improve the access to a transection site. To elaborate, the shaft 604 can be directly connected to the end effector 150, and therefore the combination of rolling of the shaft 604 (via the roll subsystem 600) and articulating the end effector 150 (via the articulation subsystem 400) enables the end effector 150 to articulate with more degrees of freedom than simply left to right by pivoting the distal channel retainer 408. The articulation rod 406 extends along the rotatable shaft 604, for example within the rod groove 478. To account for the ability of the articulation rod 406 to rotate with the shaft 604, the articulation subsystem 400 includes one or more bushings (compare FIG. 12 and FIG. 16) that allow the rotatable robotic outputs to move the articulation subsystem 400 proximally and distally (for example to move the articulation rod 406) along the shaft 604, while also allowing the shaft 604 to rotate within the articulation subsystem 400. The articulation subsystem 400 of FIGS. 12-15 includes a first rack 414 that can be moved via a series of gearing by rotation of the first articulation input puck 402, the puck 402 being engageable with a corresponding rotatable robotic output (e.g., first articulation robotic output 906 in FIG. 2). Robotic arm 1000 is also shown in the schematic of FIG. 2. The inside of the first rack 414 includes rack gearing 416 that facilitates axial translation of the first rack 414 (e.g., distal and proximal within the outer housing 102). The articulation subsystem 400 includes a second rack 418 that can be moved via a series of gearing by rotation of the second articulation input puck 404, the puck 404 being engageable with a corresponding rotatable robotic output (e.g., second articulation robotic output 908 in FIG. 2). Robotic arm 1000 is also shown in the schematic of FIG. 2. The inside of the second rack 418 includes rack gearing 420 that enables axial translation of the second rack 418 (e.g., distal and proximal within the outer housing 102).

To account for the rotation of the shaft 604, the articulation subsystem 400 of FIGS. 12-15 can include a first articulation bushing 426 that is rotatable with the shaft 604, and is rotatably independent of the first rack 414. In other words, the rolling of the shaft 604 will also roll the first articulation bushing 426, all while the first rack 414 remains rotationally stable within the outer housing 102. The first articulation bushing 426 can slide from a first position to a second position along a longitudinal axis 474 of the rotatable shaft 604, thereby moving the articulation rod 406 proximally and distally. The first rack 414 can have a first housing track surface 462 that moves axially within a corresponding track in the outer housing 102, thereby enabling the first rack 414 to slide axially but not rotationally. The first housing track surface 462 and the first bearing surface 458 can be at 90° with respect to each other. The articulation subsystem 400 of FIGS. 12-15 includes a second articulation bushing 428 that is rotatable with the shaft 604, and is rotatably independent of the second rack 418. In other words, the rolling of the shaft 604 will also roll the second articulation bushing 428, all while the second rack 418 remains rotationally stable within the outer housing 102. The second articulation bushing 428 can slide from a first position to a second position along the longitudinal axis 474 of the rotatable shaft 604, thereby moving the articulation rod 406 proximally and distally. The second rack 418 can have a second housing track surface 464 that moves axially within a corresponding track in the outer housing 102, thereby enabling the second rack 418 to slide axially but not rotationally. The second housing track surface 464 and the second bearing surface 460 can be at 90° with respect to each other.

Figure 13:
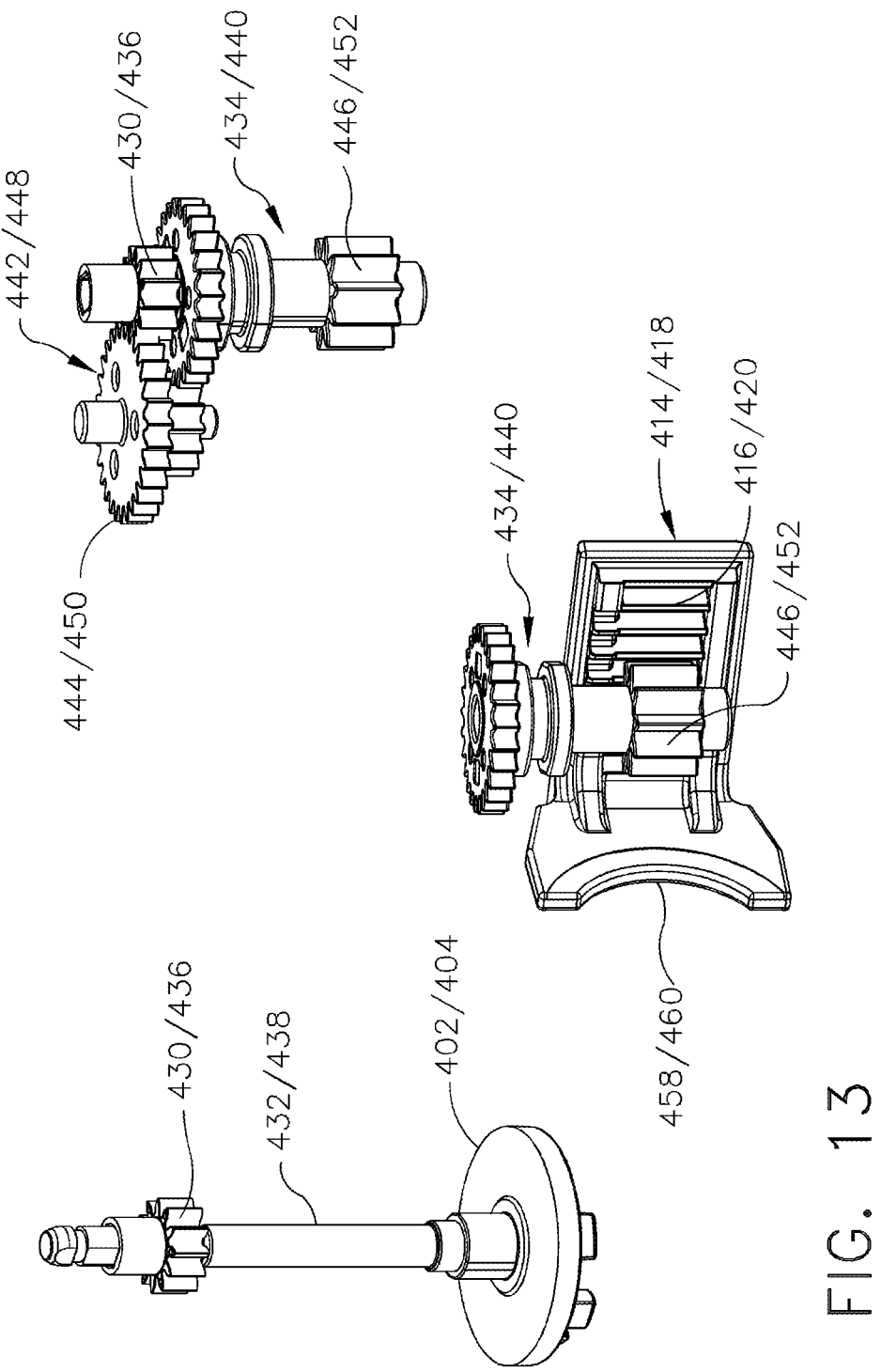
FIG. 13 is an exploded view of gears of an articulation subsystem having an "outboard" configuration, according to aspects of the present disclosure.

Turning now to FIGS. 12 and 13 to describe the gearing of the example articulation subsystem 400, the subsystem includes a first articulation drive shaft 432 extending from the first articulation input puck 402 and including a first drive gear 430. Rotation of the first articulation input puck 402 by the corresponding robotic output can therefore rotate the first drive gear 430. The articulation subsystem 400 includes a first rack gear 434, which can in some instances be a hollow tube gear that slides over the first articulation drive shaft 432, thereby providing a mechanical advantage to the system while also conserving space within the outer housing 102. The first rack gear 434 can be rotatably coupled to the first articulation drive shaft 432 by means of a first compound gear 442 (see FIGS. 5 and 13) that has stepped teeth 444, one portion of the stepped teeth 444 being engaged with the first drive gear 430, and the other portion of the stepped teeth 444 being engaged with the first rack gear 434. As such, rotation of the first articulation drive shaft 432 rotates the first drive gear 430, rotation of the first drive gear 430 rotates the first compound gear 442, and rotation of the first compound gear 442 rotates the first rack gear 434 that is surrounding the first articulation drive shaft 432. Further, the first rack gear 434 includes first rack gear teeth 446 that engage with the rack gearing 416 of the first rack 414. Rotation of the first rack gear 434 therefore causes the first rack 414 to translate proximally and distally to move the first articulation bushing 426.

Similarly, the subsystem can include a second articulation drive shaft 438 extending from the second articulation input puck 404 and including a second drive gear 436. Rotation of the second articulation input puck 404 by the corresponding robotic output can therefore rotate the second drive gear 436. The articulation subsystem 400 can include a second rack gear 440, which can in some instances be hollow a tube gear that slides over the second articulation drive shaft 438. The second rack gear 440 can be rotatably coupled to the second articulation drive shaft 438 by means of a second compound gear 448 that has stepped teeth 450 (see FIGS. 5 and 13), one portion of the stepped teeth 450 being engaged with the second drive gear 436, and the other portion of the stepped teeth 450 being engaged with the second rack gear 440. As such, rotation of the second articulation drive shaft 438 rotates the second drive gear 436, rotation of the second drive gear 436 rotates the second compound gear 448, and rotation of the second compound gear 448 rotates the second rack gear 440 that is surrounding the second articulation drive shaft 438. Further, the second rack gear 440 includes second rack gear teeth 452 that engage with the rack gearing 420 of the second rack 418. Rotation of the second rack gear 440 therefore causes the second rack 418 to translate proximally and distally to move the second articulation bushing 428.

Referring again to the articulation bushings and racks of FIGS. 12-15, the first rack 414 can engage with the first articulation bushing 426 in a manner that enables proximal or distal movement of the first articulation bushing 426, while the first articulation bushing 426 remains able to rotate with the shaft 604. The first rack 414 includes a first bearing surface 458 that abuts the first articulation bushing 426. The first articulation bushing 426 can include a first rack groove 480 around the perimeter of the bushing into which the first bearing surface 458 extends. As the first articulation bushing 426 rotates, the first bearing surface 458 can track through the first rack groove 480. As such, the first bearing surface 458 can be semicircular. Similarly, the second rack 418 can engage with the second articulation bushing 428 in a manner that enables proximal or distal movement of the second articulation bushing 428, while the second articulation bushing 428 remains able to rotate with the shaft 604. The second rack 418 can include a second bearing surface 460 that abuts the second articulation bushing 428. The second articulation bushing 428 can include a second rack groove 482 around the perimeter of the bushing into which the second bearing surface 460 extends. As the second articulation bushing 428 rotates, the second bearing surface 460 can track through the second rack groove 482. As such, the second bearing surface 460 can be semicircular. To enable the bushings to rotate freely while remaining stable within the outer housing 102, the articulation subsystem 400 can include a first articulation bearing 422 around the first articulation bushing 426, and the articulation subsystem 400 can include a second articulation bearing 424 around the second articulation bushing 428.

Figures 14, 15:
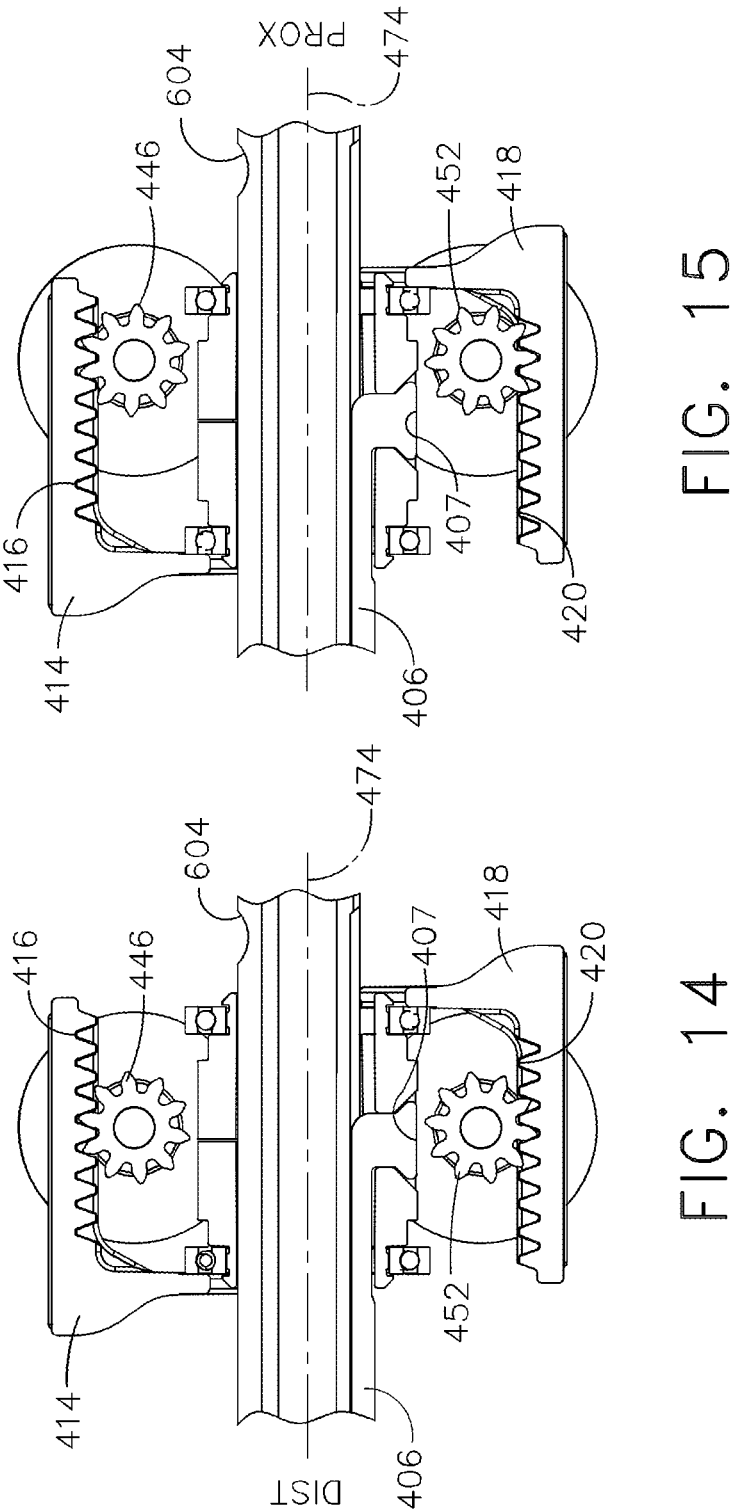
FIGS. 14 and 15 are top views of components of an articulation subsystem having an "outboard" configuration, according to aspects of the present disclosure.
Figure 16:
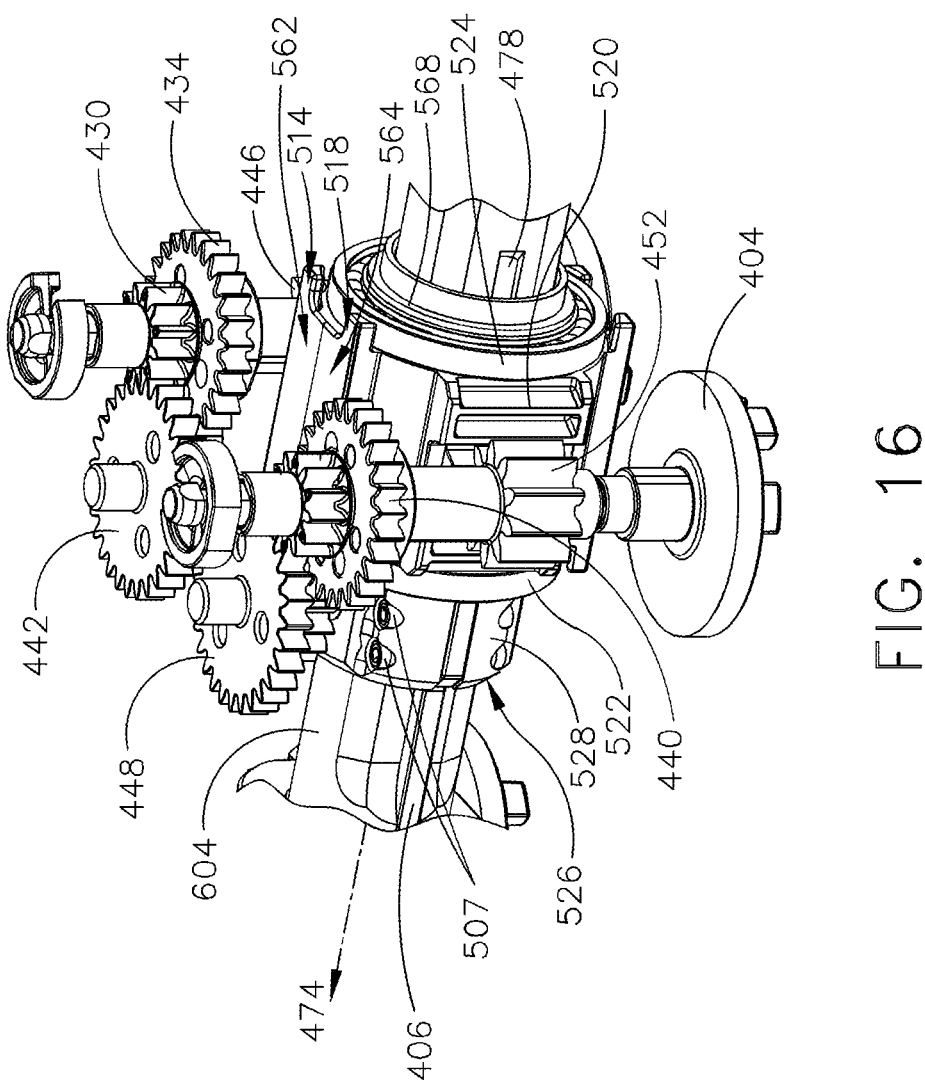
FIG. 16 is a perspective view of an articulation subsystem in an "inboard" configuration, according to aspects of the present disclosure.
Figure 17:
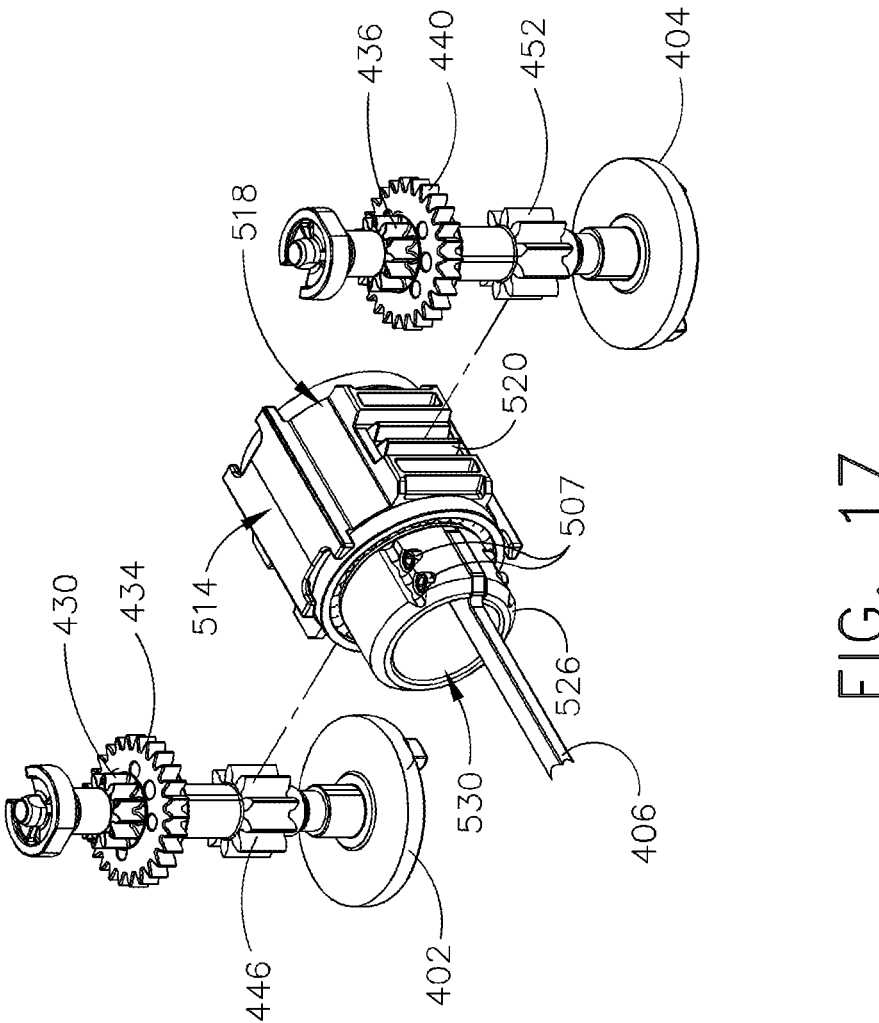
FIG. 17 is a partially exploded view of an articulation subsystem having an "inboard" configuration, according to aspects of the present disclosure.

Referring now to FIGS. 14 and 15 specifically, the two figures show the actuation of the articulation subsystem 400 by movement of the first rack 414 and the second rack 418. FIG. 14 shows an articulation subsystem 400 at a neutral, e.g., 0° state, of articulation. To move the first articulation bushing 426, the first rack gear 434 can rotate in a first angular direction, and the first rack gear teeth 446 move through the first rack gearing 416 of the first rack 414. FIG. 15 shows where the first rack gear 434 (i.e., the first rack gear teeth 446) has rotated in counterclockwise direction to move the first rack 414 distally. Movement of the first rack 414 distally causes the first articulation bushing 426 to translate distally along the longitudinal axis 474 of the shaft 604. In turn, the articulation rod 406 will translate distally, thereby pivoting the distal channel retainer 408 such that the end effector 150 pivots, in this example to the right. In the same example shown in FIG. 15, the second rack gear 440 (i.e., the second rack gear teeth 452) has rotated in clockwise direction to move the second rack 418 distally. Movement of the second rack 418 distally causes the second articulation bushing 428 to translate distally along the longitudinal axis 474 of the shaft 604. If the rack gears 434, 440 are rotated in the opposite directions, the articulation bushings 426, 428 will move proximally along the longitudinal axis 474 of the shaft 604, thereby pulling the articulation rod 406 and causing the end effector to pivot, or articulate, in the other direction.

The example articulation subsystem 400 shown with respect to FIGS. 12-15 could be called an "outboard" configuration, wherein in the racks 414, 418 are external to the gearing mechanisms that move the racks 414, 418 along longitudinal axis 474 of the rotatable shaft 604. To illustrate further, in FIG. 12, the first rack gear 434 is positioned between the first rack 414 and the rotatable shaft 604 (see shaft in FIG. 14); the second rack gear 440 is positioned between the second rack 418 and the rotatable shaft 604. FIGS. 16-19 show an alternative design that could be called an "inboard" configuration. Here, the one or more racks 514, 518 are positioned internal to the respective rack gears 434, 440. Referring now to the design shown in FIG. 16 specifically, the articulation subsystem 400 shown therein includes a first rack 514 that can be moved, via a series of gearing, by rotation of the first articulation input puck 402, the puck 402 being engageable with a corresponding rotatable robotic output (e.g., first articulation robotic output 906 in FIG. 2). The outside surface of the first rack 514 includes rack gearing 516 (see in FIG. 18) that facilitates axial translation of the first rack 514 (e.g., distal and proximal along the shaft 604). The articulation subsystem 400 can include a second rack 518 that can be moved, via a series of gearing, by rotation of the second articulation input puck 404, the puck 404 being engageable with a corresponding rotatable robotic output (e.g., second articulation robotic output 908 in FIG. 2). The outside surface of the second rack 518 includes rack gearing 520 that enables axial translation of the second rack 518 (e.g., distal and proximal along the shaft 604). When two separate racks, i.e., the first rack 514 and the second rack 518, are present, the two racks abut lengthwise to form a hollow cylinder with the lumen 530 extending therethrough.

Figure 43A:
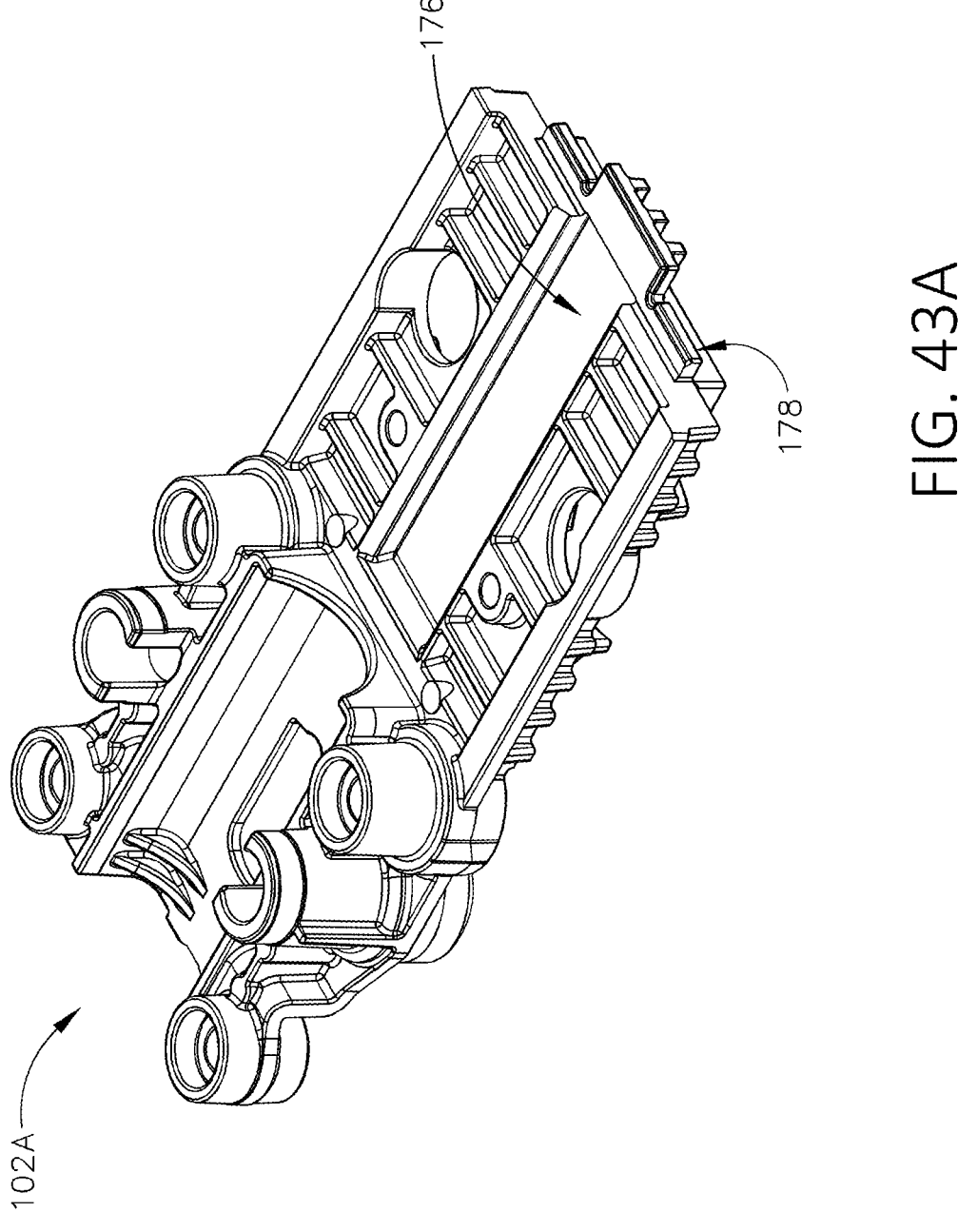
FIG. 43A shows components and features of a housing or an intermediate housing, according to aspects of the present disclosure.
Figure 43B:
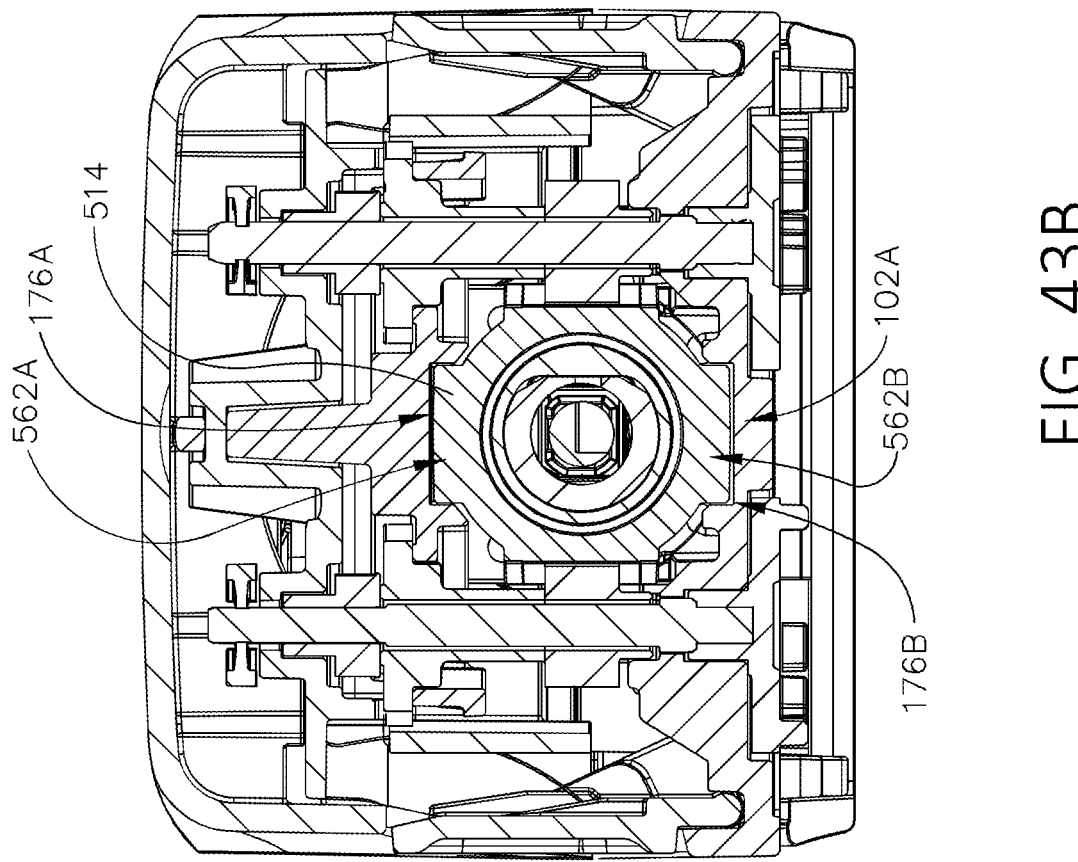
FIG. 43B shows components and features of a housing, according to aspects of the present disclosure.

FIGS. 43A and 43B show how the one or more racks 514, 518 can interact with the housing and/or intermediate housings. As mentioned above, the rack system in the "inboard" implementation can have two racks 514, 518 abutting each other, or in a preferred embodiment can include a single rack 514 with a lumen extending therethrough, the articulation bushing 526 being positioned within the bushing. FIG. 43B shows the example of a single rack 514 with a first housing track surface 562A at the top and a first housing track surface 562B at the bottom. Referring now to the feature shown in FIG. 43A, the figure depicts an intermediate housing 102A, which can be an insert positioned without an outer shell of the housing 102. The intermediate housing 102A can add additional structural support to the components of the subsystems of the surgical instrument 100. FIG. 43A shows a position of a buttress 178 that can provide structural support for transection and/or roll subsections of the surgical instrument 100. FIG. 43A in particular highlights a track 176 that will accept portions of the racks 514 (e.g., first housing track surface 562 and/or second housing track surface 564 discussed with respect to FIG. 18) such that the one or more racks 514, 518 can translate proximally and distally with respect to the housing 102. FIG. 43B is a cross sectional view showing the interaction of the rack 514 and the track 176. FIG. 43B shows two tracks, an upper track 176A and a lower track 176B corresponding to the with an upper housing track surface 562A and lower housing track surface 562B.

Although FIG. 16 shows two separate racks (i.e., the first rack 514 and the second rack 518, as noted by the line shown lengthwise), it is contemplated and, in most instances, preferred that the entire rack system could be a singular bushing that is slid onto a first articulation bushing (described below as first articulation bushing 526). In this case, there would only be a "first rack" (e.g., first rack 514) in the embodiment, with a lumen 530 (see FIG. 17) extending therethrough to engage with the first articulation bushing 526. In this implementation, the outside surface of the first rack 514 includes rack gearing 520 that enables axial translation of the first rack 514 (e.g., distal and proximal along the shaft 604); the rack gearing 520 being positioned opposite the first rack gearing 516. An example of this implementation with a single rack 518 is shown in the cross-sectional view of FIG. 43B.

Figures 18, 19:
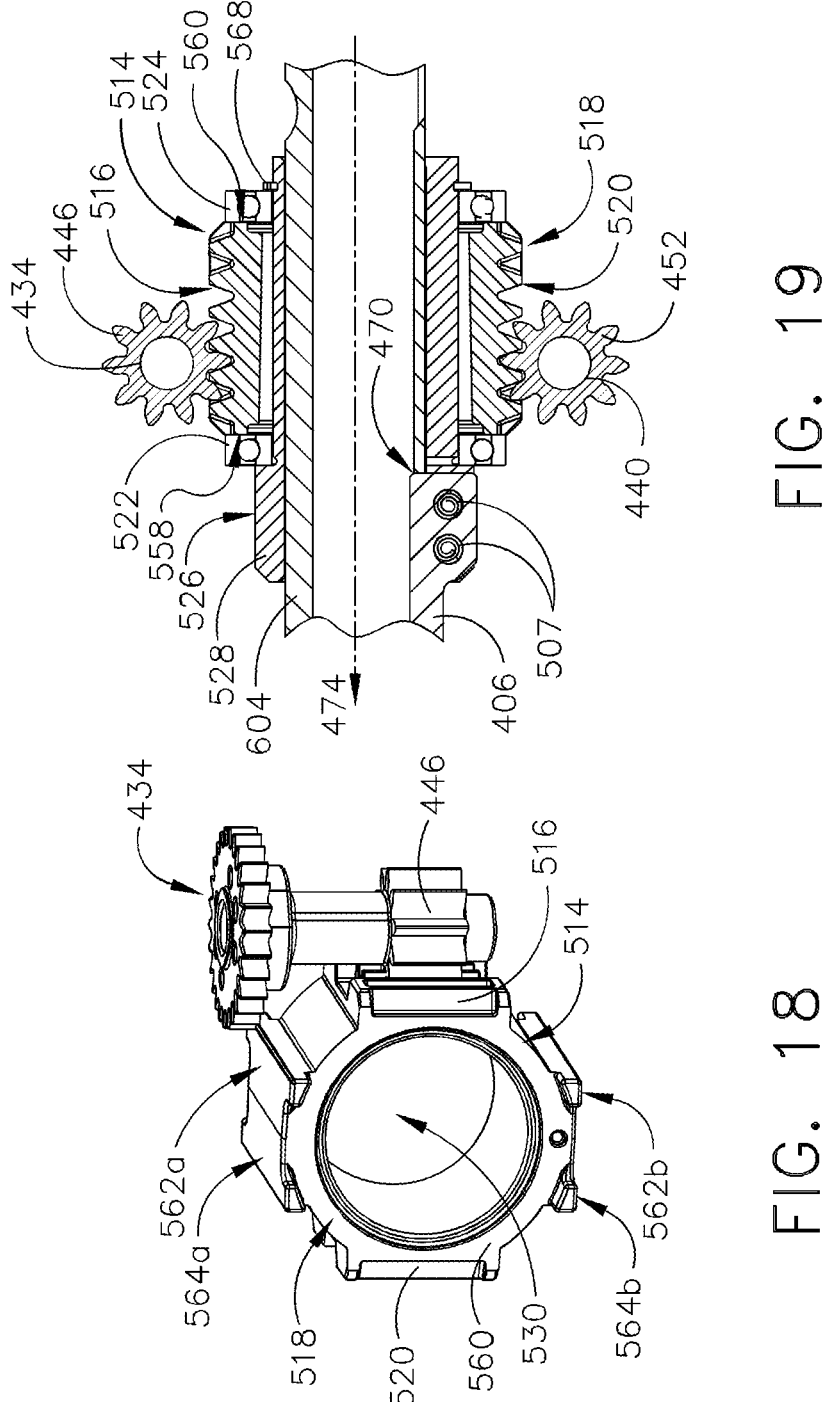
FIG. 18 is a perspective view of a portion of an "inboard" articulation subsystem, according to aspects of the present disclosure.
FIG. 19 is a top cross-sectional view of an "inboard" articulation subsystem, according to aspects of the present disclosure.

To account for the rotation of the shaft 604, the articulation subsystem 400 shown in FIG. 16 includes a first articulation bushing 526 that is rotatable with the shaft 604, and is rotatably independent of the first rack 514 (and second rack 518 if present). In other words, the rolling of the shaft 604 will also roll the first articulation bushing 526, all while the first rack 514 remains rotationally stable within the outer housing 102. The first articulation bushing 526 can slide from a first position to a second position along a longitudinal axis 474 of the rotatable shaft 604, thereby moving the articulation rod 406 proximally and distally. The first rack 514 can have a first housing track surface 562 that moves axially within a corresponding track in the outer housing 102, thereby enabling the first rack 514 to slide axially but not rotationally. If a second rack 518 is present, the second rack 518 can have a first housing track surface 564 adjacent the first housing rack surface 562 that moves axially within a corresponding track in the outer housing 102, thereby enabling the second rack 518 to slide axially but not rotationally. FIGS. 43A and 43B show the tracks 176A, 176B through which the rack 514 can track. As shown, both tops and bottoms of the first rack 514 can have a first housing track surface 562, which are shown in FIG. 18 labeled as first housing track surfaces 562*a* and 562*b*. If a second rack 518 is present, both tops and bottoms of the second rack 518 can have a second housing track surface 564, which are shown in FIG. 18 labeled as second housing track surfaces 564*a* and 564*b*. Again, these track surfaces 562 and/or 564 can travel within the housing 102 (see again FIGS. 43A and 43B).

Unlike in the "outboard" design shown in FIGS. 12-15, the example shown in FIGS. 16-19 show only a single first articulation bushing 526. The shape of this first articulation bushing 526 is best shown in the cross section of FIG. 19. The first articulation bushing 526 is slid onto the shaft 604. The first rack 514 (and the second rack 518 if present) is secured with respect to the first articulation bushing 526 via a first articulation bearing 522 and a second articulation bearing 524. The first articulation bearing 522 is constrained distally by a flange 528, and the second articulation bearing 524 is constrained proximally by a locking ring 568. Constrained as such, movement of the first rack 514 and/or the second rack 518 can cause the first articulation bushing 526 to move axially, as described herein. The distal end of the first rack 514 (and the second rack 518) has a first bearing surface 558 that abuts the flange 528, and the proximal end of the first rack 514 (and the second rack 518) has a second bearing surface 560. As can be seen in FIG. 19, the one or more racks 514, 518 themselves do not need to touch the first articulation bushing 526, and decoupling the one or more racks 514, 518 from the first articulation bushing 526 can reduce wear on those parts. Instead, the one or more racks 514, 518 can contact the respective bearings 522, 524, and the bearings 522, 524 contact the first articulation bushing 526.

Regarding the relative movement of the rack gears 434, 440 and the respective racks for each design, the movement of the rack gears 434, 440 (or initially the movement of the first articulation input puck 402 and/or second articulation input puck 404 that results in the movement of the rack gears) can be used to share load and/or create antagonistic compression at the bushings. To illustrate using the views in FIGS. 14 and 15, or the "outboard" configuration, the surgical instrument 100 can create antagonistic compression of the articulation bushings 426, 428. For example, the rack gears 434, 440 can maintain a force that causes compression of the articulation bushings 426, 428 towards each other. Maintaining this antagonistic compression can reduce lash between the rack gear teeth 446, 452 and the respective rack gearing 416, 420. In FIGS. 16-19, or the "inboard" configuration, the first rack 514 and the second rack 518 share loads and do not act antagonistically. However, that does not preclude the example shown in FIGS. 16-19 from using antagonistic options to reduce lash or, in some examples, allow one of the two pucks to act as an articulation brake by counteracting the torque of the other puck.

The proximal end 470 of the articulation rod 406 can include a hook 407 or other attachment that constrains the articulation rod 406 proximally between the articulation bushings 426, 428, as shown in FIGS. 12-15. In other examples, the proximal end 470 of the articulation rod 406 can be coupled to the first articulation bushing 526 via one or more pins 507 (see FIG. 19). The pins 507 can attach the articulation rod 406 to the flange 528. As mentioned above with respect to the outboard configuration, the inboard configuration is designed such that movement of the first articulation bushing 526 effects articulation of the end effector 150 (see FIGS. 22-24). FIG. 19 shows how articulation of the rack gears 434, 440 can impart a force onto the individual racks 514, 518 to move the first articulation bushing 526. To move the first articulation bushing 526, the first rack gear 434 can rotate in a first angular direction, and the first rack gear teeth 446 move through the first rack gearing 516 of the first rack 514. Movement of the first rack 514 distally (by first rack gear 434 turning clockwise in FIG. 19) causes the first articulation bushing 426 to translate distally along the longitudinal axis 474 of the shaft 604. In turn, the articulation rod 406 will translate distally, thereby pivoting the distal channel retainer 408 such that the end effector 150 pivots, in this example to the right. The first rack gear 434 can rotate in a second angular direction (opposite the first angular direction described above), and the first rack gear teeth 446 move through the first rack gearing 516 of the first rack 514. In turn, the articulation rod 406 will translate proximally, thereby pivoting the distal channel retainer 408 such that the end effector 150 pivots, in this example to the left. When the second rack 518 and second rack gear 440 are employed, rotation will be opposite of the first rack 514 and first rack gear 434. For example, if the first rack gear 434 rotates clockwise to move the first rack 514 distally, the second rack gear 440 rotates counterclockwise to move the second rack 518 distally. In this example, therefore, the first rack gear 434 and the second rack gear 440 act to share the load, providing a greater articulation force for the end effector 150.

Figure 20:
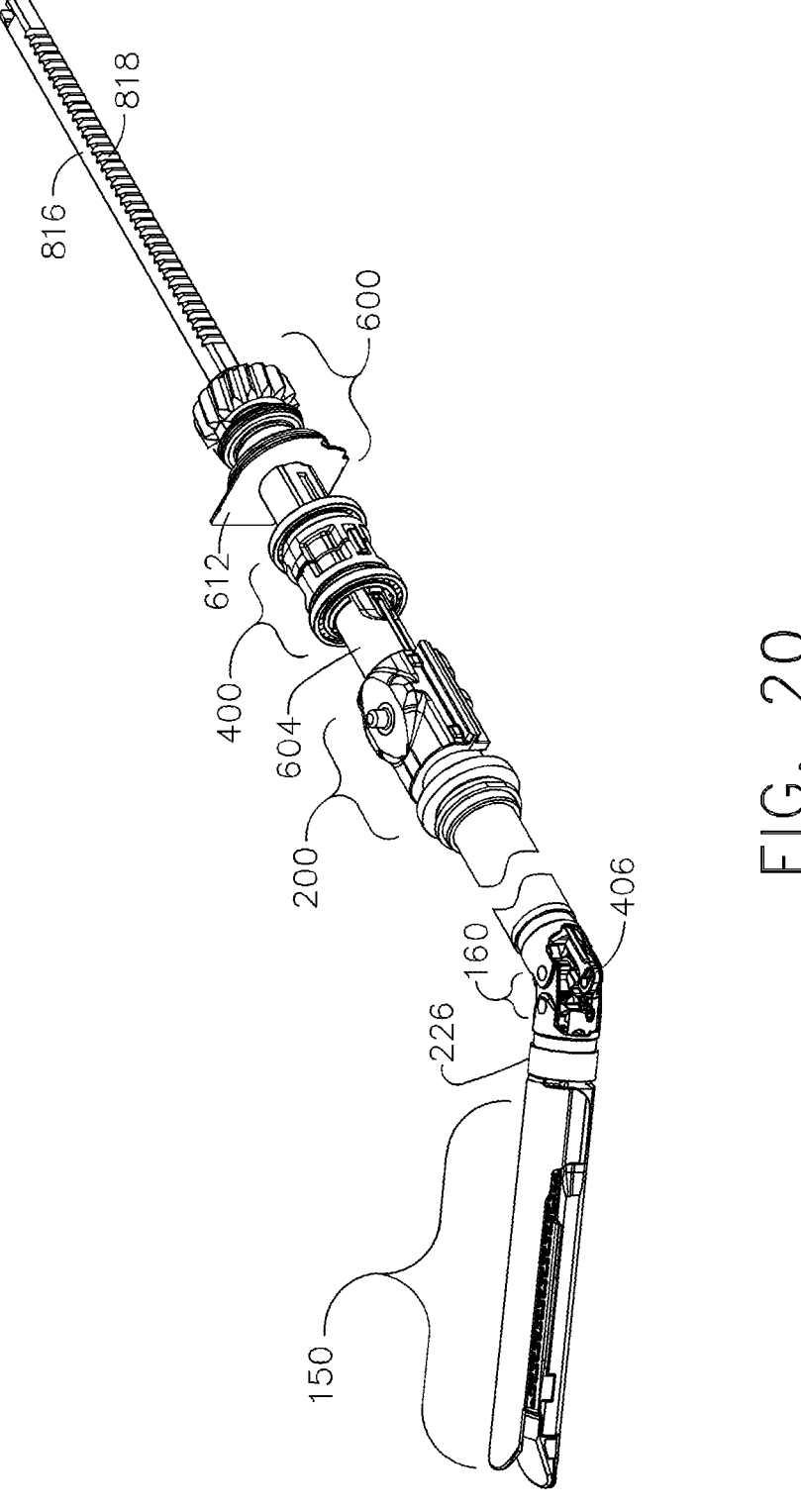
FIG. 20 shows components of a surgical instrument with an end effector being articulated, according to aspects of the present disclosure.
Figure 21:
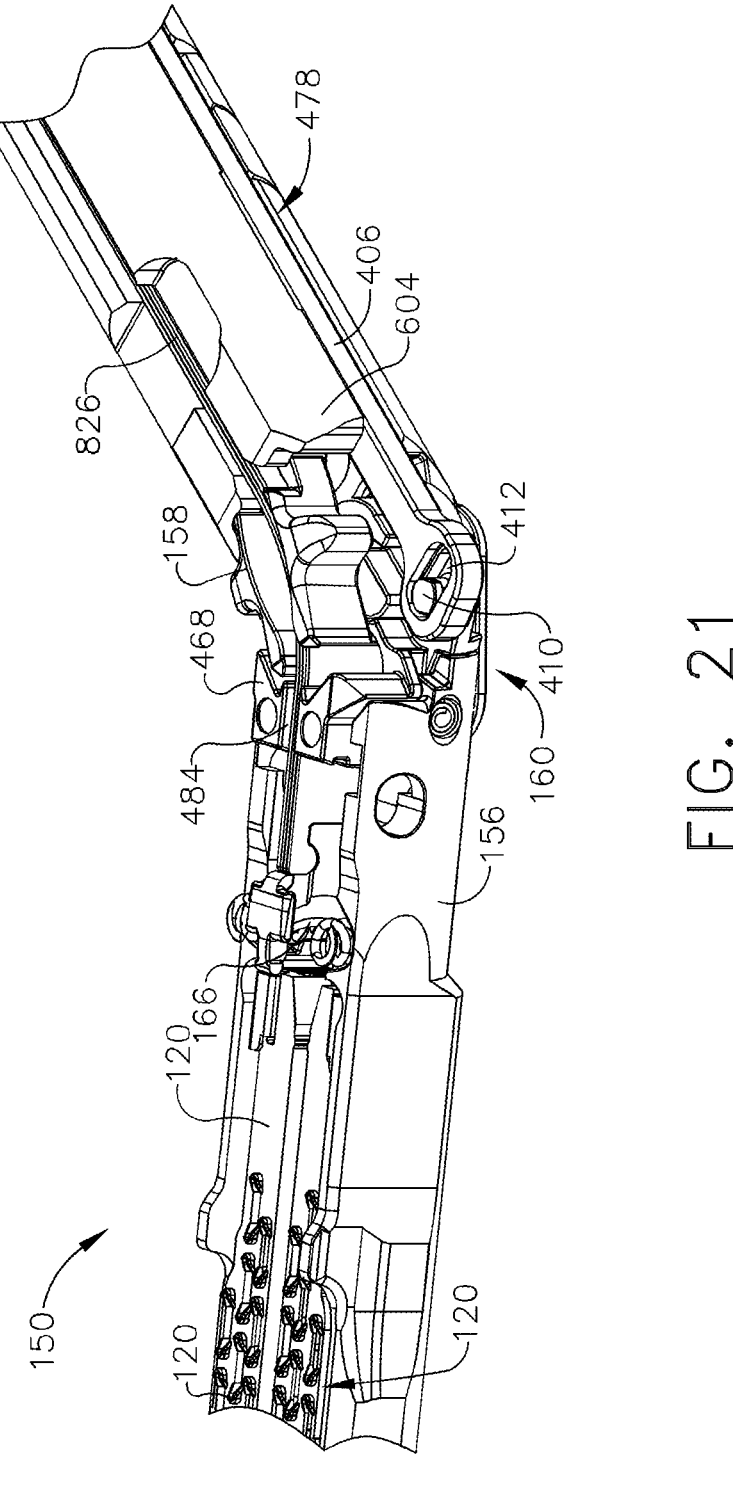
FIG. 21 shows articulation of an end effector relative to a shaft, according to aspects of the present disclosure.
Figures 22, 23, 24:
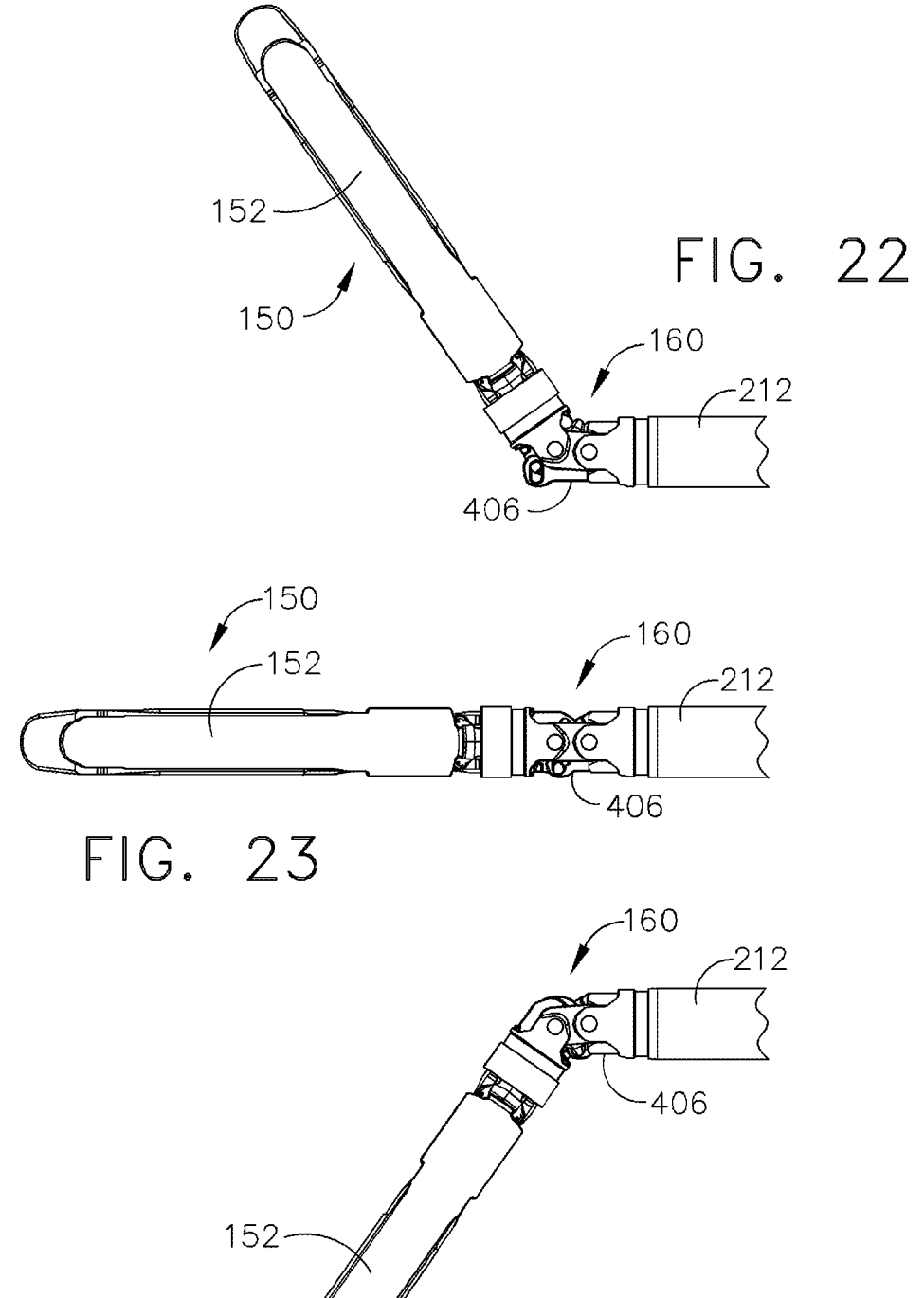
FIGS. 22-24 show articulation of an end effector relative to a shaft, according to aspects of the present disclosure

FIG. 20 shows the surgical instrument articulated to the right. FIG. 21 provides a detailed view of the articulating components of the surgical instrument 100. FIG. 22 shows the end effector 150 articulated to the right, FIG. 23 shows the end effector 150 without being articulated, and FIG. 24 shows the end effector 150 articulated to the left. In some examples, the articulation subsystem 400 described herein can achieve at least 60° of articulation in either direction, for example ±5°, ±10°, ±15°, ±20°, ±25°, ±30°, ±35°, ±40°, ±45°, ±50°, ±55°, ±60°, or any intervening degree of articulation back and forth. It will be noted that the joint 160 shown in FIGS. 22-24 that holds the end effector 150 to the shaft 604 is exposed for visualization. The joint 160 can be concealed by a flexible sheath 174 (see FIG. 1) to alleviate pinch points. The joint 160 described herein can include multiple articulation links that connect the closure tube 212 to the closure ring 226. This linking system can be a boss/hole configuration that provides a pinned joint. The exterior closure system can consist of the closure tube 212 pushing distally forward on the two articulation links of the joint 160, which in turn push on the closure ring 226.

Roll Subsystem

Figure 26:
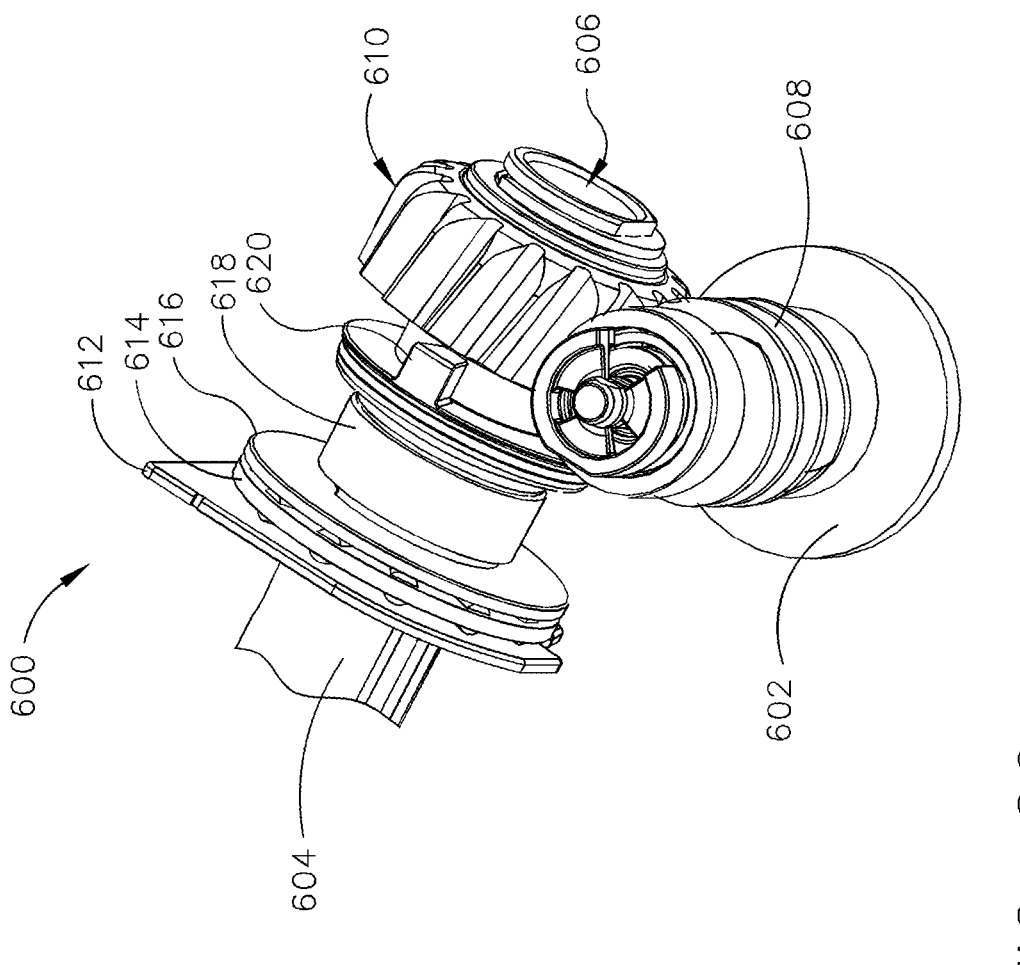
FIGS. 26-27 show components of a roll subsystem, according to aspects of the present disclosure.
Figure 37:
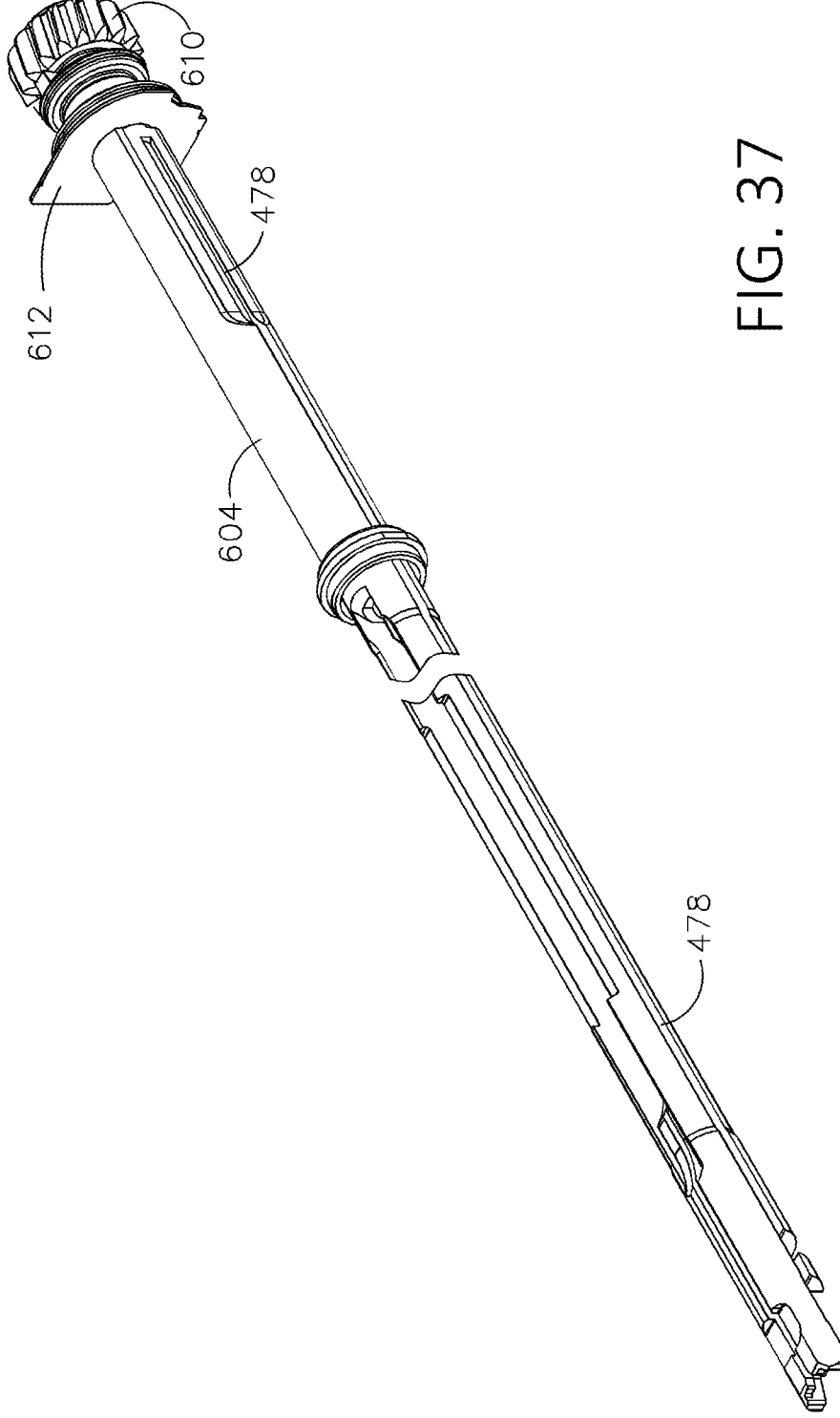
FIG. 37 shows shaft components of a surgical instrument, according to aspects of the present disclosure.

The surgical instrument 100 includes a roll subsystem 600. Detailed views of the proximal portions of an example roll subsystems 600 are provided in FIGS. 26-32D, whereas more distal portions of the example roll subsystem 600 are shown in FIG. 37. Referring specifically to FIG. 26, the roll subsystem 600 includes a series of gears that allow the shaft 604 to rotate around its longitudinal axis 474. The shaft 604 can be directly connected to the end effector 150, and therefore rolling of the shaft 604 enables the end effector 150 to roll the single articulation plane to any orthogonal position. The shaft 604 includes a shaft lumen 606 extending therethrough, and distal portions of a transection subsystem 800 extend through the shaft lumen 606. The transection subsystem 800 is described in greater detail below.

The roll subsystem 600 includes a roll input puck 602 that is engageable with a corresponding rotatable robotic output (e.g., roll robotic output 910 in FIG. 2). Robotic arm 1000 is also shown in the schematic of FIG. 2. The roll input puck 602 can be rotationally engaged with a worm gear 608 extending therefrom, such that rotation of the roll input puck 602 turns the worm gear 608. Since the roll input puck 602 is positioned perpendicular to the length of the surgical instrument 100, and therefore perpendicular to the shaft 604, the roll subsystem 600 includes a worm follower 610 that is engaged with the worm gear 608. The worm follower 610 can be coupled to the shaft 604, allowing rotation of the shaft 604. To keep the worm follower 610 positioned at the correct location relative to the worm gear 608, the roll subsystem 600 can include a stabilization plate 612 that surrounds the shaft 604 distal to the worm follower 610. The stabilization plate 612 can be positioned within a corresponding slot within the outer housing 102 to prevent the stabilization plate 612 from sliding axially along the shaft 604, while also providing the shaft 604 lateral alignment within the housing 102. The roll subsystem 600 can also include a roll bearing 614 and a roll bearing plate 616, the roll bearing 614 being positioned between the stabilization plate 612 and the roll bearing plate 616.

In some examples, the roll subsystem 600 includes a roll stop bushing 618 engaged with the rotatable shaft 604. The roll stop bushing 618 can be coupled to the worm follower 610 and/or shaft 604 and provide feedback on positioning of the rotatable shaft 604. For example, the roll stop bushing 618 can include a stop 620 positioned thereon that can contact a housing tab 626 positioned on the outer housing 102. The roll subsystem 600 can roll the shaft 604 to a first position where the roll stop bushing 618 contacts the housing tab 626 at a first side, and then roll the roll the shaft 604 to a second position where the roll stop bushing 618 contacts the housing tab 626 at a second, opposite side. The robotic output that actuates the roll subsystem 600 can use the hard stops at the housing tab 626 to determine a baseline, or 0°, rotation for the shaft 604. This example can provide the shaft 604 greater than 300° of rotation, for example greater than 305°, greater than 310°, greater than 315°, greater than 320°, greater than 325°, greater than 330°, greater than 335°, greater than 340°, greater than 345°, greater than 350°, greater than 355° of rotation, or more.

Figure 27:
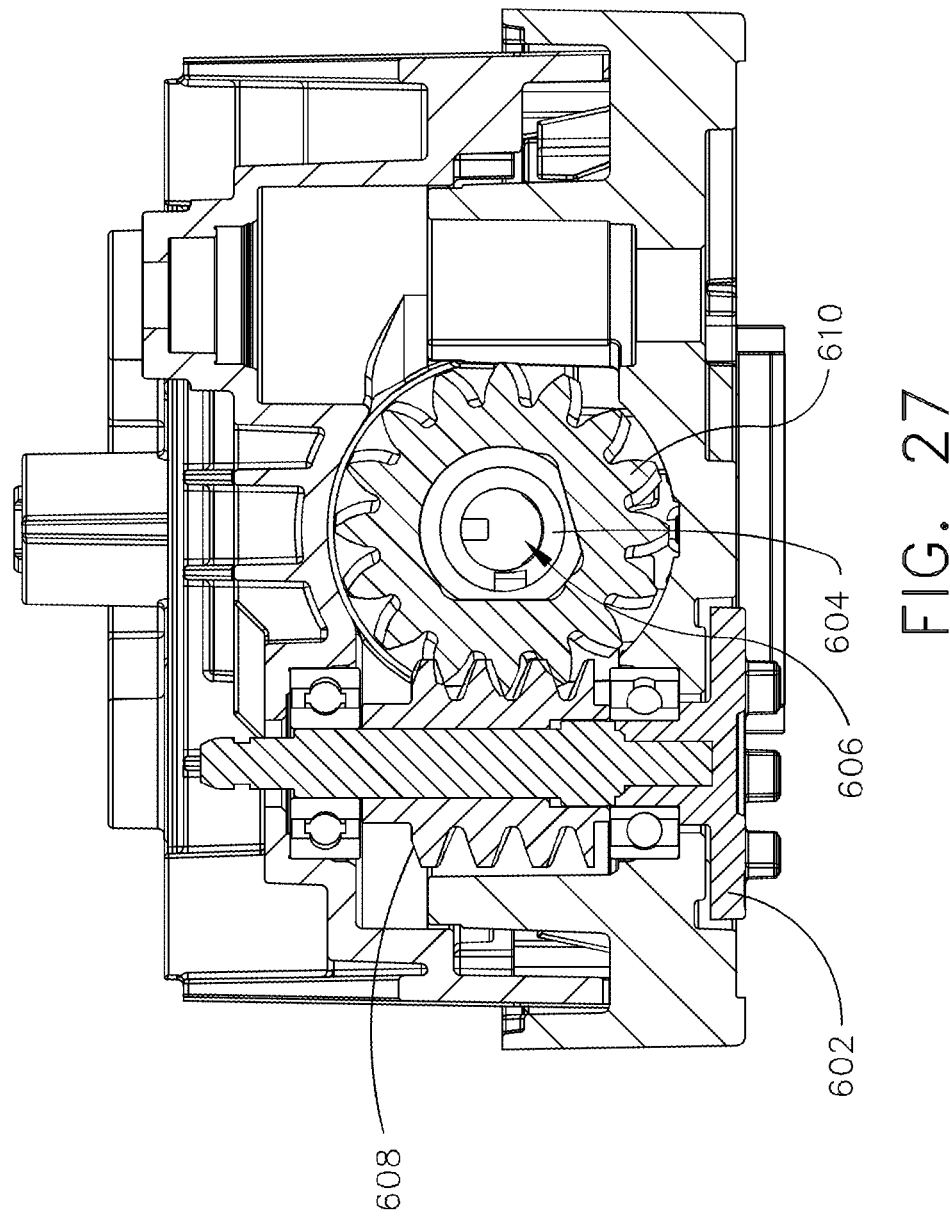
Figure 29:
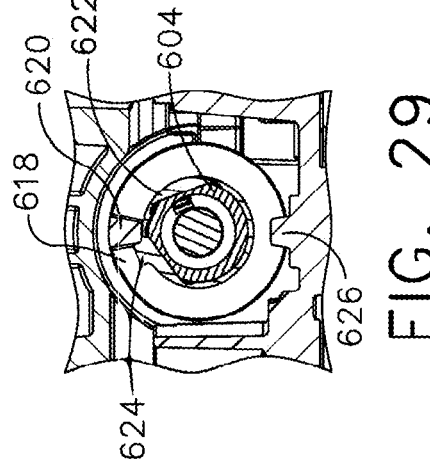
FIGS. 28-30 are end views of bushings for a roll subsystem, according to aspects of the present disclosure.
Figure 30:
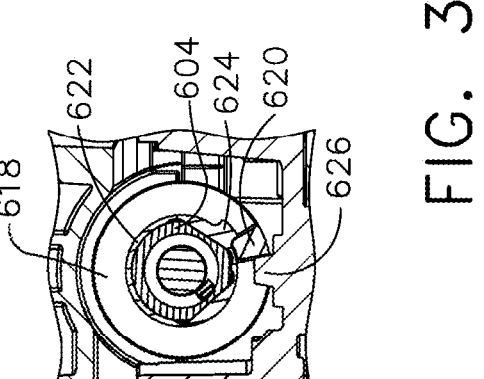
Figure 28:
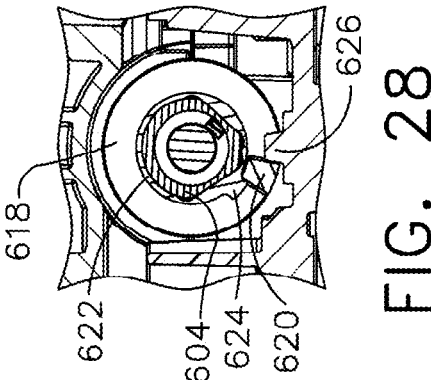

In some examples, and as shown in FIG. 27, the roll subsystem 600 can also include a follower bushing 622 having a follower bushing stop 624 extending therefrom. In this example, the follower bushing 622 can be positioned between the shaft 604 and the roll stop bushing 618. The shaft 604 and follower bushing 622 can be directly coupled to each other, and the roll stop bushing 618 and the follower bushing 622 can rotate relative to each other. The roll subsystem 600 can roll the shaft 604 to a first position where the roll stop bushing 618 contacts the housing tab 626, and the follower bushing 622 contacts the roll stop bushing 618 at a first side (see FIG. 28). The roll subsystem 600 can then rotate the shaft 604 until the follower bushing 622 contacts the roll stop bushing 618 at the other side, and then continue rotating by pushing the roll stop bushing 618 circumferentially (see FIG. 29) until the roll stop bushing 618 contacts the housing tab 626 and the follower bushing 622 contacts the roll stop bushing 618 at a second, opposite side (see FIG. 30). This example using the follower bushing 622 can provide a greater degree of rotation, for example greater than 360° of rotation, or in some instances about 320° of rotation in either direction (e.g., 640° in total). Referring briefly to FIG. 37, which shows distal portions of the roll subsystem 600, the view shows how the rod groove 478 of the shaft 604 can extend along the length of the shaft 604. The articulation rod 406 can extend through the rod groove 478 of the shaft 604, and rotation of the shaft 604 by the roll subsystem 600 can therefore rotate the articulation rod 406.

Figure 31B:
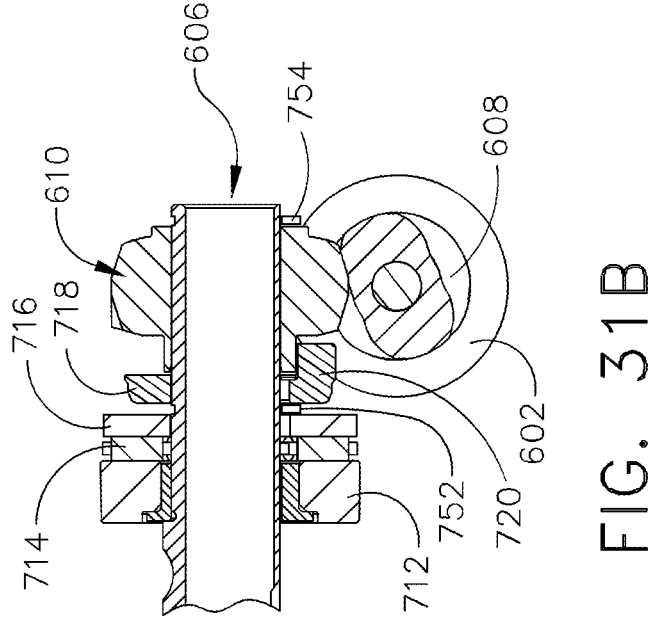
FIGS. 31A and 31B show alternative components of a roll subsystem, according to aspects of the present disclosure.
Figure 31A:
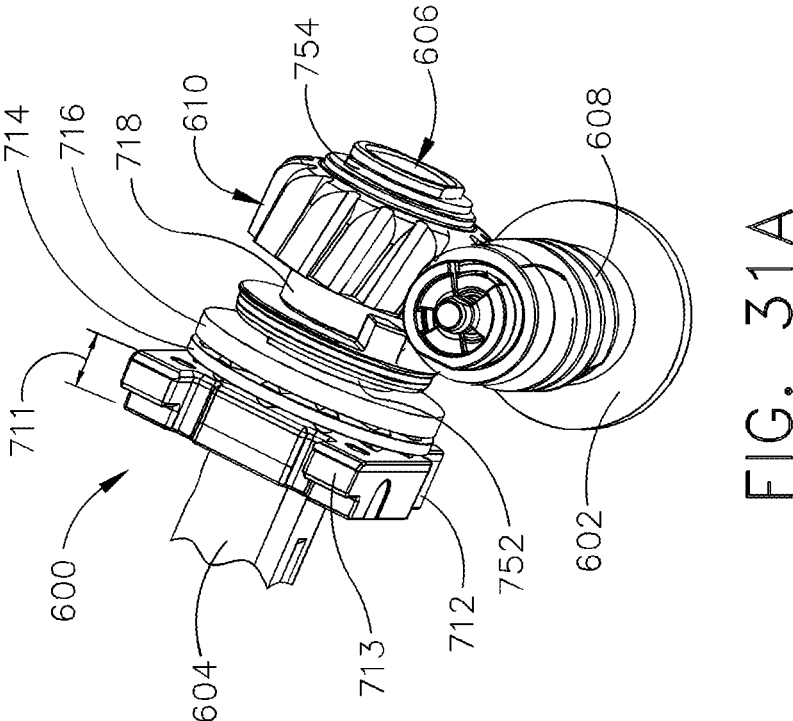

FIGS. 31A and 31B show alternative components of a roll subsystem 600 to the one shown in FIGS. 26 and 27, according to aspects of the present disclosure. FIG. 31A is a perspective view of the components of the roll subsystem 600. In the embodiment shown, the stabilization plate 612 shown in FIG. 26 has been replaced with a thicker thrust block 712. The thrust block 712 is positioned near the proximal end of the shaft 604 so as to counteract axial forces on the shaft 604 caused by distal movement of the closure tube 212 (see FIG. 1). Providing a more robust thrust block 712, including a thickness 711 greater than 1.0 cm, or greater than 1.5 cm, can provide better loading scenarios (to stop deflection) and can better share the load with the housing 102. The thrust block 712 can engage with a buttress 178, such as the buttress 178 shown in FIG. 43C. FIG. 31A shows additional components that can be included in the alternative design, including a roll bearing 714, which can be substantially similar to the roll bearing 614 in FIG. 26, and a roll bearing plate 716, which can be substantially similar to the roll bearing plate 616 in FIG. 26 (in FIG. 31A, the bearing plate 716 is thicker than the roll bearing plate 616 to further add to the robustness and load sharing at this component). FIG. 31A also shows a roll stop bushing 718, which can be substantially similar to roll stop bushing 618. FIG. 31B is a top, cross-sectional view of the components of the roll subsystem 600. The subsystem can include a first locking ring 752 and a second locking ring 754. The locking rings 752, 754 can be positioned such that they secure the worm follower 610 and the roll stop bushing 718 together. The stop 720 of the roll stop bushing 718 is also shown; the stop 720 can be substantially similar to stop 620 described above.

Referring to FIG. 27 for reference, as shown, the inside of the worm follower 610 may not be entirely round and, similarly, the outside surface of the shaft 604 may not be entirely round. Instead, the worm follower 610 and the shaft 604 can have corresponding anti-backlash features. It is desirable to reduce backlash in the gearing of a surgical instrument 100 to improve accuracy and to ensure proper calibration. For instance, a robot can home and/or calibrate roll by rolling the shaft 604 from one mechanical calibration position to another mechanical calibration position (see FIGS. 28-30 for a discussion of rotational constraints for the roll subsystem 600). Therefore, backlash reduction can help to ensure accurate calibration. The implementations shown in FIGS. 32A-32D provide examples of such anti-backlash features. FIG. 32A is a detailed view of the system also shown in FIG. 27. Here, the inside area of the worm follower 610 (i.e., the portion engaged with the shaft 604) includes one or more gear flats 756. A gear flat 756 can be used to ensure that the worm follower 610 constrains the shaft 604 so that they rotate together. The one or more gear flats 756 are positioned to abut and/or contact one or more corresponding shaft flats 758 on the exterior surface of shaft 604. In the example shown, the worm follower 610 comprises a first gear flat 756A and a second gear flat 756B, and the rotatable shaft 604 comprises (i) a first shaft flat 758A positioned to correspond to the first gear flat 756A and (ii) a second shaft flat 758B positioned to correspond to the second gear flat 756B. Having more than one flat can further limit backlash between the two components. In certain implementation, the first gear flat 756A can coincide with the portion of the shaft 604 that houses the rod groove 478 (see, e.g., FIG. 7A).

The one or more gear flats 756 may be milled, broached, or otherwise formed into the worm follower 610 and, as such, tight corners between the flat and curved section may not be possible or may not be desired, for instance because abrupt corners could be a location for stress fractures. Accordingly, the transitions between the one or more gear flats 756 and the curved section so as to provide gaps between the worm follower 610 and the shaft 604 at certain positions. Two such gaps are shown in FIG. 32A and are labeled as first gap 761A and second gap 761B. A first end of the first gear flat 756A is rounded and inwardly turned so as to come to a singular point 760. A first end of the second gear flat 756B is rounded and inwardly turned so as to come to the singular point 760. A portion of the worm follower 610 between the first gear flat 756A and the singular point 760 is separated from the rotatable shaft 604 by the aforementioned first gap 761A. A portion of the worm follower 610 between the second gear flat 756B and the singular point 760 is separated from the rotatable shaft 604 by the second gap 761B. The singular point 760 contacts the rotatable shaft 604 to provide the circumferential control of the shaft 604 within the worm follower 610.

FIGS. 32B-32D show additional or alternative anti-backlash features for the worm follower 610 and shaft 604. In FIG. 32B, the worm follower 610 includes a key 762 that engages with a keyway 734 in the shaft 604. Alternatively, the shaft 604 could include the key and the worm follower 610 the keyway. In some examples, the key/keyway could be combined with one of the other anti-backlash features, such as first shaft flat 758A and first gear flat 756A, as shown. In FIG. 32C, the example shown also includes a key 762 and a keyway 734, but the keyway 734 extends entirely through the wall of the shaft 604. In FIG. 32D, the worm follower 610 has different wall thickness, as measured to the inside surface of the worm follower 610 that contacts the shaft 604. The worm follower 610 has a first portion with a first wall thickness 767A and a second portion with a second wall thickness 767B, the first wall thickness 767A being thicker than the second wall thickness 767B. This change in the interior wall geometry thereby forms a gear step 766. Similarly, the rotatable shaft 604 has a first portion with a first wall thickness 769A and a second portion with a second wall thickness 769B, the first wall thickness 769A being thicker than the second wall thickness 769B. This change in the interior wall geometry of the shaft 604 thereby forms a shaft step 768. The gear step 766 is sized and positioned to engage with the shaft step 768 to reduce backlash as the worm gear 608 actuates the worm follower 610. It is also contemplated that the worm follower 610 and shaft 604 are inseparably connected, such as with a weld or adhesive, though manufacturing a connected embodiment may take additional steps in manufacturing.

Figures 33A, 33B:
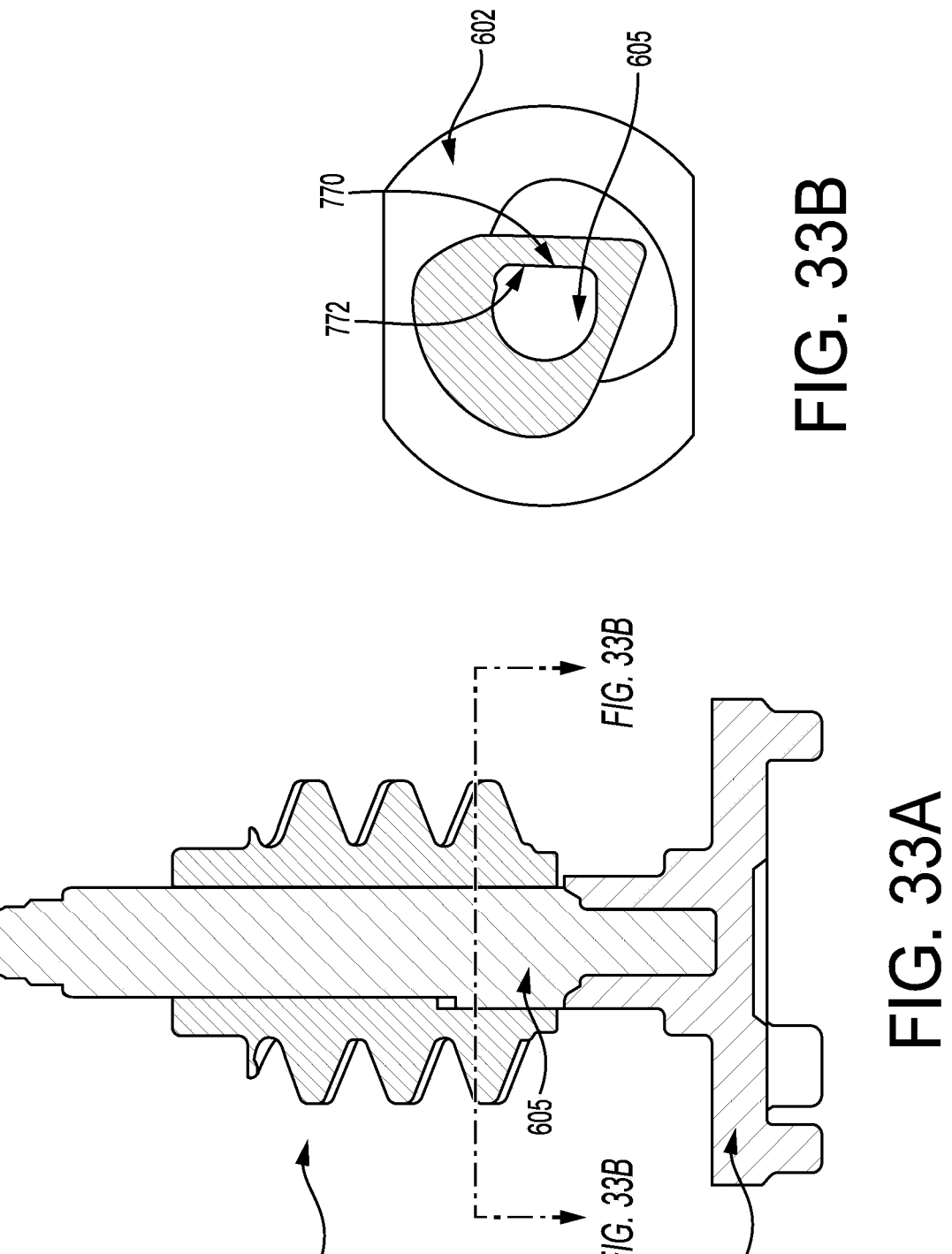
FIGS. 33A and 33B show example anti-backlash features for a worm gear, according to aspects of the present disclosure.

FIGS. 33A and 33B show example anti-backlash features for a worm gear 608, according to aspects of the present disclosure. The disclosure above discussed reducing backlash at the connection between the shaft 604 and worm follower 610, but another point of potential backlash in the roll subsystem 600 is where the roll input puck 602 and its respective input shaft 605 engages with the worm gear 608. FIG. 33A shows the placement of the input puck 602, input shaft 605, and worm gear 608, whereas the top FIG. 33B cross sectional view shows the example anti-backlash features. The input shaft 605 extends at least partially through the worm gear 608. The input shaft 605 includes a flat section 772 positioned to correspond to a worm drive flat 770 of the worm gear 608. This flat-on-flat feature is similar to the gear flats 756 and shaft flats 758 discussed with respect to FIG. 32A.

Transection Subsystem

Figure 34:
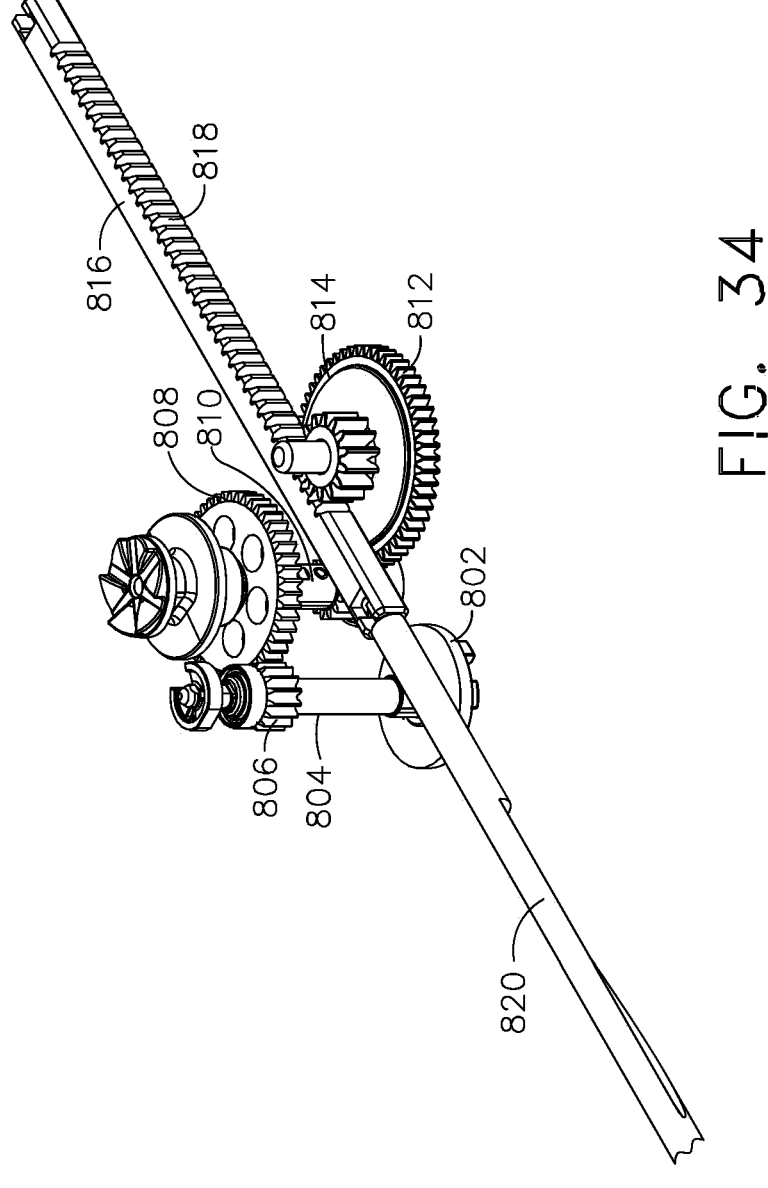
FIG. 34 shows components of a transection subsystem, according to aspects of the present disclosure.

The surgical instrument 100 includes a transection subsystem 800. This subsystem can be referred to as a transection subsystem since actuation of the system results in a cutting of tissue via cutting mechanisms of the end effector 150, mechanisms of which are described in more detail below. The transection subsystem 800 includes a series of gears proximally that allow the system to fire a firing rack 816 distally. Because the surgical instrument 100 can have a roll feature, e.g., via the roll subsystem 600, the proximal portion of the transection subsystem 800 (e.g., with the gearing and firing rack 816, see FIGS. 34-37) is not rotatable, but the distal end (e.g., firing rod 820, bands 826, etc., see FIGS. 38 and 37) can rotate along with the roll of the shaft 604. Referring specifically now to FIG. 34, the transection subsystem 800 includes a transection input puck 802 that is engageable with a corresponding rotatable robotic output (e.g., transection robotic output 912 in FIG. 2). Robotic arm 1000 is also shown in the schematic of FIG. 2. The transection input puck 802 can be rotationally engaged with a transection drive shaft 804 extending therefrom, such that rotation of the transection input puck 802 turns the transection drive shaft 804. Rotation of the transection drive shaft 804 causes, either directly or indirectly via gearing, distal translation of the firing rack 816, which results in firing of the staples 126 and/or knife 166 in the end effector. Although not visible in the figure because they are inside of the cartridge 120, staples 126 are located as indicated in FIG. 41. FIGS. 41 and 42 also shows a sled 122, which can be used to expel staples from the cartridge 120.

Figure 43C:
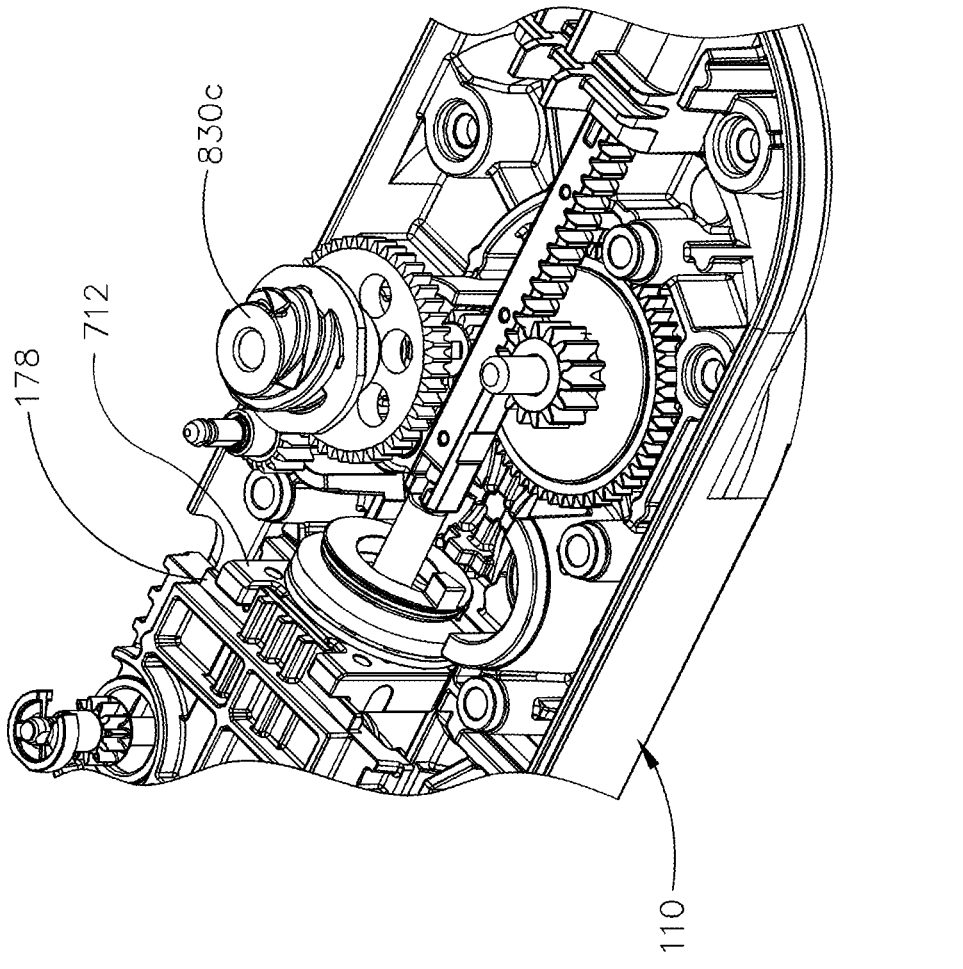
FIG. 43C is a perspective view of a portion of a transection subsystem and roll subsystem, with a thrust block engaged with a buttress portion of the housing, according to aspects of the present disclosure.

Since the distal translation of the firing rack 816 is used to translate a distal knife 166, a higher degree of force is desired for the distal translation. The force needed to push the knife 166 forward can be great, as it can include the accumulation of forces required to cut tissue, drive staples, and interact with any friction. As such, the present disclosure provides a series of gearing to increase the transection, or cutting, force by providing a mechanical advantage past the transection input puck 802. The transection subsystem 800 includes a transection spur gear 806 that is coupled to the transection drive shaft 804 such that rotation of the transection drive shaft 804 also turns the transection spur gear 806. The transection subsystem 800 can include a transection ramp gear 808 that is rotatably engaged with the transection spur gear 806, meaning that rotation of the transection spur gear 806 in a first direction causes a corresponding rotation of the transection ramp gear 808 in the opposite direction. The transection ramp gear 808 can have a larger diameter than the transection spur gear 806. A ramp gear shaft 810 can be coupled to and extend from the transection ramp gear 808, such that the ramp gear shaft 810 rotates with the rotation of the transection ramp gear 808. A transection ramp spur gear 811 can be coupled to the ramp gear shaft 810 such that the transection ramp spur gear 811 can be caused to rotate when the ramp gear shaft 810 rotates. FIGS. 5A and 6A also show a key receiver 830 that that is rotationally coupled to the gearing of the transection subsystem 800 to manually retract the firing rack 816 and thus knife 166. A similar key receiver 830A is shown in FIG. 43C. The knife 166 can be retained at a closed non-fired "home" position (see FIG. 42) by a leaf spring 168.

The transection subsystem 800 can include a speed gear 812 that is rotatably engaged with the transection ramp spur gear 811, meaning that rotation of the ramp gear shaft 810 in a first direction causes a corresponding rotation of the speed gear 812 in the opposite direction. The speed gear 812 can have a larger diameter than the ramp gear shaft 810 and the transection ramp gear 808. The transection spur gear 806, transection ramp gear 808, transection ramp spur gear 811, and speed gear 812 shown in FIG. 34 are all spur gears.

The transection subsystem 800 includes a firing gear 814 that is rotationally dependent on the gearing, for example rotation of the firing gear 814 is ultimately dependent on rotation of the transection input puck 802. In the examples with a speed gear 812, the firing gear 814 can be rotatable with rotation of the speed gear 812. The firing gear 814 is engaged with teeth 818 of the firing rack 816, such that rotation of the firing gear 814 causes a distal translation of the firing rack 816. As will be appreciated, the differences in gear sizes of the transection subsystem 800 can increase the linear velocity of the firing rack 816.

As described above, the firing rack 816 can be rotationally stable within the outer housing 102, but because the more distal end of the transection subsystem 800 must rotate with the roll features of the roll subsystem 600, the distal portion of the transection subsystem 800 can rotate independent of the firing rack 816. The transection subsystem 800 can have a firing rod 820 rotatably coupled to the distal end of the firing rack 816, such that the firing rod 820 can rotate independent of the firing rack 816. The rotatable connector between the firing rod 820 and the firing rack 816 can include a T-shaped tab 822 on the proximal end of the firing rod 820 that engages with a slot 824 on the firing rack 816. The tab/slot connection allows free rotation of the firing rod 820 but also constrains the firing rod 820 to the firing rack 816 axially. An example of this connection between the firing rod 820 and the firing rack 816 is shown in FIGS. 38 and 41.

Referring to FIGS. 38 and 41, which provide a detailed view of certain distal components of the transection subsystem 800, the distal end of the firing rod 820 can be coupled to a series of bands 826 that extend distally toward the end effector 150. These bands provide a degree of flexibility to the firing mechanism, while also providing axial stiffness to push the knife 166 through tissue. The surgical instrument 100 can include a knife insert retainer 838 that protects the bands 826 (see FIG. 35). FIG. 21 further shows the bands 826 distally. The surgical instrument 100 can include knife guide 158 at a joint 160 that allows the end effector 150 to articulate as described herein. The bands 826 can pass through the knife guide 158, and the knife guide 158 provides lateral support to guide the laminates through any articulation angle. The bands 826 can also pass through the band slot 484 of the attachment end 468 of the distal channel retainer 408.

Any of the closure subsystems 200, articulation subsystems 400, roll subsystems 600, or transection subsystems 800 described herein can be, respectively, substituted by or combined with any of the closure subsystems 200, articulation subsystems 400, roll subsystems 600, or transection subsystems 800 described in U.S. Provisional Application No. 63/515,001 or those described in U.S. Provisional Application No. 63/634,171 (END9568USPSP2), both of which are incorporated herein by reference in their entireties. Any of the end effectors 150 described herein can be substituted by or combined with any of the end effectors 150 described in U.S. Provisional Application No. 63/515,001 or those described in U.S. Provisional Application No. 63/634, 171 (END9568USPSP2), both of which are incorporated herein by reference in their entireties.

Clauses

Examples of the present disclosure can be implemented by any of the following numbered clauses:

Clause 1: An articulation subsystem (400) for a surgical instrument (100) comprising: a rotatable shaft (604) having a longitudinal axis (474); a distal channel retainer (408) coupled to an end effector (150), the distal channel retainer (408) being pivotable about an articulation joint (466); a first articulation bushing (426, 526) slidable from a first position to a second position along the longitudinal axis (474) of the rotatable shaft (604); an articulation rod (406) extending distally from the first articulation bushing (426) and coupled at a distal end (472) to the distal channel retainer (408); and a first rack (414, 514) movable with respect to the longitudinal axis (474) of the rotatable shaft (604), wherein movement of the first rack (414, 514) with respect to the longitudinal axis (474) imparts an axial force onto the first articulation bushing (426, 526) moving the first articulation bushing (426, 526) from the first position to the second position, and wherein movement of the first articulation bushing (426) from the first position to the second position actuates the articulation rod (406) causing the distal channel retainer (408) to pivot about the articulation joint (466).

Clause 2: The articulation subsystem (400) according to Clause 1, wherein the first articulation bushing (426) is rotationally independent of the first rack (414).

Clause 3: The articulation subsystem (400) according to Clause 1 or 2 further comprising a first rack gear (434) engaged with the first rack (414, 514), wherein rotation of the first rack gear (434) moves the first rack (414, 514) with respect to the longitudinal axis (474).

Clause 4: The articulation subsystem (400) according to Clause 3 further comprising: a first articulation input puck (402) engageable with a first articulation robotic output (906); a first articulation drive shaft (432) extending from the first articulation input puck (402) and comprising a first drive gear (430); and a first compound gear (442) engaged with the first drive gear (430) and the first rack gear (434), wherein rotation of the first articulation input puck (402) rotates the first rack gear (434) moving the first rack (414, 514) with respect to the longitudinal axis (474).

Clause 5: The articulation subsystem (400) according to Clause 4, wherein the first rack gear (434) is a tube gear, and the first articulation drive shaft (432) is positioned within the first rack gear (434).

Clause 6: The articulation subsystem (400) according to any one of Clauses 1 to 5 further comprising: a second articulation bushing (428) slidable from a third position to a fourth position along the longitudinal axis (474) of the rotatable shaft (604); and a second rack (418, 518) movable with respect to the longitudinal axis (474) of the rotatable shaft (604), movement of the second rack (418, 518) with respect to the longitudinal axis (474) imparts an axial force onto the second articulation bushing (428) to move the second articulation bushing (428) from the third position to the fourth position.

Clause 7: The articulation subsystem (400) according to Clause 6 further comprising a second rack gear (440) engaged with the second rack (418), wherein rotation of the second rack gear (440) moves the second rack (418) with respect to the longitudinal axis (474).

Clause 8: The articulation subsystem (400) according to Clause 7 further comprising: a second articulation input puck (404) engageable with a second articulation robotic output (908); a second articulation drive shaft (438) extending from the second articulation input puck (404) and comprising a second drive gear (436); and a second compound gear (448) engaged with the second drive gear (436) and the second rack gear (440), rotation of the second articulation input puck (404) rotates the second rack gear (440) moving the second rack (418) with respect to the longitudinal axis (474).

Clause 9: The articulation subsystem (400) according to Clause 8, wherein the second rack gear (440) is a tube gear, and the second articulation drive shaft (438) is positioned within the second rack gear (440).

Clause 10: The articulation subsystem (400) according to Clause 7 or 9, wherein movement of the second articulation bushing (428) and the first articulation bushing (426) is antagonistic such that the second articulation bushing (428) is movable by the second rack (418) to translate the first articulation bushing (426) distally along the longitudinal axis (474), and the first articulation bushing (426) is movable by the first rack (414) to translate the second articulation bushing (428) proximally along the longitudinal axis (474).

Clause 11: The articulation subsystem (400) according to any one of Clauses 6 to 10, wherein the second articulation bushing (428) and the first articulation bushing (426) are coupled.

Clause 12: The articulation subsystem (400) according to any one of Clauses 1 to 11 further comprising a first articulation bearing (422, 522), wherein the first rack (414, 514) comprises a first bearing surface (458, 558), and the first articulation bearing (422, 522) is disposed between the first bearing surface (458, 558) and the first articulation bushing (426, 526).

Clause 13: The articulation subsystem (400) according to Clause 12, wherein the first bearing surface (458) is semi-circular.

Clause 14: The articulation subsystem (400) according to Clause 12 or 13, wherein the first rack (414, 514) comprises a first housing track surface (462, 562a, 562b) slidable within a track (176) in an outer housing (102).

Clause 15: The articulation subsystem (400) according to Clause 14, wherein the first housing track surface (462) and the first bearing surface (458) are at 90° with respect to each other.

Clause 16: The articulation subsystem (400) according to any one of Clauses 1 to 15, wherein the articulation rod (406) is slidable through a rod groove (478) in the rotatable shaft (604).

Clause 17: The articulation subsystem (400) according to any one of Clauses 1 to 16, further comprising a first rack gear (434), wherein rotation of the first rack gear (434) causes the movement of the first rack (414, 514).

Clause 18: The articulation subsystem (400) according to Clause 17, wherein the first rack gear (434) comprises first gear teeth (446), wherein the first rack (414, 514) comprises first rack gearing (416, 516), and wherein the first gear teeth (446) are configured to engage with the first rack gearing (416, 516).

Clause 19: The articulation subsystem (400) according to Clause 18, wherein the first rack (514) is positioned between the first rack gear (434) and the rotatable shaft (604).

Clause 20: The articulation subsystem (400) according to Clause 18, wherein the first rack gear (434) is positioned between the first rack (414) and the rotatable shaft (604).

Clause 21: The articulation subsystem (400) according to any one of Clauses 17-20 further comprising: a second rack (418, 518) movable with respect to the longitudinal axis (474) of the rotatable shaft (604); and a second rack gear (440), wherein rotation of the second rack gear (440) causes the movement of the second rack (418, 518).

Clause 22: The articulation subsystem (400) according to Clause 21, wherein the second rack gear (440) comprises second gear teeth (452), wherein the second rack (418, 518) comprises second rack gearing (420, 520), and wherein the second gear teeth (452) are configured to engage with the second rack gearing (420, 520).

Clause 23: The articulation subsystem (400) according to Clause 21, wherein the second rack (518) is positioned between the second rack gear (440) and the rotatable shaft (604).

Clause 24: The articulation subsystem (400) according to Clause 21, wherein the second rack gear (440) is positioned between the second rack (418) and the rotatable shaft (604).

Clause 25: An articulation subsystem (400) for a surgical instrument (100) comprising: a rotatable shaft (604) having a longitudinal axis (474); an articulation rod (406) extending along the longitudinal axis (474) of the rotatable shaft (604) and being rotationally coupled to the rotatable shaft (604); a first articulation bushing (426, 526) slidable from a first position to a second position along the longitudinal axis (474) of the rotatable shaft (604), the first articulation bushing (426, 526) being rotationally coupled to the rotatable shaft (604); a first rack (414, 514) movable with respect to the longitudinal axis (474) of the rotatable shaft (604), the first rack (414, 514) being rotationally independent of the rotatable shaft (604) and the first articulation bushing (426, 526); and a first rack gear (434) engaged with the first rack (414, 514), wherein rotation of the first rack gear (434) moves the first rack (414, 514) with respect to the longitudinal axis (474), and wherein movement of the first rack (414, 514) with respect to the longitudinal axis (474) imparts an axial force onto the first articulation bushing (426, 526) moving the first articulation bushing (426, 526) from the first position to the second position.

Clause 26: The articulation subsystem (400) according to Clause 25, further comprising a first rack gear (434), wherein rotation of the first rack gear (434) causes the movement of the first rack (414, 514).

Clause 27: The articulation subsystem (400) according to Clause 25 or 26 further comprising: a second rack (418, 518) movable with respect to the longitudinal axis (474) of the rotatable shaft (604); and a second rack gear (440), wherein rotation of the second rack gear (440) causes the movement of the second rack (418, 518).

Clause 28: The articulation subsystem (400) according to Clause 27, wherein the second rack gear (440) comprises second gear teeth (452), wherein the second rack (418, 518) comprises second rack gearing (420, 520), and wherein the second gear teeth (452) are configured to engage with the second rack gearing (420, 520).

Clause 29: The articulation subsystem (400) according to Clause 27 or 28, wherein the second rack (518) is positioned between the second rack gear (440) and the rotatable shaft (604).

Clause 30: The articulation subsystem (400) according to Clause 27 or 28, wherein the second rack gear (440) is positioned between the second rack (418) and the rotatable shaft (604).

Clause 31: The articulation subsystem (400) according to Clause 27, wherein the first rack (514) and the second rack (514) abut to form a hollow cylinder.

Clause 32: The articulation subsystem (400) according to Clause 27, wherein the second rack gear (440) comprises second gear teeth (452), wherein the first rack (514) comprises second rack gearing (520), and wherein the second gear teeth (452) are configured to engage with the second rack gearing (520).

Clause 33: The articulation subsystem (400) according to Clause 32, wherein the second rack gearing (520) is positioned diametrically opposite the first rack gearing (516) on a surface of the first rack (514).

Clause 34: The articulation subsystem (400) according to any one of Clauses 25 to 33, wherein the first rack (514) is a cylindrical component comprising a lumen (530) extending through, wherein the first articulation bushing (526) is positioned within the lumen (530).

Clause 35: The articulation subsystem (400) according to Clause 34, wherein the first articulation bushing (526) comprises a distal flange (528), and the first rack (514) is axially constrained distally by the distal flange (528).

Clause 36: The articulation subsystem (400) according to Clause 35, wherein the first articulation bushing (526) is axially constrained proximally by a locking ring (568).

Clause 37: The articulation subsystem (400) according to any one of Clauses 25 to 36 further comprising a first articulation bearing (422, 522), wherein the first rack (414, 514) comprises a first bearing surface (458, 558), and the first articulation bearing (422, 522) is disposed between the first bearing surface (458, 558) and the first articulation bushing (426, 526).

Clause 38: The articulation subsystem (400) according to Clause 37, wherein the first bearing surface (458) is semicircular.

Clause 39: The articulation subsystem (400) according to Clause 37 or 38, wherein the first rack (414, 514) comprises a first housing track surface (462, 562*a*, 562*b*) slidable within a track (176) in an outer housing (102).

The invention is not necessarily limited to the examples described, which can be varied in construction and detail. The terms "distal" and "proximal" are used throughout the preceding description and are meant to refer to a positions and directions relative to attachment to a robotic arm. As such, "distal" or distally" refer to a position distant to or a direction away from the robotic arm (i.e., a direction toward a patient). Similarly, "proximal" or "proximally" refer to a position near or a direction towards the robotic arm. Furthermore, the singular forms "a," "an," and "the" include plural referents unless the context clearly dictates otherwise. Furthermore, the use of "couple", "coupled", or similar phrases should not be construed as being limited to a certain number of components or a particular order of components unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 71% to 99%.

Use of the term "transection" or "transection subsystem" is not intended to be limiting to any particular method of use for the components being described. The term "transection" is used since the exemplary embodiments shown in the figures include a knife 166 that transects tissue as it is fired, whereas the same feature can also be used to drive the staples 126. Some implementations may not include a knife 166 at the end, and thus the system may be for stapling alone. The subsystems described herein, including the transection subsystem, can be effective in those staple-only examples as well. Accordingly, the term "transection" and "transection subsystem" can be understood to mean a firing, or driving, of the components of the end effector, whether those components be a knife, a staple, or both.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

What is claimed is:

1. An articulation subsystem for a surgical instrument comprising:

a rotatable shaft having a longitudinal axis;

an articulation rod extending along the longitudinal axis of the rotatable shaft and being rotationally coupled to the rotatable shaft;

a first articulation bushing slidable from a first position to a second position along the longitudinal axis of the rotatable shaft, the first articulation bushing being rotationally coupled to the rotatable shaft;

a first rack comprising first rack gearing, the first rack movable with respect to the longitudinal axis of the rotatable shaft, the first rack being rotationally independent of the rotatable shaft and the first articulation bushing;

a first rack gear comprising first teeth engageable with the first rack gearing;

a second rack comprising second rack gearing, the second rack movable with respect to the longitudinal axis of the rotatable shaft, the second rack and first rack together forming a cylinder with a lumen therethrough; and a second rack gear comprising second teeth engageable with the second rack gearing, the second rack gearing positioned diametrically opposite the first rack gearing on an outer surface of the cylinder, wherein rotation of the second rack gear moves the second rack with respect to the longitudinal axis, wherein rotation of the first rack gear moves the first rack with respect to the longitudinal axis, and wherein movement of the first rack with respect to the longitudinal axis imparts an axial force onto the first articulation bushing moving the first articulation bushing from the first position to the second position.

2. The articulation subsystem according to claim 1, wherein the second rack is positioned between the second rack gear and the rotatable shaft.

3. The articulation subsystem according to claim 1, wherein the first rack and the second rack are integral.

4. The articulation subsystem according to claim 3, wherein the first articulation bushing comprises a distal flange, and the first rack is axially constrained distally by the distal flange.

5. The articulation subsystem according to claim 4, wherein the first articulation bushing is axially constrained proximally by a locking ring.

6. The articulation subsystem according to claim 3 further comprising a first articulation bearing, wherein the first rack comprises a first bearing surface, and the first articulation bearing is disposed between the first bearing surface and the first articulation bushing.

7. The articulation subsystem according to claim 6, wherein the first bearing surface is semicircular.

8. The articulation subsystem according to claim 6, wherein the first rack comprises a first housing track surface slidable within a track in an outer housing.

9. An articulation subsystem for a surgical instrument comprising:

a rotatable shaft having a longitudinal axis;

an articulation rod extending along the longitudinal axis of the rotatable shaft and being rotationally coupled to the rotatable shaft;

a first articulation bushing slidable from a first position to a second position along the longitudinal axis of the rotatable shaft, the first articulation bushing being rotationally coupled to the rotatable shaft;

a first rack comprising a first articulation bearing surface, the first rack being movable with respect to the longitudinal axis of the rotatable shaft, and being rotationally independent of the rotatable shaft and the first articulation bushing;

a first rack gear engaged with the first rack; and a first articulation bearing disposed between the first bearing surface of the first rack and the first articulation bushing, wherein rotation of the first rack gear moves the first rack with respect to the longitudinal axis, and wherein movement of the first rack with respect to the longitudinal axis imparts an axial force onto the first articulation bushing moving the first articulation bushing from the first position to the second position.

10. The articulation subsystem according to claim 9, wherein the first bearing surface is semicircular.

11. The articulation subsystem according to claim 9, wherein the first rack comprises a first housing track surface slidable within a track in an outer housing.

12. The articulation subsystem according to claim 9, wherein the first articulation bearing enables the first articulation bushing to rotate independent of the first rack.

13. The articulation subsystem according to claim 12 further comprising a second articulation bearing, wherein the first articulation bearing is positioned proximate a distal end of the first rack, and the second articulation bearing is positioned proximate a proximal end of the first rack.

14. The articulation subsystem according to claim 13, wherein the first articulation bearing is constrained distally by a flange of the first articulation bushing, and the second articulation bearing is constrained proximally by a locking ring.

\*    \*    \*    \*    \*